US012799488B2

(12) United States Patent
Liu et al.

(10) Patent No.: US 12,799,488 B2
(45) Date of Patent: Nov. 17, 2026

(54) CARBOXYPEPTIDASE B2 (CPB2) iRNA COMPOSITIONS AND METHODS OF USE THEREOF

(71) Applicant: Alnylam Pharmaceuticals, Inc., Cambridge, MA (US)

(72) Inventors: Jingxuan Liu, West Roxbury, MA (US); James D. McIninch, Burlington, MA (US); Patrick Haslett, Somerville, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 1167 days.

(21) Appl. No.: 17/588,393

(22) Filed: Jan. 31, 2022

(65) Prior Publication Data

US 2022/0228151 A1 Jul. 21, 2022

Related U.S. Application Data

(63) Continuation of application No. PCT/US2020/044398, filed on Jul. 31, 2020.

(60) Provisional application No. 62/881,517, filed on Aug. 1, 2019.

(51) Int. Cl.
*C12N 15/113* (2010.01)

(52) U.S. Cl.
CPC ...... *C12N 15/1137* (2013.01); *C12N 2310/14* (2013.01); *C12N 2310/315* (2013.01); *C12N 2310/321* (2013.01); *C12N 2310/322* (2013.01); *C12N 2310/3515* (2013.01); *C12Y 304/1702* (2013.01)

(58) Field of Classification Search
CPC .................................................. C12N 2310/14
See application file for complete search history.

(56) References Cited

U.S. PATENT DOCUMENTS

| | | | | |
|---|---|---|---|---|
| 7,091,331 | B2 | 8/2006 | Tamura et al. | |
| 2008/0113351 | A1* | 5/2008 | Naito | A61P 5/26 536/23.1 |
| 2010/0035983 | A1* | 2/2010 | Shiffman | A61P 9/00 514/510 |
| 2022/0000778 | A1* | 1/2022 | Heyes | A61K 31/713 |
| 2022/0031847 | A1* | 2/2022 | Heyes | C12N 15/111 |

OTHER PUBLICATIONS

Chao Yu et. al. (Molecular Medicine Reports 16.3, pp. 3469-3474, 2017) (Year: 2017).*
Boffa et. al. (Clinical Biochemistry 40, pp. 431-442, 2007) (Year: 2007).*
Androsavich, “Frameworks for transformational breakthroughs in RNA-based medicines”, Nature Reviews Drug Discovery, vol. 23, Jun. 2024, 421-444.
Foster et al., “Advanced siRNA Designs Further Improve In Vivo Performance of GalNAc-siRNA Conjugates”, Mol Ther. Mar. 7, 2018;26(3):708-717.
Ui-Tei et al., “Functional dissection of siRNA sequence by systematic DNA substitution: modified siRNA with a DNA seed arm is a powerful tool for mammalian gene silencing with significantly reduced off-target effect”, Nucleic Acids Res. Apr. 2008;36(7):2136-51.
Chernikov et al., “Current Development of siRNA Bioconjugates: From Research to the Clinic”, Front Pharmacol. Apr. 26, 2019:10:444.
Hu et al., “Therapeutic siRNA: state of the art”, Signal Transduction and Targeted Therapy (2020) 5:101.
Nair et al., “Impact of enhanced metabolic stability on pharmacokinetics and pharmacodynamics of GalNAc-siRNA conjugates”. Nucleic Acids Res. Nov. 2, 2017;45(19):10969-10977.
Shukla et al., “Exploring chemical modifications for siRNA therapeutics: a structural and functional outlook”, ChemMedChem. Mar. 1, 2010;5(3):328-49.
Nair et al. “Multivalent N-Acetylgalactosamine-Conjugated siRNA Localizes in Hepatocytes and Elicits Robust RNAi-Mediated Gene Silencing” J. Am. Chem. Soc. 2014, 136, 16958-16961.
Vickers et al., Efficient reduction of target RNAs by small interfering RNA and RNase H-dependent antisense agents. A comparative analysis. J Biol Chem. Feb. 28, 2003;278(9):7108-18.
Reynolds et al., Rational siRNA design for RNA interference. Nat Biotechnol. Mar. 2004;22(3):326-30.
Haraszti et al., “5'-Vinylphosphonate improves tissue accumulation and efficacy of conjugated siRNAs in vivo”, Nucleic Acids Research, vol. 45, No. 13, Jun. 7, 2017 (Jun. 7, 2017), pp. 7581-7592.
Yu et al., “Suppression of TAFI by siRNA inhibits invasion and migration of breast cancer cells”, Molecular Medicine Reports, vol. 16, No. 3, Mar. 18, 2017 (Mar. 18, 2017), pp. 3469-3474.
International Preliminary Report on Patentability from PCT/US2020/044398, mailed Feb. 10, 2022.
Boffa et al., “Curiouser and curiouser: Recent advances in measurement of thrombin-activatable fibrinolysis inhibitor (TAFI) and in understanding its molecular genetics, gene regulation, and biological roles”, Clinical Biochemistry 40 (2007) 431-442.

* cited by examiner

*Primary Examiner* — Tracy Vivlemore
(74) *Attorney, Agent, or Firm* — McCarter & English, LLP; Maria Laccotripe Zacharakis; Joseph A. Ciardi

(57) ABSTRACT

The present invention relates to RNAi agents, e.g., double stranded RNA (dsRNA) agents, targeting the CPB2 gene. The invention also relates to methods of using such RNAi agents to inhibit expression of a CPB2 gene and to methods of preventing and treating a CPB2-associated disorder, e.g., a disorder associated with thrombosis.

20 Claims, 4 Drawing Sheets

Specification includes a Sequence Listing.

CARBOXYPEPTIDASE B2 (CPB2) iRNA COMPOSITIONS AND METHODS OF USE THEREOF

RELATED APPLICATION

This application is a 35 § U.S.C. 111(a) continuation application which claims the benefit of priority to PCT/US2020/044398, filed on Jul. 31, 2020, which claims the benefit of priority to U.S. Provisional Patent Application No. 62/881,517, filed on Aug. 1, 2019. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jan. 14, 2022, is named 121301_09602_SL.txt and is 153,541 bytes in size.

BACKGROUND OF THE INVENTION

Carboxypeptidase B2 (CPB2, also known as thrombin-activated fibrinolysis inhibitor (TAFI)) plays an important role in the regulation of blood coagulation. CPB2 is a carboxypeptidase that removes C-terminal lysine binding sites for tissue-type plasminogen activator (tPA) and plasminogen from fibrin, decreasing the ability of fibrin to stimulate fibrinolysis. CPB2 is synthesized by the liver and circulates in the plasma as a plasminogen-bound zymogen. When it is activated by proteolysis at residue Arg92 by the thrombin/thrombomodulin complex, CPB2 exhibits carboxypeptidase activity. Activated CPB2 reduces fibrinolysis by removing the fibrin C-terminal residues that are important for the binding and activation of plasminogen, thus stimulating a blood clot to form and grow. Plasma CPB2 levels in Behcet's disease, a systemic vasculitis frequently complicated by arterial and venous thrombosis, were significantly higher than in healthy controls. Increased levels of CPB2 are also associated with increased risk of developing other disorders associated with thrombosis, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

Thrombosis is the formation of a blood clot within a blood vessel. It prevents blood from flowing normally through the circulatory system. When a blood clot forms in the veins, it is known as venous thromboembolism. This can cause deep vein thrombosis and pulmonary embolisms. When a clot forms in the arteries, it is called atherothrombosis, which can lead to heart attack and stroke.

The common treatment for thrombosis and is typically non-selective anti-coagulant therapy. Unfortunately, however, the lack of specificity of such therapies can lead to excessive bleeding. Accordingly, there is a need in the art for more effective treatments for disorders associated with thrombosis, e.g., plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

SUMMARY OF THE INVENTION

The present invention provides iRNA compositions which affect the RNA-induced silencing complex (RISC)-mediated cleavage of RNA transcripts of a gene encoding carboxypeptidase B2 (CPB2). The CPB2 may be within a cell, e.g., a cell within a subject, such as a human subject.

In an aspect, the invention provides a double stranded ribonucleic acid (dsRNA) agent for inhibiting expression of carboxypeptidase B2 (CPB2) in a cell, wherein the dsRNA agent comprises a sense strand and an antisense strand, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:2.

In another aspect, the invention provides a double stranded ribonucleic acid (dsRNA) agent for inhibiting expression of carboxypeptidase B2 (CPB2), wherein the dsRNA agent comprises a sense strand and an antisense strand forming a double stranded region, wherein the sense strand comprises at least 19 contiguous nucleotides from the nucleotide sequence of any one of nucleotides 92-114, 189-211, 322-344, 421-443, 662-684, 700-722, 753-755, 876-898, 965-987, 1080-1102, 1139-1161, or 1411-1433 of SEQ ID NO:1 and the antisense strand comprises at least 19 contiguous nucleotides from the corresponding nucleotide sequence of SEQ ID NO: 2.

In certain embodiments, the sense strand comprises at least 21 contiguous nucleotides of any one of nucleotides 92-114, 189-211, 322-344, 421-443, 662-684, 700-722, 753-755,876-898, 965-987, 1080-1102, 1139-1161, or 1411-1433 of SEQ ID NO: 1.

In certain embodiments, the antisense strand comprises at least 19 contiguous nucleotides from any one of the antisense strand nucleotide sequences of a duplex selected from the group consisting of AD-203386, AD-203800, AD-203564, AD-204014, AD-204103, AD-204191, AD-206384, AD-206596, AD-206944, AD-206997, AD-207367, AD-207600 and AD-329750. In certain embodiments, the sense strand comprises at least 19 contiguous nucleotides from any one of the sense strand nucleotide sequences of a duplex selected from the group consisting of AD-203386, AD-203800, AD-203564, AD-204014, AD-204103, AD-204191, AD-206384, AD-206596, AD-206944, AD-206997, AD-207367, AD-207600 and AD-329750. In certain embodiments, the sense and antisense strands comprise nucleotide sequences of a duplex selected from the group consisting of AD-203386, AD-203800, AD-203564, AD-204014, AD-204103, AD-204191, AD-206384, AD-206596, AD-206944, AD-206997, AD-207367, AD-207600 and AD-329750.

In certain embodiments, the dsRNA agent comprises at least one modified nucleotide. In certain embodiments, substantially all of the nucleotides of the sense strand and substantially all of the nucleotides of the antisense strand comprise a modification. In certain embodiments, all of the nucleotides of the sense strand and all of the nucleotides of the antisense strand comprise a modification. In certain embodiments, at least one of the modified nucleotides is selected from the group of a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, a nucleotide comprising a 5'-phosphate mimic, a thermally destabilizing nucleotide, a glycol modified nucleotide (GNA), and a 2-O—(N-methylacetamide) modified nucleotide; and combinations thereof. In certain embodiments, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, GNA, and combinations thereof. In certain embodiments, the modifications on the nucleotides are 2'-O-methyl or 2'-fluoro modifications. In certain embodiments, at least one of the modified nucleotides is selected from the group consisting of a deoxy-nucleotide, a 2'-O-methyl modified nucleotide, a 2'-fluoro modified nucleotide, a 2'-deoxy-modified nucleotide, a glycol modified nucleotide (GNA), and a 2-O—(N-methylacetamide) modified nucleotide; and combinations thereof. In certain embodiments, at least one of the nucleotide modifications is a thermally destabilizing nucleotide modification. In certain embodiments, the thermally destabilizing nucleotide modification is selected from the group consisting of an abasic modification; a mismatch with the opposing nucleotide in the duplex; and destabilizing sugar modification, a 2'-deoxy modification, an acyclic nucleotide, an unlocked nucleic acid (UNA), and a glycerol nucleic acid (GNA)

In certain embodiments, the double stranded region is 19-30 nucleotides in length. In certain embodiments, the double stranded region is 19-25 nucleotides in length. In certain embodiments, the double stranded region is 23-27 nucleotides in length. In certain embodiments, the double stranded region is 21-23 nucleotides in length. In certain embodiments, each strand of the dsRNA agent is independently no more than 30 nucleotides in length. In certain embodiments, at least one strand of the dsRNA agent comprises a 3' overhang of at least 1 nucleotide or at least 2 nucleotides.

In certain embodiments, dsRNA agent further comprises a ligand. In certain embodiments, the ligand is conjugated to the 3' end of the sense strand of the dsRNA agent. In certain embodiments, the ligand is one or more GalNAc derivatives attached through a monovalent, bivalent, or trivalent branched linker. In certain embodiments, the ligand is an N-acetylgalactosamine (GalNAc) derivative, e.g., wherein the ligand is

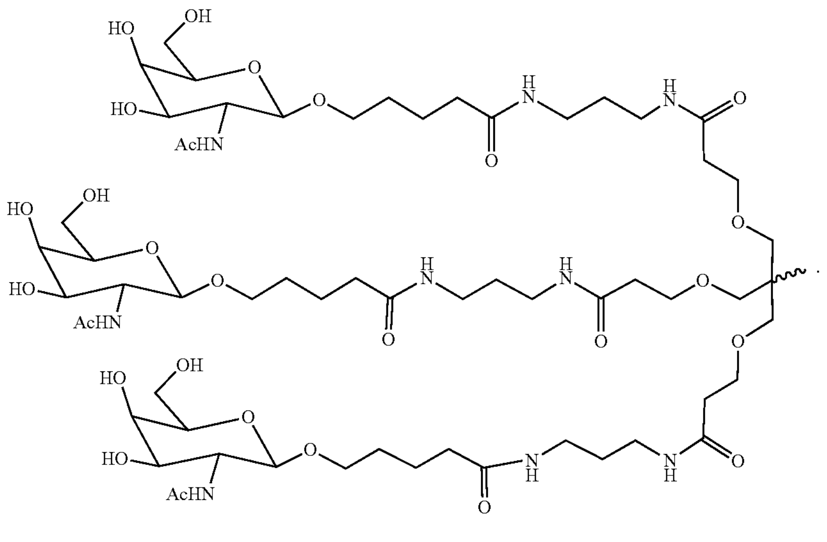 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In certain embodiments, the dsRNA agent is conjugated to the ligand as shown in the following schematic

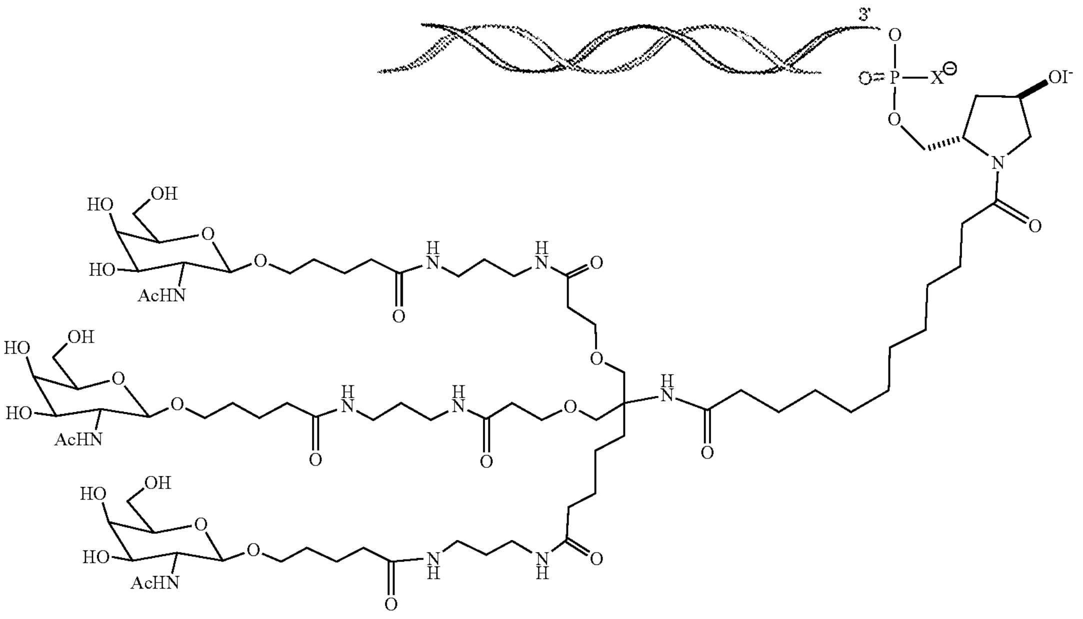

and, wherein X is O or S, e.g., wherein the X is O.

In certain embodiments, the dsRNA agent further comprises at least one phosphorothioate or methylphosphonate internucleotide linkage. In certain embodiments, the phosphorothioate or methylphosphonate internucleotide linkage is at the 3'-terminus of one strand. In certain embodiments, the strand is the antisense strand. In certain embodiments, the strand is the sense strand. In certain embodiments, the phosphorothioate or methylphosphonate internucleotide linkage is at the 5'-terminus of one strand. In certain embodiments, the strand is the antisense strand. In certain embodiments, the strand is the sense strand. In certain embodiments, the phosphorothioate or methylphosphonate internucleotide linkage is at the both the 5'- and 3'-terminus of one strand. In certain embodiments, the strand is the antisense strand.

In certain embodiments, the dsRNA agent at the 1 position of the 5'-end of the antisense strand of the duplex comprises a base pair that is an AU base pair.

In certain embodiments, the sense strand of the dsRNA agent comprises 5'-CUACAGAAUCUUACUACAACA-3' (SEQ ID NO: 9), and the antisense strand of the dsRNA agent comprises 5'-UGUUGUAGUAAGAUUCUGUAGAA-3' (SEQ ID NO: 10). In certain embodiments, the sense strand comprises 5'-csusacagAfaUfCfUfuacuacaaca-3' (SEQ ID NO: 11), and the antisense strand comprises 5'-VPusGfsuugUfaGfUfaagaUfuCfuguagsasa-3' (SEQ ID NO: 12), wherein a, g, c, and u are 2'-O-methyl (2'-OMe) A, G, C, and U; Af, Gf, Cf, and Uf are 2'-fluoro A, G, C, U; s is a phosphorothioate linkage, and VP is vinyl-phosphonate. In certain embodiments, the sense strand consists of 5'-csusacagAfaUfCfUfuacuacaacaL96-3' (SEQ ID NO: 13), and the antisense strand consists of 5'-VPusGfsuugUfaGfUfaagaUfuCfuguagsasa-3' (SEQ ID NO: 14), wherein a, g, c, and u are 2'-O-methyl (2'-OMe) A, G, C, and U; Af, Gf, Cf, and Uf are 2'-fluoro A, G, C, U; s is a phosphorothioate linkage, L96 is N-[tris(GalNAc-alkyl)-amidodecanoyl)]-4-hydroxyprolinol, and VP is vinyl-phosphonate.

In certain embodiments, the sense strand of the dsRNA agent comprises 5'-CUACAGAAUCUUACUACAACA-3' (SEQ ID NO: 15), and the antisense strand of the dsRNA agent comprises 5'-UGUUGUAGUAAGAUUCUGUAGAA-3' (SEQ ID NO: 16). In certain embodiments, the sense strand comprises 5'-csusacagAfaUfCfUfuacuacaacaL96-3' (SEQ ID NO: 17), and the antisense strand comprises 5'-usGfsuugUfaGfUfaagaUfuCfuguagsasa-3' (SEQ ID NO: 18), wherein a, g, c, and u are 2'-O-methyl (2'-OMe) A, G, C, and U; Af, Gf, Cf, and Uf are 2'-fluoro A, G, C, U; s is a phosphorothioate linkage, and VP is vinyl-phosphonate. In certain embodiments, the sense strand consists of 5'-csusacagAfaUfCfUfuacuacaacaL96-3' (SEQ ID NO: 19), and the antisense strand consists of 5'-usGfsuugUfaGfUfaagaUfuCfuguagsasa-3' (SEQ ID NO: 20), wherein a, g, c, and u are 2'-O-methyl (2'-OMe) A, G, C, and U; Af, Gf, Cf, and Uf are 2'-fluoro A, G, C, U; s is a phosphorothioate linkage, L96 is N-[tris(GalNAc-alkyl)-amidodecanoyl)]-4-hydroxyprolinol, and VP is vinyl-phosphonate.

In another aspect, the invention provides a double stranded ribonucleic acid (dsRNA) agent for inhibiting expression of CPB2, wherein the dsRNA agent comprises a sense strand and an antisense strand, wherein the sense strand consists of the nucleotide sequence of 5'-csusacagAfaUfCfUfuacuacaaca-3' (SEQ ID NO: 21) and the antisense strand consists of the nucleotide sequence of 5'-VPusGfsuugUfaGfUfaagaUfuCfuguagsasa (SEQ ID NO: 22)-3' (SEQ ID NO:), wherein a, g, c, and u are 2'-O-methyl (2'-OMe) A, G, C, and U; Af, Gf, Cf, and Uf are 2'-fluoro A, G, C, U; s is a phosphorothioate linkage, VP is vinyl-phosphonate, and wherein a ligand is conjugated to the 3' end of the sense strand, and wherein the ligand has the following structure:

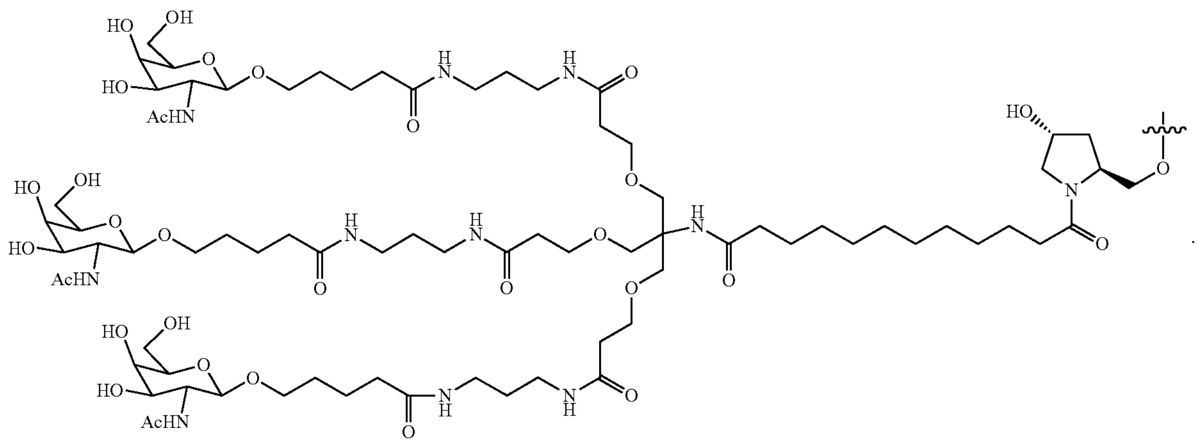

.

In certain embodiments, the sense strand of the dsRNA agent comprises 5'-CUACAGAAUCUUACUACAACA-3' (SEQ ID NO: 23), and the antisense strand of the dsRNA agent comprises 5'-UGUUGUAGUAAGAUUCUGUAGAA-3' (SEQ ID NO: 24). In certain embodiments, the sense strand comprises 5'-csusacagAfaUfCfUfuacuacaaca-3' (SEQ ID NO: 25), and the antisense strand comprises 5'-usGfsuugUfaGfUfaagaUfuCfuguagsasa-3' (SEQ ID NO: 26), wherein a, g, c, and u are 2'-O-methyl (2'-OMe) A, G, C, and U; Af, Gf, Cf, and Uf are 2'-fluoro A, G, C, U; s is a phosphorothioate linkage, and wherein a ligand is conjugated to the 3' end of the sense strand, and wherein the ligand has the following structure:

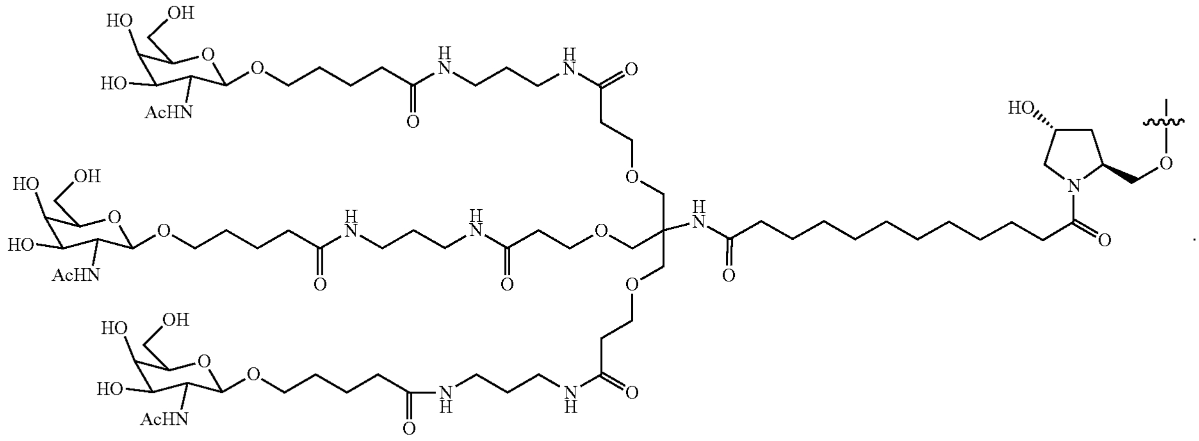

.

In certain embodiments, the sense strand consists of 5'-csusacagAfaUfCfUfuacuacaaca-3' (SEQ ID NO: 27), and the antisense strand consists of 5'-usGfsuugUfaGfUfaagaUfuCfuguagsasa-3' (SEQ ID NO: 28), wherein a, g, c, and u are 2'-O-methyl (2'-OMe) A, G, C, and U; Af, Gf, Cf, and Uf are 2'-fluoro A, G, C, U; s is a phosphorothioate linkage, and wherein a ligand is conjugated to the 3' end of the sense strand, and wherein the ligand has the following structure:

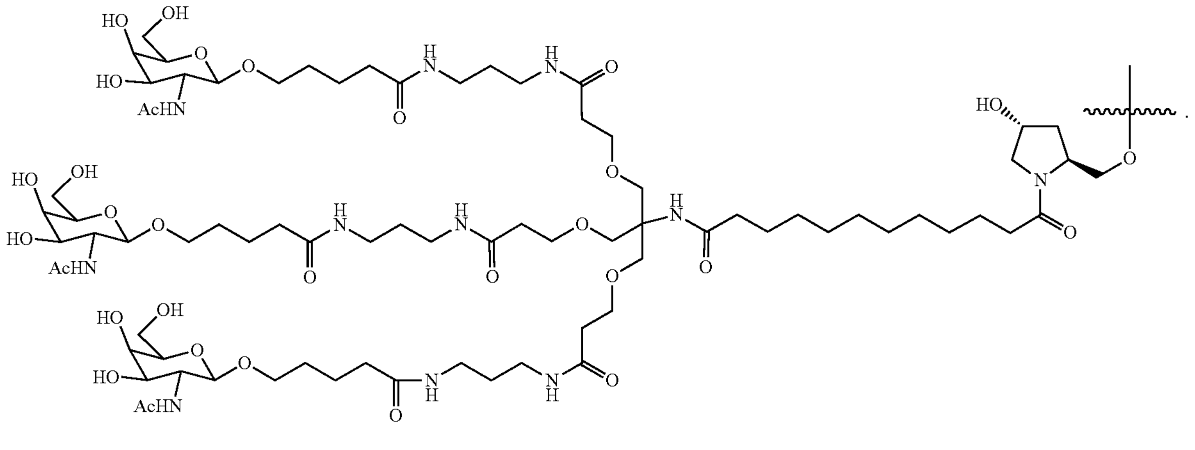 [SMILES: *OC[C@@H]1C[C@@H](O)CN1C(=O)CCCCCCCCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

In a further aspect, the invention provides a cell containing the dsRNA agents of the invention.

In yet another aspect, the invention provides a pharmaceutical composition for inhibiting expression of a gene encoding CPB2 comprising the dsRNA agents of the invention.

In another aspect, the invention provides a method of inhibiting expression of a CPB2 gene in a cell. The method includes contacting the cell with the dsRNA agent or a pharmaceutical composition of the invention, thereby inhibiting expression of the CPB2 gene in the cell. In certain embodiments, the cell is within a subject. In certain embodiments, the subject is a human. In certain embodiments, the subject has been diagnosed with a CPB2-associated disorder.

In certain embodiments, the CPB2-associated disorder is a disorder associated with thrombosis, e.g., plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

In certain embodiments, contacting the cell with the dsRNA agent inhibits the expression of CPB2 by at least 50%, 60%, 70%, 80%, 90%, or 95% (e.g., as compared to the level of expression of CPB2 prior to first contacting the cell with the dsRNA agent; e.g., prior to administration of a first dose of the dsRNA agent to the subject). In certain embodiments, inhibiting expression of CPB2 decreases a CPB2 protein level in a subject serum sample(s) by at least 50%, 60%, 70%, 80%, 90%, or 95%, e.g., as compared to the level of expression of CPB2 prior to first contacting the cell with the dsRNA agent.

In an aspect, the invention provides a method of treating a CPB2-associated disorder in a subject. The method includes administering to the subject the dsRNA agent or the pharmaceutical composition of the invention, thereby treating the CPB2-associated disorder in the subject. In certain embodiments, the subject is human.

In certain embodiments of the invention, the dsRNA agent is administered at a dose of about 0.01 mg/kg to about 50 mg/kg. In certain embodiments, the dsRNA agent is administered to the subject subcutaneously. In certain embodiments, the level of CPB2 is measured in the subject. In certain embodiments, the level of CPB2 in the subject is a CPB2 protein level in a subject blood or serum sample.

In certain embodiments, an additional therapeutic agent for treatment of a CPB2-associated disorder is administered to the subject. In certain embodiments, the additional therapeutic agent is an anticoagulant. In some embodiments, the anticoagulant includes heparin, enoxaparin (Lovenox), dalteparin (Fragmin), fondaparinux (Arixtra), warfarin (Coumadin, Jantoven), dabigatran (Pradaxa), rivaroxaban (Xarelto), apixaban (Eliquis), edoxaban (Savaysa), argatroban or any combination thereof. In some embodiments, the additional therapeutic agent includes a thrombolytic. In certain embodiments, the thrombolytic includes antistreplase (Eminase), tissue plasminogen activator (tPA), urokinase-type plasminogen activator (uPA), or any combination thereof. In some embodiments, the additional therapeutic agent is an immunosuppressant. In certain embodiments, the immunosuppresant includes corticosteroid, azathioprine, cyclosporine A, or any combination thereof. In some embodiments, the additional therapeutic agent is hormone replacement therapy. In certain embodiments, the hormone replacement therapy includes estrogen, gestagen, androgen or any combination thereof. In some embodiments, the additional therapeutic agent is an antibiotic. In some embodiments, the additional therapeutic agent is an antihistamine agent. In some embodiments, the additional therapeutic agent is an mast cell stablizer. In certain embodiments, the mast cell stabilizer includes cromoglicic acid (Cromolyn), lodoxamide (Alomide), or any combination thereof. In some embodiments, the additional therapeutic agent is an anti-proliferative agent. In some embodiments, the additional therapeutic agent is an oral contraceptive. In some embodiments, the additional therapeutic agent is a fresh frozen plasma or a plasminogen concentrate. In some embodiments, the additional therapeutic agent is hyaluronidase. In some embodiments, the additional therapeutic agent is alpha chymotrypsin. In certain embodiments, the additional therapeutic agent is a filter inserted into a large vein that prevents clots that break loose from lodging in the patient's lungs. In certain embodiments, the additional therapeutic agent is selected from the group consisting of an anticoagulant, a CPB2 inhibitor, a thrombin inhibitor.

The invention also provides uses of the dsRNA agents and the pharmaceutical compositions provided herein for treatment of a CPB2-associated disorder. In certain embodiments, the uses include any of the methods provided by the invention.

The invention provides kits comprising a dsRNA agent of the invention. In certain embodiments, the invention provides kits for practicing a method of the invention.

DETAILED DESCRIPTION OF THE INVENTION

Figure 1:
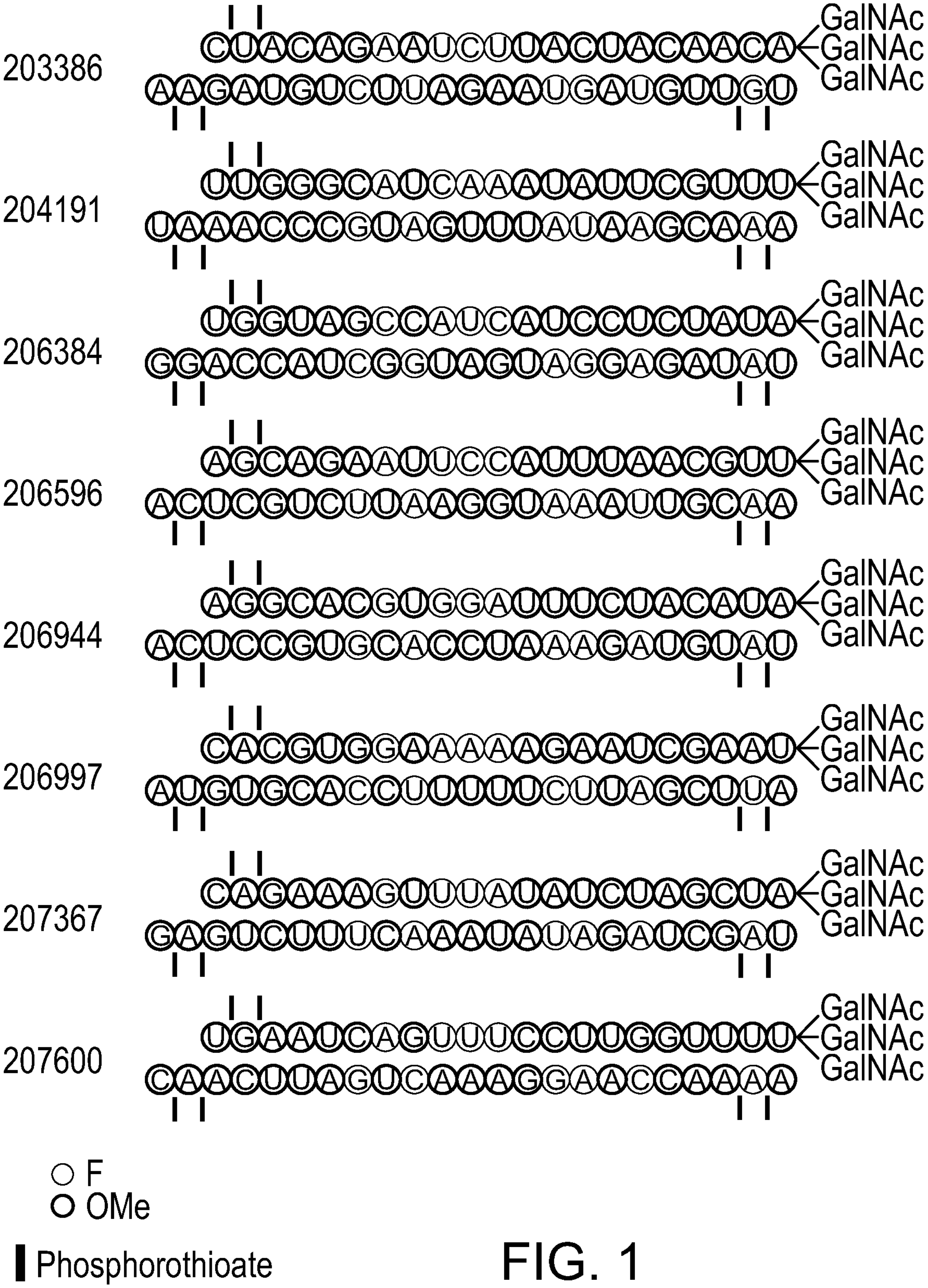
FIG. 1 schematically depicts the nucleotide sequences of dsRNA duplexes targeting CPB2 that were subcutaneoulsy administered to mice (n=3 per group) as a single 2 mg/kg dose (SEQ ID NOs 517-532, respectively, in order of appearance).

The present invention provides iRNA compositions which effect the RNA-induced silencing complex (RISC)-mediated cleavage of RNA transcripts of a CPB2 gene. The gene may be within a cell, e.g., a cell within a subject, such as a human. The use of these iRNAs enables the targeted degradation of mRNAs of the corresponding gene (CPB2 gene) in mammals.

The iRNAs of the invention have been designed to target the human CPB2 gene, including portions of the gene that are conserved in the CPB2 orthologs of other mammalian species. Without intending to be limited by theory, it is believed that a combination or sub-combination of the foregoing properties and the specific target sites or the specific modifications in these iRNAs confer to the iRNAs of the invention improved efficacy, stability, potency, durability, and safety.

Accordingly, the present invention provides methods for treating and preventing a CPB2-associated disorder, e.g., a disorder associated with thrombosis, using iRNA compositions which effect the RNA-induced silencing complex (RISC)-mediated cleavage of RNA transcripts of a CPB2 gene.

The iRNAs of the invention include an RNA strand (the antisense strand) having a region which is up to about 30 nucleotides or less in length, e.g., 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of a CPB2 gene.

In certain embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of a CPB2 gene. In some embodiments, such iRNA agents having longer length antisense strands preferably may include a second RNA strand (the sense strand) of 20-60 nucleotides in length wherein the sense and antisense strands form a duplex of 18-30 contiguous nucleotides.

The use of iRNAs of the invention enables the targeted degradation of mRNAs of the corresponding gene (CPB2 gene) in mammals. Using in vitro and in vivo assays, the present inventors have demonstrated that iRNAs targeting a CPB2 gene can mediate RNAi, resulting in significant inhibition of expression of CPB2. Inhibition of expression of CPB2 in such a subject will prevent or treat development of a CPB2-associated disorder, e.g., a disorder associated with thrombosis. Thus, methods and compositions including these iRNAs are useful for preventing and treating a subject susceptible to or diagnosed with a CPB2-associated disorder, e.g., a disorder associated with thrombosis, such as plasminogen deficiency. The methods and compositions herein are useful for reducing the level of CPB2 in a subject.

The following detailed description discloses how to make and use compositions containing iRNAs to inhibit the expression of a CPB2 gene as well as compositions, uses, and methods for treating subjects that would benefit from reduction of the expression of a CPB2 gene, e.g., subjects susceptible to or diagnosed with a CPB2-associated disorder, e.g., a disorder associated with thrombosis, such as plasminogen deficiency.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means±10%. In certain embodiments, about means±5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 19 nucleotides of a 21 nucleotide nucleic acid molecule" means that 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

In the event of a conflict between a sequence and its indicated site on a transcript or other sequence, the nucleotide sequence recited in the specification takes precedence.

As used herein, "carboxypeptidase B2," used interchangeably with the term "CPB2" refers to the well-known gene and polypeptide, also known in the art as thrombin-activated fibrinolysis inhibitor (TAFI). The term "CPB2" is used interchangeably with the term "TAFI" herein.

The term "CPB2" includes human CPB2, the amino acid and complete coding sequence of which may be found in for example, GenBank Accession No. GI:1519246320 (NM_001872.5; SEQ ID NO:1); *Macaca fascicularis* CPB2, the amino acid and complete coding sequence of which may be found in for example, GenBank Accession No. GI: 544503641 (XM_005585800.1: SEQ ID NO: 3); mouse (*Mus musculus*) CPB2, the amino acid and complete coding sequence of which may be found in for example, GenBank Accession No. GI: 255958287 (NM_0019775.3; SEQ ID NO:5); and rat CPB2 (*Rattus norvegicus*) CPB2 the amino acid and complete coding sequence of which may be found in for example, for example GenBank Accession No. GI: 162287185 (NM_053617.2; SEQ ID NO: 7).

Additional examples of CPB2 mRNA sequences are readily available using publicly available databases, e.g., GenBank, UniProt, OMIM, and the *Macaca* genome project web site.

The term "CPB2," as used herein, also refers to naturally occurring DNA sequence variations of the CPB2 gene, such as a single nucleotide polymorphism (SNP) in the CPB2 gene. Exemplary SNPs may be found in the dbSNP database available at ncbi.nlm.nih.gov/projects/SNP/snp_ref.cgi?geneId=1361. Non-limiting examples of sequence variations within the CPB2 gene may include, for example, as a G→A at position −438 (relative to the transcription start site); a G→A at position +505 (A147T); a C→T at position +1040 (T325I); and/or an A→T at position +1583 (untranslated).

As used herein, "target sequence" refers to a contiguous portion of the nucleotide sequence of an mRNA molecule formed during the transcription of a CPB2 gene, including mRNA that is a product of RNA processing of a primary transcription product. The target portion of the sequence will be at least long enough to serve as a substrate for iRNA-directed cleavage at or near that portion of the nucleotide sequence of an mRNA molecule formed during the transcription of a CPB2 gene. In one embodiment, the target sequence is within the protein coding region of CPB2.

The target sequence may be from about 19-36 nucleotides in length, e.g., preferably about 19-30 nucleotides in length. For example, the target sequence can be about 19-30 nucleotides, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of a CPB2 gene in a cell, e.g., a cell within a subject, such as a mammalian subject.

In one embodiment, an RNAi agent of the invention includes a single stranded RNA that interacts with a target RNA sequence, e.g., a CPB2 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a CPB2 gene. Accordingly, the term "siRNA" is also used herein to refer to an iRNA as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In certain embodiments, an "iRNA" for use in the compositions, uses, and methods of the invention is a double stranded RNA and is referred to herein as a "double stranded RNA agent," "double stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a CPB2 gene. In some embodiments of the invention, a double stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide or a modified nucleotide. In addition, as used in this specification, an "iRNA" may include ribonucleotides with chemical modifications; an iRNA may include substantial modifications at multiple nucleotides. As used herein, the term "modified nucleotide" refers to a nucleotide having, independently, a modified sugar moiety, a modified internucleotide linkage, or modified nucleobase, or any combination thereof. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "iRNA" or "RNAi agent" for the purposes of this specification and claims.

The duplex region may be of any length that permits specific degradation of a desired target RNA through a RISC pathway, and may range from about 19 to 36 base pairs in length, e.g., about 19-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, 3, 4, 5, 6, 7, 8, 9, 10, 20, 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not be, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In certain embodiments, an iRNA agent of the invention is a dsRNA, each strand of which comprises 19-23 nucleotides, that interacts with a target RNA sequence, e.g., a CPB2 gene, to direct cleavage of the target RNA.

In some embodiments, an iRNA of the invention is a dsRNA of 24-30 nucleotides that interacts with a target RNA sequence, e.g., a CPB2 target mRNA sequence, to direct the cleavage of the target RNA.

As used herein, the term "nucleotide overhang" refers to at least one unpaired nucleotide that protrudes from the duplex structure of a double stranded iRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of either an antisense or sense strand of a dsRNA.

In certain embodiments, the antisense strand of a dsRNA has a 1-10 nucleotide, e.g., a 1, 2, 3, 4, 5, 6, 7, 8, 9, or 10 nucleotide, overhang at the 3'-end or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, 10-25 nucleotides, 10-20 nucleotides, or 10-15 nucleotides in length. In certain embodiments, an extended overhang is on the sense strand of the duplex. In certain embodiments, an extended overhang is present on the 3' end of the sense strand of the duplex. In certain embodiments, an extended overhang is present on the 5' end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the extended overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNA agent, i.e., no nucleotide overhang. A "blunt ended" double stranded RNA agent is double stranded over its entire length, i.e., no nucleotide overhang at either end of the molecule. The RNAi agents of the invention include RNAi agents with no nucleotide overhang at one end (i.e., agents with one overhang and one blunt end) or with no nucleotide overhangs at either end. Most often such a molecule will be double-stranded over its entire length.

The term "antisense strand" or "guide strand" refers to the strand of an iRNA, e.g., a dsRNA, which includes a region that is substantially complementary to a target sequence, e.g., a CPB2 mRNA. As used herein, the term "region of complementarity" refers to the region on the antisense strand that is substantially complementary to a sequence, for example a target sequence, e.g., a CPB2 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, or 3 nucleotides of the 5'- or 3'-end of the iRNA. In some embodiments, a double stranded RNA agent of the invention includes a nucleotide mismatch in the antisense strand. In some embodiments, a double stranded RNA agent of the invention includes a nucleotide mismatch in the sense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA.

The term "sense strand" or "passenger strand" as used herein, refers to the strand of an iRNA that includes a region that is substantially complementary to a region of the antisense strand as that term is defined herein.

As used herein, "substantially all of the nucleotides are modified" are largely but not wholly modified and can include not more than 5, 4, 3, 2, or 1 unmodified nucleotides.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3, or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of a double stranded RNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a CPB2 gene). For example, a polynucleotide is complementary to at least a part of a CPB2 mRNA if the sequence is substantially complementary to a non-interrupted portion of an mRNA encoding a CPB2 gene.

Accordingly, in some embodiments, the sense strand polynucleotides and the antisense polynucleotides disclosed herein are fully complementary to the target CPB2 sequence. In other embodiments, the sense strand polynucleotides or the antisense polynucleotides disclosed herein are substantially complementary to the target CPB2 sequence and comprise a contiguous nucleotide sequence which is at least 80% complementary over its entire length to the equivalent region of the nucleotide sequence of any one of SEQ ID NOs:1 and 2, or a fragment of any one of SEQ ID NOs:1 and 2, such as at least 90%, or 95% complementary; or 100% complementary.

Accordingly, in some embodiments, the antisense strand polynucleotides disclosed herein are fully complementary to the target CPB2 sequence. In other embodiments, the antisense strand polynucleotides disclosed herein are substantially complementary to the target CPB2 sequence and comprise a contiguous nucleotide sequence which is at least about 90% complementary over its entire length to the equivalent region of the nucleotide sequence of SEQ ID NO:1, or a fragment of SEQ ID NO:1, such as about 90%, or about 95%, complementary. In certain embodiments, the fragment of SEQ ID NO: 1 is selected from the group of nucleotides 632-658, 635-658, 636-658, 1248-1273, 1248-1270, 1250-1272, 1251-1273, 1580-1602, 1584-1606, 1587-1609, 1601-1623, 1881-1903, 2074-2097, 2074-2096, 2075-2097, 2080-2102, 2272-2294, 2276-2298, 2281-2304, 2281-2303, or 2282-2304 of SEQ ID NO: 1.

In some embodiments, an iRNA of the invention includes an antisense strand that is substantially complementary to the target CPB2 sequence and comprises a contiguous nucleotide sequence which is at least about 90% complementary over its entire length to the equivalent region of the nucleotide sequence of any one of the sense strands in Table 2, or Table 3 or a fragment of any one of the sense strands in Table 2, or Table 3, such as about 90%, 95%, or 100% complementary.

In some embodiments, an iRNA of the invention includes a sense strand that is substantially complementary to an antisense polynucleotide which, in turn, is complementary to a target CPB2 sequence, and wherein the sense strand polynucleotide comprises a contiguous nucleotide sequence which is at least about 90% complementary over its entire length to the equivalent region of the nucleotide sequence of any one of the antisense strands in Table 2 or 3, or a fragment of any one of the antisense strands in Table 2 or 3, such as about 90%, 95%, or 100%.

In certain embodiments, the sense and antisense strands in Table 2 or Table 3 are selected from duplexes AD-203386, AD-203800, AD-203564, AD-204014, AD-204103, AD-204191, AD-206384, AD-206596, AD-206944, AD-206997, AD-207367, AD-207600 and AD-329750.

In general, an "iRNA" includes ribonucleotides with chemical modifications. Such modifications may include all types of modifications disclosed herein or known in the art. Any such modifications, as used in a dsRNA molecule, are encompassed by "iRNA" for the purposes of this specification and claims.

In an aspect of the invention, an agent for use in the methods and compositions of the invention is a single-stranded antisense oligonucleotide molecule that inhibits a target mRNA via an antisense inhibition mechanism. The single-stranded antisense oligonucleotide molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense oligonucleotide molecule may be about 14 to about 30 nucleotides in length and have a sequence that is complementary to a target sequence. For example, the single-stranded antisense oligonucleotide molecule may comprise a sequence that is at least about 14, 15, 16, 17, 18, 19, 20, or more contiguous nucleotides from any one of the antisense sequences described herein.

The phrase "contacting a cell with an iRNA," such as a dsRNA, as used herein, includes contacting a cell by any possible means. Contacting a cell with an iRNA includes contacting a cell in vitro with the iRNA or contacting a cell in vivo with the iRNA. The contacting may be done directly or indirectly. Thus, for example, the iRNA may be put into physical contact with the cell by the individual performing the method, or alternatively, the iRNA may be put into a situation that will permit or cause it to subsequently come into contact with the cell.

Contacting a cell in vitro may be done, for example, by incubating the cell with the iRNA. Contacting a cell in vivo may be done, for example, by injecting the iRNA into or near the tissue where the cell is located, or by injecting the iRNA into another area, e.g., the bloodstream or the subcutaneous space, such that the agent will subsequently reach the tissue where the cell to be contacted is located. For example, the iRNA may contain or be coupled to a ligand, e.g., GalNAc, that directs the iRNA to a site of interest, e.g., the liver. Combinations of in vitro and in vivo methods of contacting are also possible. For example, a cell may also be contacted in vitro with an iRNA and subsequently transplanted into a subject.

In certain embodiments, contacting a cell with an iRNA includes "introducing" or "delivering the iRNA into the cell" by facilitating or effecting uptake or absorption into the cell. Absorption or uptake of an iRNA can occur through unaided diffusion or active cellular processes, or by auxiliary agents or devices. Introducing an iRNA into a cell may be in vitro or in vivo. For example, for in vivo introduction, iRNA can be injected into a tissue site or administered systemically. In vitro introduction into a cell includes methods known in the art such as electroporation and lipofection. Further approaches are described herein below or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a horse, a goat, a rabbit, a sheep, a hamster, a guinea pig, a cat, a dog, a rat, or a mouse), or a bird that expresses the target gene, either endogenously or heterologously. In an embodiment, the subject is a human, such as a human being treated or assessed for a disease or disorder that would benefit from reduction in CPB2 expression; a human at risk for a disease or disorder that would benefit from reduction in CPB2 expression; a human having a disease or disorder that would benefit from reduction in CPB2 expression; or human being treated for a disease or disorder that would benefit from reduction in CPB2 expression as described herein. The diagnostic criteria for a CPB2-associated disorder, e.g., a disorder associated with thrombosis e.g., plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke, are provided below.

In some embodiments, the subject is a female human. In other embodiments, the subject is a male human. In certain embodiments, the subject is overweight or obese, e.g., a subject that suffers from central obesity. In certain embodiments, the subject is sedentary. In certain embodiments, the subject is pregnant.

As used herein, the terms "treating" or "treatment" refer to a beneficial or desired result, such as reducing at least one sign or symptom of a CPB2-associated disorder, e.g., thrombosis or deposits of fibrin-rich "pseudomembranes" (woody or ligneous membranes) that impair normal tissue and organ function, e.g., ligneous conjunctivitis, i.e., peudomembranes or ligneous lesions that affect the eyes; or ligneous lesions that affect the gingiva, oropharynx, middle ear, renal collecting system, respiratory tract, central nervous system, skin, and female reproductive tract in a subject. Treatment also includes a reduction of one or more sign or symptoms associated with unwanted CPB2 expression, e.g., stabilization of active CPB2; diminishing the extent of unwanted CPB2 activation or stabilization; amelioration or palliation of unwanted CPB2 activation or stabilization. "Treatment" can also mean prolonging survival as compared to expected survival in the absence of treatment. Non-limiting examples of CPB2-associated diseases or disorders include, plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

The term "lower" in the context of the level of CPB2 gene expression or CPB2 protein production in a subject, or a disease marker or symptom refers to a statistically significant decrease in such level. The decrease can be, for example, at least 50%, 55%, 60%, 65%, 70%, 75%, 80%, 85%, 90%, or 95%, or below the level of detection for the detection method in a relevant cell or tissue, e.g., a liver cell or tissue, an eye cell or tissue, or other subject sample, e.g., blood or serum derived therefrom, urine.

As used herein, "prevention" or "preventing," when used in reference to a disease or disorder, that would benefit from a reduction in expression of a CPB2 gene or production of CPB2 protein, e.g., in a subject susceptible to a CPB2-associated disorder due to, e.g., aging, genetic factors, such as plasminogen deficiency, hormone changes, diet, and a sedentary lifestyle. In certain embodiments, the disease or disorder is e.g., a symptom of unwanted CPB2 activation or stabilization, such as a thrombosis, e.g., venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke. The likelihood of developing, e.g., thrombosis, is reduced, for example, when an individual having one or more risk factors for a thrombosis either fails to develop thrombosis or develops thrombosis with less severity relative to a population having the same risk factors and not receiving treatment as described herein. The failure to develop a CPB2-associated disorder, e.g., thrombosis or a delay in the time to develop thrombosis by months or years is considered effective prevention. Prevention may require administration of more than one dose if the iRNA agent.

As used herein, the term "carboxypeptidase B2-associated disease" or "CPB2-associated disease," is a disease or disorder that would benefit from reduction in CPB2 expression, e.g., a blood clotting disorder, e.g., by inhibing CPB2 expression, CPB2 is unable to reduce fibrinolysis by removing the fibrin C-terminal residues that are important for the binding and activation of plasminogen, thus inhibiting a blood clot from forming and growing. In some embodiments, the CPB2-associated disease or disorder is a disease or disorder associated with thrombosis. Non-limiting examples of carboxypeptidase B2-associated diseases include, plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

In one embodiment, a carboxypeptidase B2-associated disease is plasminogen deficiency. Plasminogen deficiency is a disorder that results in development of fibrin-rich "pseudomembranes" that impair normal tissue and organ function. Plasminogen deficiency is an inherited clotting disorder caused by mutations in the PLG gene, which encodes plasminogen. Normally, plasminogen is converted by plasminogen activator into plasmin, which breaks down fibrin. Fibrin is the main protein involved in blood clots and is important for wound healing, creating the framework for normal tissue to grow back. Normally, excess fibrin is broken down when no longer needed, and the new, more flexible normal tissue takes its place.

Mutations in the PLG gene can decrease the amount of plasminogen that is produced, its function, or both. When the mutations affect plasminogen levels as well as the activity of the protein, affected individuals are said to have type I plasminogen deficiency or hypoplasminogenemia. Subjects with mutations that result in normal levels of plasminogen with reduced activity are said to have type II congenital plasminogen deficiency or dysplasminogenemia.

A reduction in functional plasminogen results in less plasmin to break down fibrin, leading to a buildup of fibrin. The excess fibrin and the resulting inflammation of the tissue result in the inflamed woody growths on the mucous membranes. The most common symptom of this disorder is ligneous conjunctivitis. This occurs when a buildup of fibrin causes inflammation of the conjunctiva, which are the mucous membranes that protect the white part of the eye (the sclera) and line the eyelids, leading to thick, woody (ligneous), inflamed growths. These growths can lead to tearing of the cornea, scarring, and vision loss. Other physiologic systems are affected including the gingiva, oropharynx, middle ear, renal collecting system, respiratory tract, central nervous system, skin, and female reproductive tract.

This excess fibrin and reduced fibrinolysis in subjects having plasminogen deficiency are associated with an increased thrombotic tendency or development of abnormal clots in the blood vessels, e.g., the veins, and include thrombophlebitis (red inflamed veins), pulmonary embolism, and stroke.

In one embodiment, a carboxypeptidase B2-associated disease is post-thrombotic syndrome. "Post-thrombotic syndrome" or "PTS" is a chronic complication of deep venous thrombosis (DVT), which includes symptoms and signs of chronic venous insufficiency that develop following DVT. A combination of reflux due to valvular incompetence and venous hypertension due to thrombotic obstruction is thought to underlie the pathophysiology of PST. Symptoms and signs of post-thrombotic syndrome may include leg pain, leg heaviness, vein dilation, edema, skin pigmentation, and venous ulcers.

A "therapeutically-effective amount" or "prophylactically effective amount" also includes an amount of an RNAi agent that produces some desired effect at a reasonable benefit/risk ratio applicable to any treatment. The iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition, or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Such carriers are known in the art. Pharmaceutically acceptable carriers include carriers for administration by injection.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In certain embodiments, samples may be derived from the eye (e.g., the conjunctiva, the mucous membrane, the eyelid, the sclera, or certain types of cells in the eye, e.g., a ganglion cell, a bipolar neuron, a rod cell or a cone cell.) In some embodiments, a "sample derived from a subject" refers to urine obtained from the subject. A "sample derived from a subject" can refer to blood or blood derived serum or plasma from the subject.

II. iRNAs of the Invention

The present invention provides iRNAs which inhibit the expression of a CPB2 gene. In preferred embodiments, the iRNA includes double stranded ribonucleic acid (dsRNA) molecules for inhibiting the expression of a CPB2 gene in a cell, such as a cell within a subject, e.g., a mammal, such as a human susceptible to developing a CPB2-associated disorder, e.g., a disorder associated with thrombosis, such as plasminogen deficiency. The dsRNAi agent includes an antisense strand having a region of complementarity which is complementary to at least a part of an mRNA formed in the expression of a CPB2 gene. The region of complementarity is about 19-30 nucleotides in length (e.g., about 30, 29, 28, 27, 26, 25, 24, 23, 22, 21, 20, or 19 nucleotides in length). Upon contact with a cell expressing the CPB2 gene, the iRNA inhibits the expression of the CPB2 gene (e.g., a human, a primate, a non-primate, or a rat CPB2 gene) by at least about 50% as assayed by, for example, a PCR or branched DNA (bDNA)-based method, or by a protein-based method, such as by immunofluorescence analysis, using, for example, western blotting or flow cytometric techniques. In preferred embodiments, inhibition of expression is determined by the qPCR method provided in the examples, especially in Example 2 with the siRNA at a 10 nM concentration in an appropriate organism cell line provided therein. In preferred embodiments, inhibition of expression in vivo is determined by knockdown of the human gene in a rodent expressing the human gene, e.g., a mouse or an AAV-infected mouse expressing the human target gene, e.g., when administered a single dose at 3 mg/kg at the nadir of RNA expression. RNA expression in liver is determined using the PCR methods provided in Example 2.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a CPB2 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 19 to 30 base pairs in length. Similarly, the region of complementarity to the target sequence is 19 to 30 nucleotides in length.

In some embodiments, the dsRNA is about 19 to about 23 nucleotides in length, or about 25 to about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 19 to about 30 base pairs, e.g., about 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target CPB2 gene expression is not generated in the target cell by cleavage of a larger dsRNA.

A dsRNA as described herein can further include one or more single-stranded nucleotide overhangs e.g., 1-4, 2-4, 1-3, 2-3, 1, 2, 3, or 4 nucleotides. dsRNAs having at least one nucleotide overhang can have superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand, or any combination thereof. Furthermore, the nucleotide(s) of an overhang can be present on the 5'-end, 3'-end, or both ends of an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In an aspect, a dsRNA of the invention includes at least two nucleotide sequences, a sense sequence and an antisense sequence. The sense strand is selected from the group of sequences provided in Tables 2 and 3, and the corresponding antisense strand of the sense strand is selected from the group of sequences of Tables 2 and 3. In this aspect, one of the two sequences is complementary to the other of the two sequences, with one of the sequences being substantially complementary to a sequence of an mRNA generated in the expression of a CPB2 gene. As such, in this aspect, a dsRNA will include two oligonucleotides, where one oligonucleotide is described as the sense strand in Table 2 or 3, and the second oligonucleotide is described as the corresponding antisense strand of the sense strand in Table 2 or 3. In certain embodiments, the substantially complementary sequences of the dsRNA are contained on separate oligonucleotides. In other embodiments, the substantially complementary sequences of the dsRNA are contained on a single oligonucleotide. In certain embodiments, the sense or antisense strand from Table 2 or 3 is selected from AD-203386, AD-203800, AD-203564, AD-204014, AD-204103, AD-204191, AD-206384, AD-206596, AD-206944, AD-206997, AD-207367, AD-207600 and AD-329750.

It will be understood that, although the sequences in Table 2 are not described as modified or conjugated sequences, the RNA of the iRNA of the invention e.g., a dsRNA of the invention, may comprise any one of the sequences set forth in Table 2, or the sequences of Table 3 that are modified, or the sequences of Table 3 that are conjugated. In other words, the invention encompasses dsRNA of Tables 2 and 3 which are un-modified, un-conjugated, modified, or conjugated, as described herein.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 2 and 3, dsRNAs described herein can include at least one strand of a length of minimally 21 nucleotides. It can be reasonably expected that shorter duplexes having one of the sequences of Tables 2 and 3 minus only a few nucleotides on one or both ends can be similarly effective as compared to the dsRNAs described above. Hence, dsRNAs having a sequence of at least 19, 20, or more contiguous nucleotides derived from one of the sequences of Tables 2 and 3, and differing in their ability to inhibit the expression of a CPB2 gene by not more than about 5, 10, 15, 20, 25, or 30% inhibition from a dsRNA comprising the full sequence, are contemplated to be within the scope of the present invention.

In addition, the RNAs provided in Tables 2 and 3 identify a site(s) in a CPB2 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 19 contiguous nucleotides from one of the sequences provided in Tables 2 and 3 coupled to additional nucleotide sequences taken from the region contiguous to the selected sequence in a CPB2 gene.

III. Modified iRNAs of the Invention

In certain embodiments, the RNA of the iRNA of the invention e.g., a dsRNA, is un-modified, and does not comprise, e.g., chemical modifications or conjugations known in the art and described herein. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA or substantially all of the nucleotides of an iRNA are modified, i.e., not more than 5, 4, 3, 2, or 1 unmodified nucleotides are present in a strand of the iRNA.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. Patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. Patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Suitable RNA mimetics are contemplated for use in iRNAs provided herein, in which both the sugar and the internucleoside linkage, i.e., the backbone, of the nucleotide units are replaced with novel groups. The base units are maintained for hybridization with an appropriate nucleic acid target compound. One such oligomeric compound in which an RNA mimetic that has been shown to have excellent hybridization properties is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O—, S—, or N-alkyl; O—, S-, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. Patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

In some embodiments, the RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-($CH_2$)—O-2' (LNA); 4'-($CH_2$)—S-2'; 4'—($CH_2$)2-O-2' (ENA); 4'-CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845); 4'-C($CH_3$)($CH_3$)—O-2' (and analogs thereof; see e.g., U.S. Pat. No. 8,278,283); 4'-$CH_2$—N($OCH_3$)-2' (and analogs thereof; see e.g., U.S. Pat. No. 8,278,425); 4'-$CH_2$—O—N($CH_3$)-2' (see, e.g., U.S. Patent Publication No. 2004/0171570); 4'-$CH_2$—N(R)—O-2', wherein R is H, C1-C12 alkyl, or a protecting group (see, e.g., U.S. Pat. No. 7,427,672); 4'-$CH_2$—C(H)($CH_3$)-2' (see, e.g., Chattopadhyaya et al., *J. Org. Chem.,* 2009, 74, 118-134); and 4'-$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and U.S. Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH($CH_3$)—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, U.S. Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'—C4' have been removed (i.e. the covalent carbon-oxygen-carbon bond between the C1' and C4' carbons). In another example, the C2'—C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an iRNA. Suitable phosphate mimics are disclosed in, for example U.S. Patent Publication No. 2012/0157511, the entire contents of which are incorporated herein by reference.

A. Modified iRNAs Comprising Motifs of the Invention

In certain aspects of the invention, the double stranded RNA agents of the invention include agents with chemical modifications as disclosed, for example, in WO2013/075035, the entire contents of each of which are incorporated herein by reference. WO2013/075035 provides motifs of three identical modifications on three consecutive nucleotides into a sense strand or antisense strand of a dsRNAi agent, particularly at or near the cleavage site. In some embodiments, the sense strand and antisense strand of the dsRNAi agent may otherwise be completely modified. The introduction of these motifs interrupts the modification pattern, if present, of the sense or antisense strand. The dsRNAi agent may be optionally conjugated with a GalNAc derivative ligand, for instance on the sense strand.

More specifically, when the sense strand and antisense strand of the double stranded RNA agent are completely modified to have one or more motifs of three identical modifications on three consecutive nucleotides at or near the cleavage site of at least one strand of a dsRNAi agent, the gene silencing activity of the dsRNAi agent was observed.

Accordingly, the invention provides double stranded RNA agents capable of inhibiting the expression of a target gene (i.e., CPB2 gene) in vivo. The RNAi agent comprises a sense strand and an antisense strand. Each strand of the RNAi agent may be, for example, 17-30 nucleotides in length, 25-30 nucleotides in length, 27-30 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as "dsRNAi agent." The duplex region of a dsRNAi agent may be, for example, the duplex region can be 27-30 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 19, 20, 21, 22, 23, 24, 25, 26, and 27 nucleotides in length.

In certain embodiments, the dsRNAi agent may contain one or more overhang regions or capping groups at the 3'-end, 5'-end, or both ends of one or both strands. The overhang can be, independently, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. In certain embodiments, the overhang regions can include extended overhang regions as provided above. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In certain embodiments, the nucleotides in the overhang region of the dsRNAi agent can each independently be a modified or unmodified nucleotide including, but no limited to 2'-sugar modified, such as, 2'-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the dsRNAi agent may be phosphorylated. In some embodiments, the overhang region(s) contains two nucleotides having a phosphorothioate between the two nucleotides, where the two nucleotides can be the same or different. In some embodiments, the overhang is present at the 3'-end of the sense strand, antisense strand, or both strands. In some embodiments, this 3'-overhang is present in the antisense strand. In some embodiments, this 3'-overhang is present in the sense strand.

The dsRNAi agent may contain only a single overhang, which can strengthen the interference activity of the RNAi, without affecting its overall stability. For example, the single-stranded overhang may be located at the 3'-end of the sense strand or, alternatively, at the 3-end of the antisense strand. The RNAi may also have a blunt end, located at the 5'-end of the antisense strand (or the 3'-end of the sense strand) or vice versa. Generally, the antisense strand of the dsRNAi agent has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In certain embodiments, the dsRNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In other embodiments, the dsRNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet other embodiments, the dsRNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In certain embodiments, the dsRNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In certain embodiments, every nucleotide in the sense strand and the antisense strand of the dsRNAi agent, including the nucleotides that are part of the motifs are modified nucleotides. In certain embodiments each residue is independently modified with a 2'-O-methyl or 3'-fluoro, e.g., in an alternating motif. Optionally, the dsRNAi agent further comprises a ligand (preferably $GalNAc_3$).

In certain embodiments, the dsRNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In certain embodiments, the dsRNAi agent comprises sense and antisense strands, wherein the dsRNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein Dicer cleavage of the dsRNAi agent preferentially results in an siRNA comprising the 3'-end of the second strand, thereby reducing expression of the target gene in the mammal. Optionally, the dsRNAi agent further comprises a ligand.

In certain embodiments, the sense strand of the dsRNAi agent contains at least one motif of three identical modifications on three consecutive nucleotides, where one of the motifs occurs at the cleavage site in the sense strand.

In certain embodiments, the antisense strand of the dsRNAi agent can also contain at least one motif of three identical modifications on three consecutive nucleotides, where one of the motifs occurs at or near the cleavage site in the antisense strand.

For a dsRNAi agent having a duplex region of 19-23 nucleotide in length, the cleavage site of the antisense strand is typically around the 10, 11, and 12 positions from the 5'-end. Thus the motifs of three identical modifications may occur at the 9, 10, 11 positions; the 10, 11, 12 positions; the 11, 12, 13 positions; the 12, 13, 14 positions; or the 13, 14, 15 positions of the antisense strand, the count starting from the first nucleotide from the 5'-end of the antisense strand, or, the count starting from the first paired nucleotide within the duplex region from the 5'-end of the antisense strand. The cleavage site in the antisense strand may also change according to the length of the duplex region of the dsRNAi agent from the 5'-end.

The sense strand of the dsRNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In some embodiments, the sense strand of the dsRNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistries of the motifs are distinct from each other, and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the dsRNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In some embodiments, the wing modification on the sense strand or antisense strand of the dsRNAi agent typically does not include the first one or two terminal nucleotides at the 3'-end, 5'-end, or both ends of the strand.

In other embodiments, the wing modification on the sense strand or antisense strand of the dsRNAi agent typically does not include the first one or two paired nucleotides within the duplex region at the 3'-end, 5'-end, or both ends of the strand.

When the sense strand and the antisense strand of the dsRNAi agent each contain at least one wing modification, the wing modifications may fall on the same end of the duplex region, and have an overlap of one, two, or three nucleotides.

When the sense strand and the antisense strand of the dsRNAi agent each contain at least two wing modifications, the sense strand and the antisense strand can be so aligned that two modifications each from one strand fall on one end of the duplex region, having an overlap of one, two, or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In some embodiments, every nucleotide in the sense strand and antisense strand of the dsRNAi agent, including the nucleotides that are part of the motifs, may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2'-hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3'- or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5'-end or ends can be phosphorylated.

It may be possible, e.g., to enhance stability, to include particular bases in overhangs, or to include modified nucleotides or nucleotide surrogates, in single strand overhangs, e.g., in a 5'- or 3'-overhang, or in both. For example, it can be desirable to include purine nucleotides in overhangs. In some embodiments all or some of the bases in a 3'- or 5'-overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In certain embodiments, the $N_a$ or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5' to 3' of the strand and the alternating motif in the antisense strand may start with "BABABA" from 5' to 3' of the strand within the duplex region. As another example, the alternating motif in the sense strand may start with "AABBAABB" from 5' to 3' of the strand and the alternating motif in the antisense strand may start with "BBAABBAA" from 5' to 3' of the strand within the duplex region, so that there is a complete or partial shift of the modification patterns between the sense strand and the antisense strand.

In some embodiments, the dsRNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand or antisense strand interrupts the initial modification pattern present in the sense strand or antisense strand. This interruption of the modification pattern of the sense or antisense strand by introducing one or more motifs of three identical modifications on three consecutive nucleotides to the sense or antisense strand may enhance the gene silencing activity against the target gene.

In some embodiments, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ or $N_b$ may be present or absent when there is a wing modification present.

The iRNA may further comprise at least one phosphorothioate or methylphosphonate internucleotide linkage. The phosphorothioate or methylphosphonate internucleotide linkage modification may occur on any nucleotide of the sense strand, antisense strand, or both strands in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In some embodiments, the antisense strand comprises two phosphorothioate internucleotide linkages at the 5'-end and two phosphorothioate internucleotide linkages at the 3'-end, and the sense strand comprises at least two phosphorothioate internucleotide linkages at either the 5'-end or the 3'-end.

In some embodiments, the dsRNAi agent comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, or the 5'end of the antisense strand.

In some embodiments, the 2-nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the dsRNAi agent may additionally have two phosphorothioate internucleotide linkages between the terminal three nucleotides at both the 5'-end of the sense strand and at the 5'-end of the antisense strand.

In one embodiment, the dsRNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In certain embodiments, the dsRNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In certain embodiments, the nucleotide at the 1 position within the duplex region from the 5'-end in the antisense strand is selected from A, dA, dU, U, and dT. Alternatively, at least one of the first 1, 2, or 3 base pair within the duplex region from the 5'-end of the antisense strand is an AU base pair. For example, the first base pair within the duplex region from the 5'-end of the antisense strand is an AU base pair.

In other embodiments, the nucleotide at the 3'-end of the sense strand is deoxy-thymine (dT) or the nucleotide at the 3'-end of the antisense strand is deoxy-thymine (dT). For example, there is a short sequence of deoxy-thymine nucleotides, for example, two dT nucleotides on the 3'-end of the sense, antisense strand, or both strands.

In certain embodiments, the sense strand sequence may be represented by formula (I):

$$5'n_p\text{-}N_a\text{—}(XXX)_i\text{—}N_b\text{—}YYY\text{—}N_b\text{—}(ZZZ)_j\text{—}N_a\text{-}n_q3' \qquad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein $N_b$ and Y do not have the same modification; and

XXX, YYY, and ZZZ each independently represent one motif of three identical modifications on three consecutive nucleotides. Preferably YYY is all 2'-F modified nucleotides.

In some embodiments, the $N_a$ or $N_b$ comprises modifications of alternating pattern.

In some embodiments, the YYY motif occurs at or near the cleavage site of the sense strand.

For example, when the dsRNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12; or 11, 12, 13) of the sense strand, the count starting from the first nucleotide, from the 5'-end; or optionally, the count starting at the first paired nucleotide within the duplex region, from the 5'-end.

In one embodiment, i is 1 and j is 0, or i is 0 and j is 1, or both i and j are 1. The sense strand can therefore be represented by the following formulas:

$$5'n_p\text{-}N_a\text{—}YYY\text{—}N_b\text{—}ZZZ\text{—}N_a\text{-}n_q3' \qquad (Ib);$$

$$5'n_p\text{-}N_a\text{—}XXX\text{—}N_b\text{—}YYY\text{—}N_a\text{-}n_q3' \qquad (Ic); \text{ or}$$

$$5'n_p\text{-}N_a\text{—}XXX\text{—}N_b\text{—}YYY\text{—}N_b\text{—}ZZZ\text{—}N_a\text{-}n_q3' \qquad (Id).$$

When the sense strand is represented by formula (Ib), $N_b$ represents an oligonucleotide sequence comprising 0-10, 0-7, 0-5, 0-4, 0-2, or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2, or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2, or 0 modified nucleotides. Preferably, $N_b$ is 0, 1, 2, 3, 4, 5, or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'n_p\text{-}N_a\text{—}YYY\text{—}N_a\text{-}n_q3' \qquad (Ia).$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'n_{q'}\text{—}N_a'\text{—}(Z'Z'Z')_k\text{—}N_b'\text{—}Y'Y'Y'\text{—}N_b'\text{—}(X'X'X')_l\text{—}N'_a\text{-}n_p'3' \qquad (II)$$

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides; each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y', and Z'Z'Z' each independently represent one motif of three identical modifications on three consecutive nucleotides.

In some embodiments, the $N_a'$ or $N_b'$ comprises modifications of alternating pattern.

The Y'Y'Y' motif occurs at or near the cleavage site of the antisense strand. For example, when the dsRNAi agent has a duplex region of 17-23 nucleotides in length, the Y'Y'Y' motif can occur at positions 9, 10, 11; 10, 11, 12; 11, 12, 13; 12, 13, 14; or 13, 14, 15 of the antisense strand, with the count starting from the first nucleotide, from the 5'-end; or optionally, the count starting at the first paired nucleotide within the duplex region, from the 5'-end. Preferably, the Y'Y'Y' motif occurs at positions 11, 12, 13.

In certain embodiments, Y'Y'Y' motif is all 2'-OMe modified nucleotides.

In certain embodiments, k is 1 and 1 is 0, or k is 0 and 1 is 1, or both k and l are 1.

The antisense strand can therefore be represented by the following formulas:

$$5'n_q'\text{—}N_a'\text{—}Z'Z'Z'\text{—}N_b'\text{—}Y'Y'Y'\text{—}N_a'\text{-}n_{p'}3' \qquad (IIb);$$

$$5'n_q'\text{—}N_a'\text{—}Y'Y'Y'\text{—}N_b'\text{—}X'X'X'\text{-}n_{p'}3' \qquad (IIc); \text{ or}$$

$$5'n_q'\text{—}N_a'\text{—}Z'Z'Z'\text{—}N_b'\text{—}Y'Y'Y'\text{—}N_b'\text{—}X'X'X'\text{—}N_a'\text{-}n_p'3' \qquad (IId).$$

When the antisense strand is represented by formula (IIb), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2, or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2, or 0 modified nucleotides.

Each $N_a'$ independently represents an oligonucleotide sequence comprising 2-20, 2-15, or 2-10 modified nucleotides. Preferably, $N_b$ is 0, 1, 2, 3, 4, 5, or 6.

In other embodiments, k is 0 and 1 is 0 and the antisense strand may be represented by the formula:

$$5'n_{p'}—N_{a'}—Y'Y'Y'—N_{a}'-n_{q'}3' \quad \text{(Ia).}$$

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y', and Z', in particular, may represent a 2'-O-methyl modification or a 2'-fluoro modification.

In some embodiments, the sense strand of the dsRNAi agent may contain YYY motif occurring at 9, 10, and 11 positions of the strand when the duplex region is 21 nt, the count starting from the first nucleotide from the 5'-end, or optionally, the count starting at the first paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In some embodiments the antisense strand may contain Y'Y'Y' motif occurring at positions 11, 12, 13 of the strand, the count starting from the first nucleotide from the 5'-end, or optionally, the count starting at the first paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with an antisense strand being represented by any one of formulas (IIa), (IIb), (IIc), and (IId), respectively.

Accordingly, the dsRNAi agents for use in the methods of the invention may comprise a sense strand and an antisense strand, each strand having 14 to 30 nucleotides, the iRNA duplex represented by formula (III):

$$\text{sense: } 5'n_p\text{-}N_a—(XXX)_i—N_b—YYY—N_b—(ZZZ)_j—N_a\text{-}n_q3'$$

$$\text{antisense: } 3'n_p'—N_a'—(X'X'X')_k—N_b'—Y'Y'Y'—N_b'—(Z'Z'Z')_lN_a'\text{-}n_q'\ 5' \quad \text{(III)}$$

wherein:

i, j, k, and l are each independently 0 or 1;

p, p', q, and q' are each independently 0-6;

each $N_a$ and $N_a'$ independently represents an oligonucleotide sequence comprising 0-25 modified nucleotides, each sequence comprising at least two differently modified nucleotides; each $N_b$ and $N_b'$ independently represents an oligonucleotide sequence comprising 0-10 modified nucleotides;

wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and 1 is 0; or k is 1 and 1 is 0; k is 0 and 1 is 1; or both k and l are 0; or both k and l are 1.

Exemplary combinations of the sense strand and antisense strand forming an iRNA duplex include the formulas below:

$$5'n_p\text{-}N_a—YYY—N_a\text{-}n_q3'$$

$$3'n_p'—N_a'—Y'Y'Y'—N_a'n_q'\ 5' \quad \text{(IIIa)}$$

$$5'n_p\text{-}N_a—YYY—N_b—ZZZ—N_a\text{-}n_q3'$$

$$3'n_p'—N_a'—Y'Y'Y'—N_b'—Z'Z'Z'—N_a'n_q'\ 5' \quad \text{(IIIb)}$$

$$5'n_p\text{-}N_a—XXX—N_b—YYY—N_a\text{-}n_q3'$$

$$3'n_p'—N_a'—X'X'X'—N_b'—Y'Y'Y'—N_a'\text{-}n_q'\ 5' \quad \text{(IIIc)}$$

$$5'n_p\text{-}N_a—XXX—N_b—YYY—N_b—ZZZ—N_a\text{-}n_q3'$$

$$3'n_p'—N_a'—X'X'X'—N_b'—Y'Y'Y'—N_b'—Z'Z'Z'—N_a\text{-}n_q'5' \quad \text{(IIId)}$$

When the dsRNAi agent is represented by formula (IIIa), each $N_a$ independently represents an oligonucleotide sequence comprising 2-20, 2-15, or 2-10 modified nucleotides.

When the dsRNAi agent is represented by formula (IIIb), each $N_b$ independently represents an oligonucleotide sequence comprising 1-10, 1-7, 1-5, or 1-4 modified nucleotides. Each $N_a$ independently represents an oligonucleotide sequence comprising 2-20, 2-15, or 2-10 modified nucleotides.

When the dsRNAi agent is represented as formula (IIIc), each $N_b$, $N_b'$ independently represents an oligonucleotide sequence comprising 0-10, 0-7, 0-10, 0-7, 0-5, 0-4, 0-2, or 0 modified nucleotides. Each $N_a$ independently represents an oligonucleotide sequence comprising 2-20, 2-15, or 2-10 modified nucleotides.

When the dsRNAi agent is represented as formula (IIId), each $N_b$, $N_b'$ independently represents an oligonucleotide sequence comprising 0-10, 0-7, 0-10, 0-7, 0-5, 0-4, 0-2, or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$, and $N_b'$ independently comprises modifications of alternating pattern.

Each of X, Y, and Z in formulas (III), (IIIa), (IIIb), (IIIc), and (IIId) may be the same or different from each other.

When the dsRNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the dsRNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In certain embodiments, the modification on the Y nucleotide is different than the modification on the Y' nucleotide, the modification on the Z nucleotide is different than the modification on the Z' nucleotide, or the modification on the X nucleotide is different than the modification on the X' nucleotide.

In certain embodiments, when the dsRNAi agent is represented by formula (IIId), the $N_a$ modifications are 2'-O-methyl or 2'-fluoro modifications. In other embodiments, when the RNAi agent is represented by formula (IIId), the $N_a$ modifications are 2'-O-methyl or 2'-fluoro modifications and $n_p$'>0 and at least one $n_p$' is linked to a neighboring nucleotide a via phosphorothioate linkage. In yet other embodiments, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, and the sense strand is conjugated to one or more GalNAc derivatives attached through a bivalent or trivalent branched linker (described below). In other embodiments, when the RNAi agent is represented by formula (IIId), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, when the dsRNAi agent is represented by formula (IIIa), the $N_a$ modifications are 2'-O-methyl or 2'-fluoro modifications, $n_p$'>0 and at least one $n_p$' is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In some embodiments, the dsRNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In some embodiments, the dsRNAi agent is a multimer containing three, four, five, six, or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two dsRNAi agents represented by at least one of formulas (III), (IIIa), (IIIb), (IIIc), and (IIId) are linked to each other at the 5' end, and one or both of the 3' ends, and are optionally conjugated to a ligand. Each of the agents can target the same gene or two different genes; or each of the agents can target same gene at two different target sites.

In certain embodiments, an RNAi agent of the invention may contain a low number of nucleotides containing a 2'-fluoro modification, e.g., 10 or fewer nucleotides with 2'-fluoro modification. For example, the RNAi agent may contain 10, 9, 8, 7, 6, 5, 4, 3, 2, 1 or 0 nucleotides with a 2'-fluoro modification. In a specific embodiment, the RNAi agent of the invention contains 10 nucleotides with a 2'-fluoro modification, e.g., 4 nucleotides with a 2'-fluoro modification in the sense strand and 6 nucleotides with a 2'-fluoro modification in the antisense strand. In another specific embodiment, the RNAi agent of the invention contains 6 nucleotides with a 2'-fluoro modification, e.g., 4 nucleotides with a 2'-fluoro modification in the sense strand and 2 nucleotides with a 2'-fluoro modification in the antisense strand.

In other embodiments, an RNAi agent of the invention may contain an ultra low number of nucleotides containing a 2'-fluoro modification, e.g., 2 or fewer nucleotides containing a 2'-fluoro modification. For example, the RNAi agent may contain 2, 1 of 0 nucleotides with a 2'-fluoro modification. In a specific embodiment, the RNAi agent may contain 2 nucleotides with a 2'-fluoro modification, e.g., 0 nucleotides with a 2-fluoro modification in the sense strand and 2 nucleotides with a 2'-fluoro modification in the antisense strand.

Various publications describe multimeric iRNAs that can be used in the methods of the invention. Such publications include WO2007/091269, U.S. Pat. No. 7,858,769, WO2010/141511, WO2007/117686, WO2009/014887, and WO2011/031520 the entire contents of each of which are hereby incorporated herein by reference.

As described in more detail below, the iRNA that contains conjugations of one or more carbohydrate moieties to an iRNA can optimize one or more properties of the iRNA. In many cases, the carbohydrate moiety will be attached to a modified subunit of the iRNA. For example, the ribose sugar of one or more ribonucleotide subunits of a iRNA can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide, or polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The iRNA may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl, and decalin; preferably, the acyclic group is a serinol backbone or diethanolamine backbone.

-continued

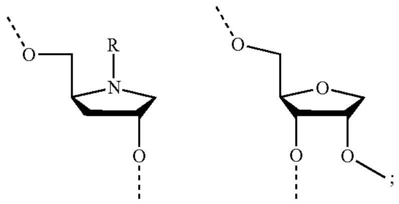

In another embodiment of the invention, an iRNA agent comprises a sense strand and an antisense strand, each strand having 14 to 40 nucleotides. The RNAi agent may be represented by formula (L):

(L)

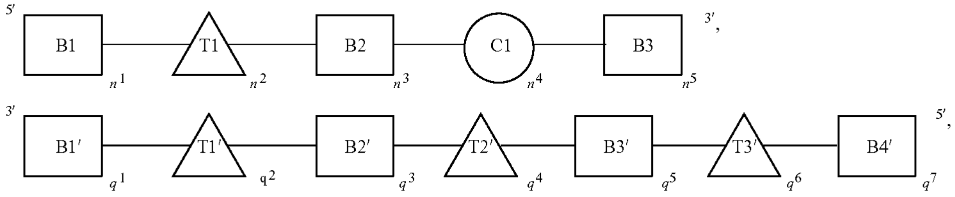

In formula (L), B1, B2, B3, B1', B2', B3', and B4' each are independently a nucleotide containing a modification selected from the group consisting of 2'-O-alkyl, 2'-substituted alkoxy, 2'-substituted alkyl, 2'-halo, ENA, and BNA/LNA. In one embodiment, B1, B2, B3, B1', B2', B3', and B4' each contain 2'-OMe modifications. In one embodiment, B1, B2, B3, B1', B2', B3', and B4' each contain 2'-OMe or 2'-F modifications. In one embodiment, at least one of B1, B2, B3, B1', B2', B3', and B4' contain 2'-O—N-methylacetamido (2'-O-NMA) modification.

C1 is a thermally destabilizing nucleotide placed at a site opposite to the seed region of the antisense strand (i.e., at positions 2-8 of the 5'-end of the antisense strand). For example, C1 is at a position of the sense strand that pairs with a nucleotide at positions 2-8 of the 5'-end of the antisense strand. In one example, C1 is at position 15 from the 5'-end of the sense strand. C1 nucleotide bears the thermally destabilizing modification which can include abasic modification; mismatch with the opposing nucleotide in the duplex; and sugar modification such as 2'-deoxy modification or acyclic nucleotide e.g., unlocked nucleic acids (UNA) or glycerol nucleic acid (GNA). In one embodiment, C1 has thermally destabilizing modification selected from the group consisting of: i) mismatch with the opposing nucleotide in the antisense strand; ii) abasic modification selected from the group consisting of:

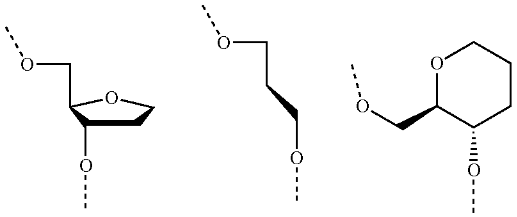

and iii) sugar modification selected from the group consisting of:

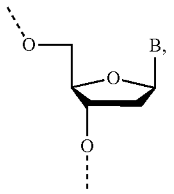

2'-deoxy

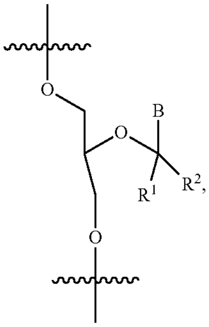

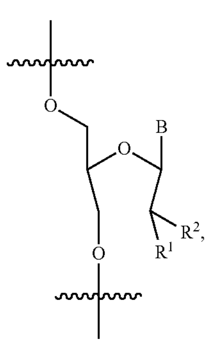

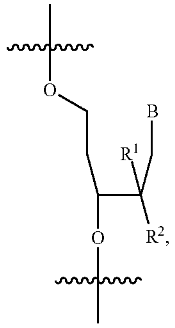

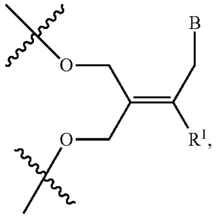

and

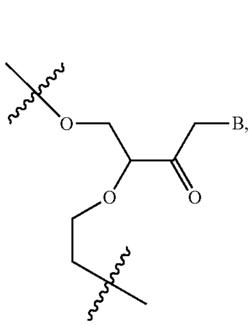

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar. In one embodiment, the thermally destabilizing modification in C1 is a mismatch selected from the group consisting of G:G, G:A, G:U, G:T, A:A, A:C, C:C, C:U, C:T, U:U, T:T, and U:T; and optionally, at least one nucleobase in the mismatch pair is a 2'-deoxy nucleobase. In one example, the thermally destabilizing modification in C1 is GNA or

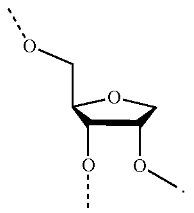

T1, T1', T2', and T3' each independently represent a nucleotide comprising a modification providing the nucleotide a steric bulk that is less or equal to the steric bulk of a 2'-OMe modification. A steric bulk refers to the sum of steric effects of a modification. Methods for determining steric effects of a modification of a nucleotide are known to one skilled in the art. The modification can be at the 2' position of a ribose sugar of the nucleotide, or a modification to a non-ribose nucleotide, acyclic nucleotide, or the backbone of the nucleotide that is similar or equivalent to the 2' position of the ribose sugar, and provides the nucleotide a steric bulk that is less than or equal to the steric bulk of a 2'-OMe modification. For example, T1, T1', T2', and T3' are each independently selected from DNA, RNA, LNA, 2'-F, and 2'-F-5'-methyl. In one embodiment, T1 is DNA. In one embodiment, T1' is DNA, RNA or LNA. In one embodiment, T2' is DNA or RNA. In one embodiment, T3' is DNA or RNA.

$n^1$, $n^3$, and q' are independently 4 to 15 nucleotides in length.

$n^5$, $q^3$, and $q^7$ are independently 1-6 nucleotide(s) in length.

$n^4$, $q^2$, and $q^6$ are independently 1-3 nucleotide(s) in length; alternatively, $n^4$ is 0.

$q^5$ is independently 0-10 nucleotide(s) in length.

$n^2$ and $q^4$ are independently 0-3 nucleotide(s) in length.

Alternatively, $n^4$ is 0-3 nucleotide(s) in length.

In one embodiment, $n^4$ can be 0. In one example, $n^4$ is 0, and $q^2$ and $q^6$ are 1. In another example, $n^4$ is 0, and $q^2$ and $q^6$ are 1, with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$, $q^2$, and $q^6$ are each 1.

In one embodiment, $n^2$, $n^4$, $q^2$, $q^4$, and $q^6$ are each 1.

In one embodiment, C1 is at position 14-17 of the 5'-end of the sense strand, when the sense strand is 19-22 nucleotides in length, and $n^4$ is 1. In one embodiment, C1 is at position 15 of the 5'-end of the sense strand In one embodiment, T3' starts at position 2 from the 5' end of the antisense strand. In one example, T3' is at position 2 from the 5' end of the antisense strand and $q^6$ is equal to 1.

In one embodiment, T1' starts at position 14 from the 5' end of the antisense strand. In one example, T1' is at position 14 from the 5' end of the antisense strand and $q^2$ is equal to 1.

In an exemplary embodiment, T3' starts from position 2 from the 5' end of the antisense strand and T1' starts from position 14 from the 5' end of the antisense strand. In one example, T3' starts from position 2 from the 5' end of the antisense strand and $q^6$ is equal to 1 and T1' starts from position 14 from the 5' end of the antisense strand and $q^2$ is equal to 1.

In one embodiment, T1' and T3' are separated by 11 nucleotides in length (i.e. not counting the T1' and T3' nucleotides).

In one embodiment, T1' is at position 14 from the 5' end of the antisense strand. In one example, T1' is at position 14 from the 5' end of the antisense strand and $q^2$ is equal to 1, and the modification at the 2' position or positions in a non-ribose, acyclic or backbone that provide less steric bulk than a 2'-OMe ribose.

In one embodiment, T3' is at position 2 from the 5' end of the antisense strand. In one example, T3' is at position 2 from the 5' end of the antisense strand and $q^6$ is equal to 1, and the modification at the 2' position or positions in a non-ribose, acyclic or backbone that provide less than or equal to steric bulk than a 2'-OMe ribose.

In one embodiment, T1 is at the cleavage site of the sense strand. In one example, T1 is at position 11 from the 5' end of the sense strand, when the sense strand is 19-22 nucleotides in length, and $n^2$ is 1. In an exemplary embodiment, T1 is at the cleavage site of the sense strand at position 11 from the 5' end of the sense strand, when the sense strand is 19-22 nucleotides in length, and $n^2$ is 1, In one embodiment, T2' starts at position 6 from the 5' end of the antisense strand. In one example, T2' is at positions 6-10 from the 5' end of the antisense strand, and $q^4$ is 1.

In an exemplary embodiment, T1 is at the cleavage site of the sense strand, for instance, at position 11 from the 5' end of the sense strand, when the sense strand is 19-22 nucleotides in length, and $n^2$ is 1; T1' is at position 14 from the 5' end of the antisense strand, and $q^2$ is equal to 1, and the modification to T1' is at the 2' position of a ribose sugar or at positions in a non-ribose, acyclic or backbone that provide less steric bulk than a 2'-OMe ribose; T2' is at positions 6-10 from the 5' end of the antisense strand, and $q^4$ is 1; and T3' is at position 2 from the 5' end of the antisense strand, and $q^6$ is equal to 1, and the modification to T3' is at the 2' position or at positions in a non-ribose, acyclic or backbone that provide less than or equal to steric bulk than a 2'-OMe ribose.

In one embodiment, T2' starts at position 8 from the 5' end of the antisense strand. In one example, T2' starts at position 8 from the 5' end of the antisense strand, and $q^4$ is 2.

In one embodiment, T2' starts at position 9 from the 5' end of the antisense strand. In one example, T2' is at position 9 from the 5' end of the antisense strand, and $q^4$ is 1.

In one embodiment, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, $n^4$ is 0, B3 is 2'-OMe, $n^4$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1.

In one embodiment, B1 is 2'-OMe or 2'-F, $n^1$ is 6, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 7, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 1, B3' is 2'-OMe or 2'-F, $q^5$ is 6, T3' is 2'-F, $q^6$ is 1, B4' is 2'-OMe, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 5, T2' is 2'-F, $q^4$ is 1, B3' is 2'-OMe or 2'-F, $q^5$ is 5, T3' is 2'-F, $q^6$ is 1, B4' is 2'-OMe, and $q^7$ is 1; optionally with at least 2 additional TT at the 3'-end of the antisense strand; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within positions 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within positions 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand).

The RNAi agent can comprise a phosphorus-containing group at the 5'-end of the sense strand or antisense strand. The 5'-end phosphorus-containing group can be 5'-end phosphate (5'-P), 5'-end phosphorothioate (5'-PS), 5'-end phosphorodithioate (5'-$PS_2$), 5'-end vinylphosphonate (5'-VP), 5'-end methylphosphonate (MePhos), or 5'-deoxy-5'-C-malonyl (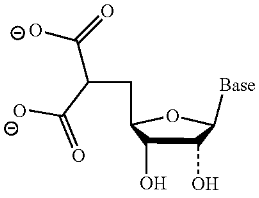).

When the 5'-end phosphorus-containing group is 5'-end vinylphosphonate (5'-VP), the 5'-VP can be either 5'-E-VP isomer (i.e., trans-vinylphosphate,

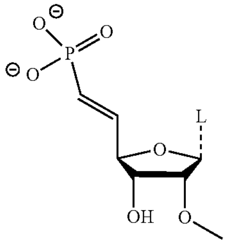),

5'-Z—VP isomer (i.e., cis-vinylphosphate,

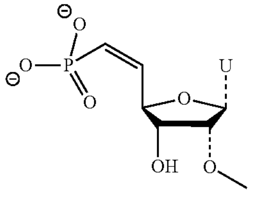), or mixtures thereof.

In one embodiment, the RNAi agent comprises a phosphorus-containing group at the 5'-end of the sense strand. In one embodiment, the RNAi agent comprises a phosphorus-containing group at the 5'-end of the antisense strand.

In one embodiment, the RNAi agent comprises a 5'-P. In one embodiment, the RNAi agent comprises a 5'-P in the antisense strand.

In one embodiment, the RNAi agent comprises a 5'-PS. In one embodiment, the RNAi agent comprises a 5'-PS in the antisense strand.

In one embodiment, the RNAi agent comprises a 5'-VP. In one embodiment, the RNAi agent comprises a 5'-VP in the antisense strand. In one embodiment, the RNAi agent comprises a 5'-E-VP in the antisense strand. In one embodiment, the RNAi agent comprises a 5'-Z—VP in the antisense strand.

In one embodiment, the RNAi agent comprises a 5'-$PS_2$. In one embodiment, the RNAi agent comprises a 5'-$PS_2$ in the antisense strand.

In one embodiment, the RNAi agent comprises a 5'-$PS_2$. In one embodiment, the RNAi agent comprises a 5'-deoxy-5'-C-malonyl in the antisense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The dsRNA agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The dsRNAi RNA agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1. The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP. The 5'-VP may be 5'-E-VP, 5'-Z—VP, or combination thereof.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof), and a targeting ligand.

In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-OMe, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-OMe, and $q^7$ is 1; with two phosphorothioate internucleotide linkage modifications within position 1-5 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-$PS_2$ and a targeting ligand. In one embodiment, the 5'-$PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, T2' is 2'-F, $q^4$ is 2, B3' is 2'-OMe or 2'-F, $q^5$ is 5, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-P and a targeting ligand. In one embodiment, the 5'-P is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-PS and a targeting ligand. In one embodiment, the 5'-PS is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-VP (e.g., a 5'-E-VP, 5'-Z—VP, or combination thereof) and a targeting ligand. In one embodiment, the 5'-VP is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a $5'-PS_2$ and a targeting ligand. In one embodiment, the $5'-PS_2$ is at the 5'-end of the antisense strand, and the targeting ligand is at the 3'-end of the sense strand.

In one embodiment, B1 is 2'-OMe or 2'-F, $n^1$ is 8, T1 is 2'F, $n^2$ is 3, B2 is 2'-OMe, $n^3$ is 7, $n^4$ is 0, B3 is 2'-OMe, $n^5$ is 3, B1' is 2'-OMe or 2'-F, $q^1$ is 9, T1' is 2'-F, $q^2$ is 1, B2' is 2'-OMe or 2'-F, $q^3$ is 4, $q^4$ is 0, B3' is 2'-OMe or 2'-F, $q^5$ is 7, T3' is 2'-F, $q^6$ is 1, B4' is 2'-F, and $q^7$ is 1; with two phosphorothioate internucleotide linkage modifications within position 1-5 of the sense strand (counting from the 5'-end of the sense strand), and two phosphorothioate internucleotide linkage modifications at positions 1 and 2 and two phosphorothioate internucleotide linkage modifications within positions 18-23 of the antisense strand (counting from the 5'-end of the antisense strand). The RNAi agent also comprises a 5'-deoxy-5'-C-malonyl and a targeting ligand. In one embodiment, the 5'-deoxy-5'-C-malonyl is at the 5'-end of the antisense strand, and the targeting ligand is at the 3'-end of the sense strand.

In a particular embodiment, an RNAi agent of the present invention comprises:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker; and
   (iii) 2'-F modifications at positions 1, 3, 5, 7, 9 to 11, 13, 17, 19, and 21, and 2'-OMe
   modifications at positions 2, 4, 6, 8, 12, 14 to 16, 18, and 20 (counting from the 5' end); and
(b) an antisense strand having:
   (i) a length of 23 nucleotides;
   (ii) 2'-OMe modifications at positions 1, 3, 5, 9, 11 to 13, 15, 17, 19, 21, and 23, and 2'F modifications at positions 2, 4, 6 to 8, 10, 14, 16, 18, 20, and 22 (counting from the 5' end); and
   (iii) phosphorothioate internucleotide linkages between nucleotide positions 21 and 22, and between nucleotide positions 22 and 23 (counting from the 5' end);

wherein the dsRNA agents have a two nucleotide overhang at the 3'-end of the antisense strand, and a blunt end at the 5'-end of the antisense strand.

In another particular embodiment, an RNAi agent of the present invention comprises:

(a) a sense strand having:
   (i) a length of 21 nucleotides;
   (ii) an ASGPR ligand attached to the 3'-end, wherein said ASGPR ligand comprises three GalNAc derivatives attached through a trivalent branched linker;
   (iii) 2'-F modifications at positions 1, 3, 5, 7, 9 to 11, 13, 15, 17, 19, and 21, and 2'-OMe modifications at positions 2, 4, 6, 8, 12, 14, 16, 18, and 20 (counting from the 5' end); and
   (iv) phosphorothioate internucleotide linkages between nucleotide positions 1 and 2, and between nucleotide positions 2 and 3 (counting from the 5' end); and
(b) an antisense strand having:
   (i) a length of 23 nucleotides;
   (ii) 2'-OMe modifications at positions 1, 3, 5, 7, 9, 11 to 13, 15, 17, 19, and 21 to 23, and 2'F modifications at positions 2, 4, 6, 8, 10, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, and 12 to 21, 2'—F modifications at positions 7, and 9, and a deoxy-nucleotide (e.g. dT) at position 11 (counting from the 5' end); and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 7, 9, 11, 13, 15, 17, and 19 to 23, and 2'-F modifications at positions 2, 4 to 6, 8, 10, 12, 14, 16, and 18 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 6, 8, 10, 12, 14, and 16 to 21, and 2'-F modifications at positions 7, 9, 11, 13, and 15; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 5, 7, 9, 11, 13, 15, 17, 19, and 21 to 23, and 2'-F modifications at positions 2 to 4, 6, 8, 10, 12, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1 to 9, and 12 to 21, and 2'-F modifications at positions 10, and 11; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 5, 7, 9, 11 to 13, 15, 17, 19, and 21 to 23, and 2'-F modifications at positions 2, 4, 6, 8, 10, 14, 16, 18, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 1, 3, 5, 7, 9 to 11, and 13, and 2'-OMe modifications at positions 2, 4, 6, 8, 12, and 14 to 21; and
(iv) phosphorothioate internucleotide linkages between nucleotide positions 1 and 2, and between nucleotide positions 2 and 3 (counting from the 5' end);

and (b) an antisense strand having:
(i) a length of 23 nucleotides;
(ii) 2'-OMe modifications at positions 1, 3, 5 to 7, 9, 11 to 13, 15, 17 to 19, and 21 to 23, and 2'-F modifications at positions 2, 4, 8, 10, 14, 16, and 20 (counting from the 5' end); and
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-OMe modifications at positions 1, 2, 4, 6, 8, 12, 14, 15, 17, and 19 to 21, and 2'-F modifications at positions 3, 5, 7, 9 to 11, 13, 16, and 18; and (iv) phosphorothioate internucleotide linkages between nucleotide positions 1 and 2, and between nucleotide positions 2 and 3 (counting from the 5' end);

and (b) an antisense strand having:

(i) a length of 25 nucleotides;

(ii) 2'-OMe modifications at positions 1, 4, 6, 7, 9, 11 to 13, 15, 17, and 19 to 23, 2'—F modifications at positions 2, 3, 5, 8, 10, 14, 16, and 18, and desoxy-nucleotides (e.g. dT) at positions 24 and 25 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a four nucleotide overhang at the 3'-end of the antisense strand, and a blunt end at the 5'-end of the antisense strand.

In another particular embodiment, a RNAi agent of the present invention comprises:

(a) a sense strand having:

(i) a length of 21 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 6, 8, and 12 to 21, and 2'-F modifications at positions 7, and 9 to 11; and (iv) phosphorothioate internucleotide linkages between nucleotide positions 1 and 2, and between nucleotide positions 2 and 3 (counting from the 5' end);

and (b) an antisense strand having:

(i) a length of 23 nucleotides;

(ii) 2'-OMe modifications at positions 1, 3 to 5, 7, 8, 10 to 13, 15, and 17 to 23, and 2'-F modifications at positions 2, 6, 9, 14, and 16 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:

(i) a length of 21 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 6, 8, and 12 to 21, and 2'-F modifications at positions 7, and 9 to 11; and (iv) phosphorothioate internucleotide linkages between nucleotide positions 1 and 2, and between nucleotide positions 2 and 3 (counting from the 5' end);

and (b) an antisense strand having:

(i) a length of 23 nucleotides;

(ii) 2'-OMe modifications at positions 1, 3 to 5, 7, 10 to 13, 15, and 17 to 23, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 21 and 22, and between nucleotide positions 22 and 23 (counting from the 5' end);

wherein the RNAi agents have a two nucleotide overhang at the 3'-end of the antisense strand, and a blunt end at the 5'-end of the antisense strand.

In another particular embodiment, a RNAi agent of the present invention comprises:

(a) a sense strand having:

(i) a length of 19 nucleotides;

(ii) an ASGPR ligand attached to the 3'-end, wherein said ASGPR ligand comprises three GalNAc derivatives attached through a trivalent branched linker;

(iii) 2'-OMe modifications at positions 1 to 4, 6, and 10 to 19, and 2'-F modifications at positions 5, and 7 to 9; and (iv) phosphorothioate internucleotide linkages between nucleotide positions 1 and 2, and between nucleotide positions 2 and 3 (counting from the 5' end);

and (b) an antisense strand having:

(i) a length of 21 nucleotides;

(ii) 2'-OMe modifications at positions 1, 3 to 5, 7, 10 to 13, 15, and 17 to 21, and 2'-F modifications at positions 2, 6, 8, 9, 14, and 16 (counting from the 5' end); and (iii) phosphorothioate internucleotide linkages between nucleotide positions 1 and 2, between nucleotide positions 2 and 3, between nucleotide positions 19 and 20, and between nucleotide positions 20 and 21 (counting from the 5' end);

wherein the RNAi agents have a two nucleotide overhang at the 3'-end of the antisense strand, and a blunt end at the 5'-end of the antisense strand.

In certain embodiments, the iRNA for use in the methods of the invention is an agent selected from agents listed in Table 2, or Table 3. These agents may further comprise a ligand.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acid. Sci. USA,* 1989, 86: 6553-6556). In other embodiments, the ligand is cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting, or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands do not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxol, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In other embodiments, the lipid based ligand binds HSA weakly or not at all, such that the conjugate will be preferably distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 29). An RFGF analogue (e.g., amino acid sequence AALLPVLLAAP (SEQ ID NO:30) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:31) and the *Drosophila* Antennapedia protein (RQIKIWFQNRRMKWKK (SEQ ID NO:32) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In one embodiment, a carbohydrate conjugate for use in the compositions and methods of the invention is selected from the group consisting of:

Formula II

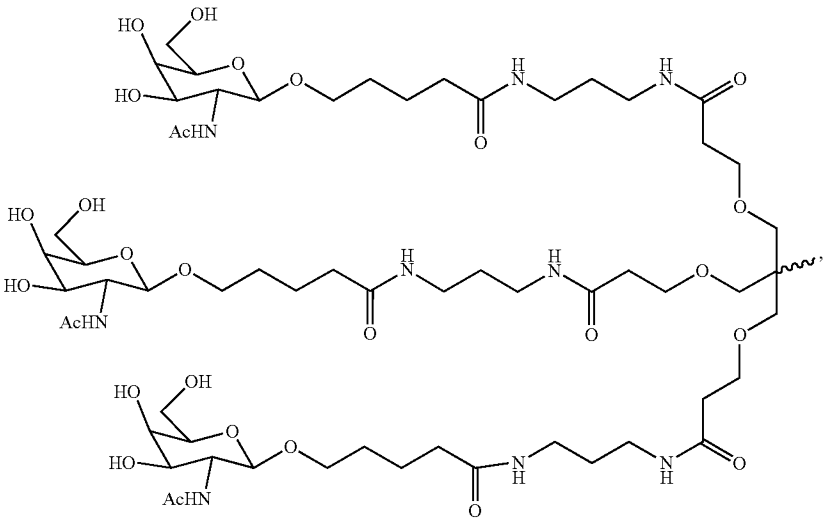

Formula III

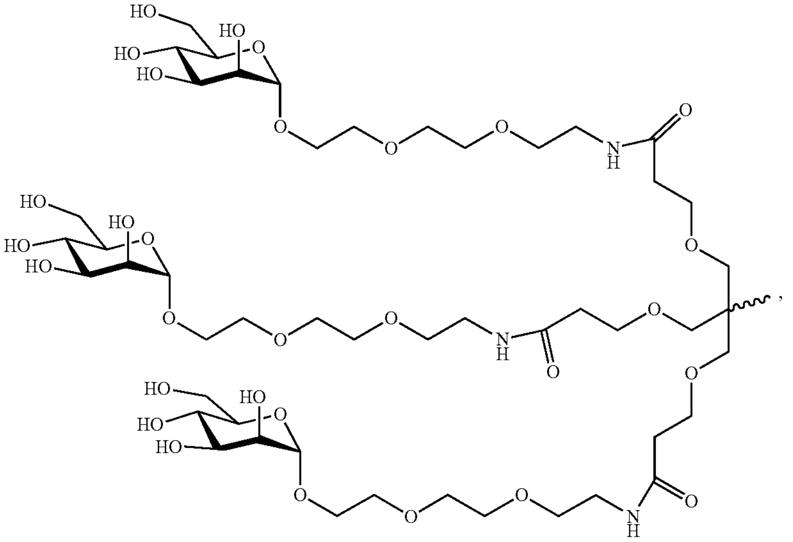

-continued
Formula IV
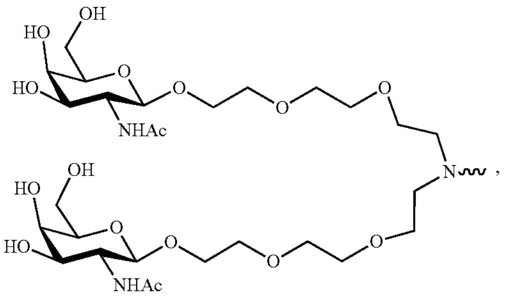
Formula V
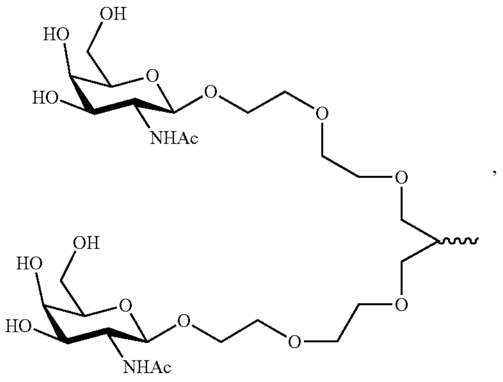
Formula VI
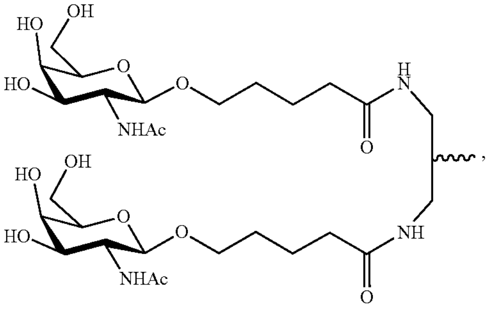
Formula VII
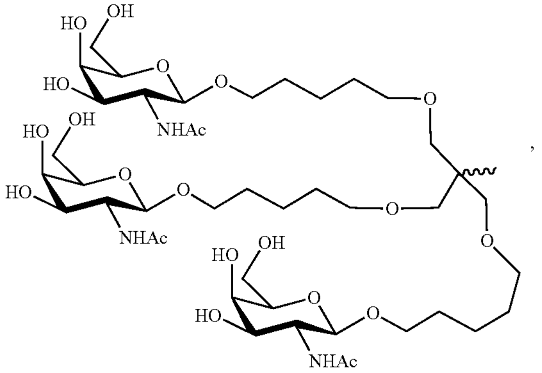
Formula VIII
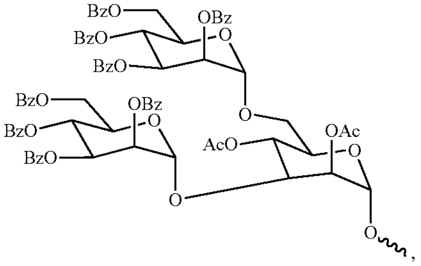
Formula IX
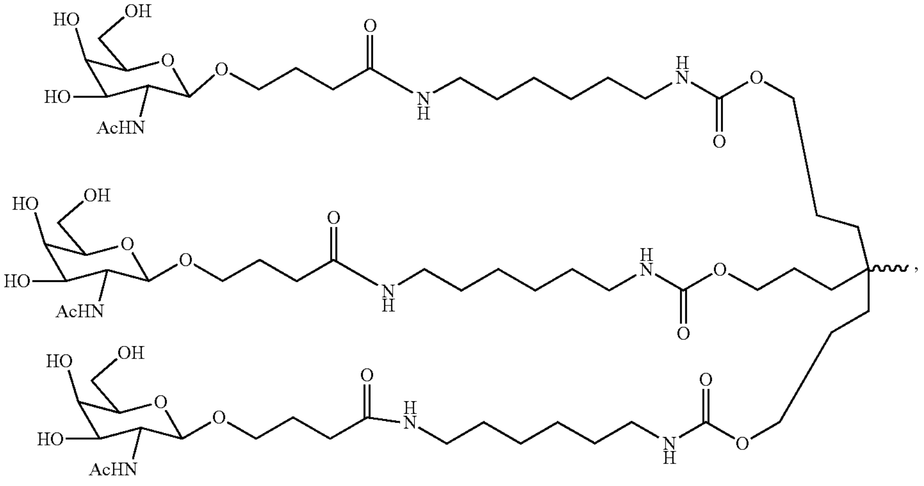

-continued
Formula X
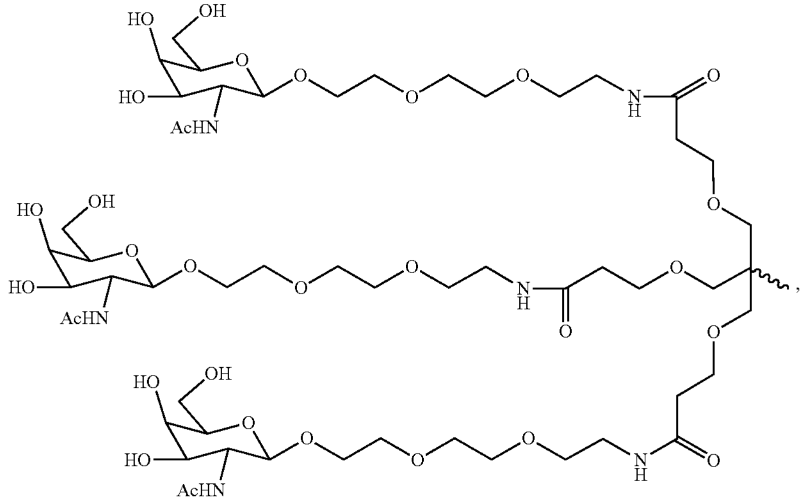
Formula XI
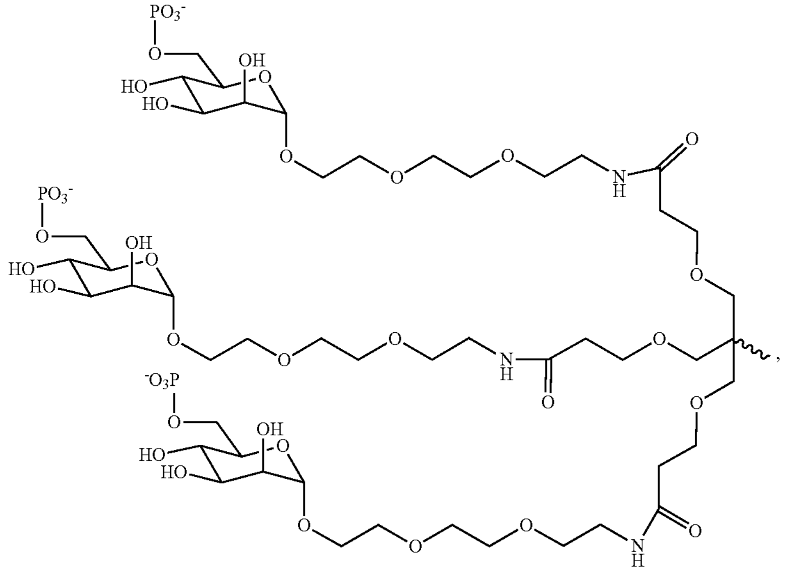

-continued
Formula XII
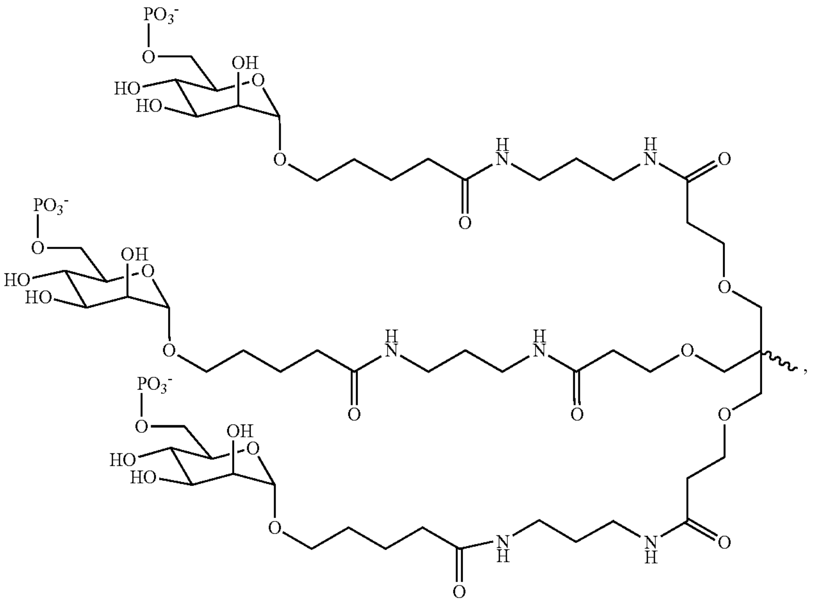
Formula XIII
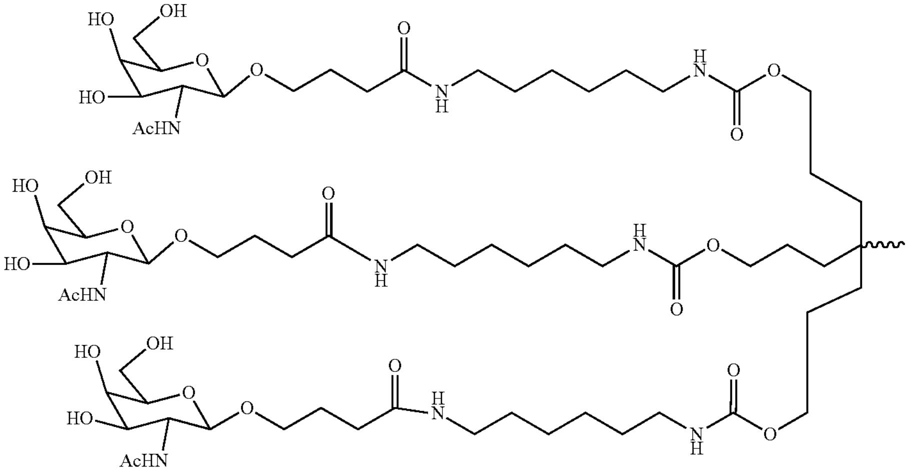
Formula XIV
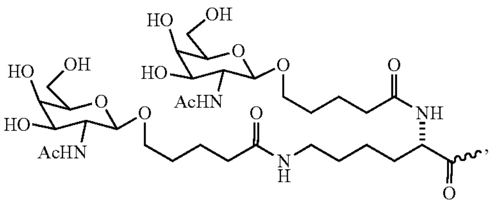
Formula XV
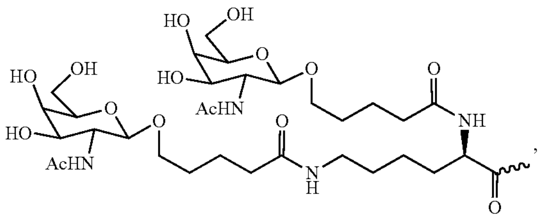
Formula XVI
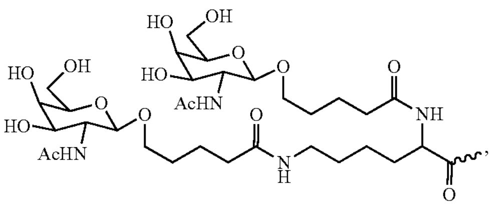
Formula XVII
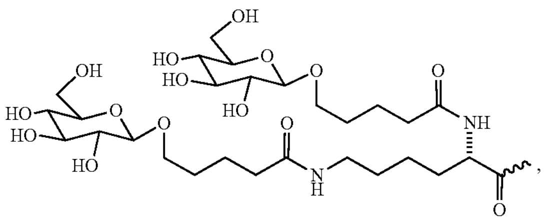

-continued
Formula XVIII
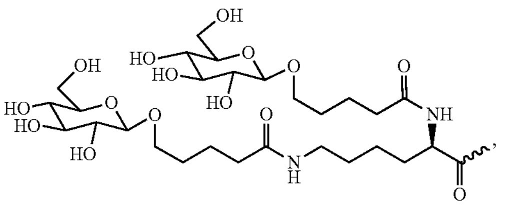
Formula XIX
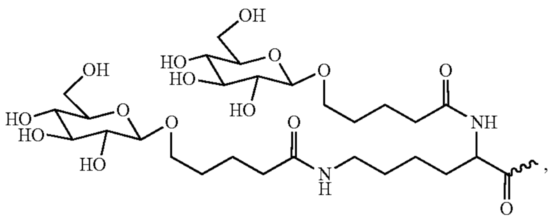
Formula XX
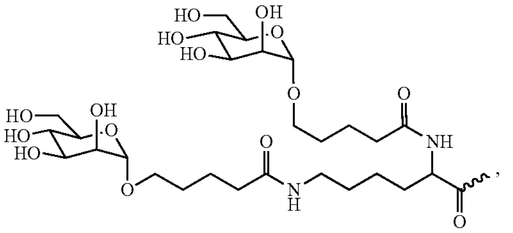
Formula XXI
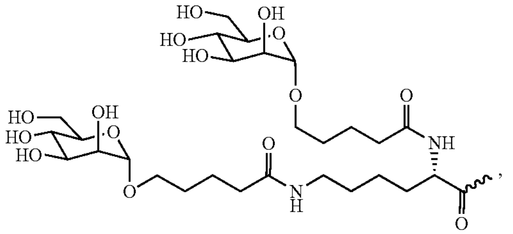
Formula XXII
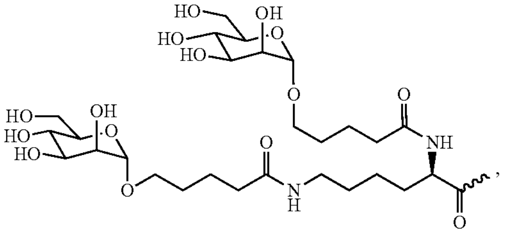
Formula XXIII
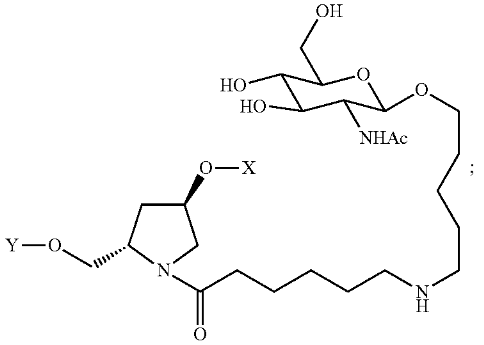
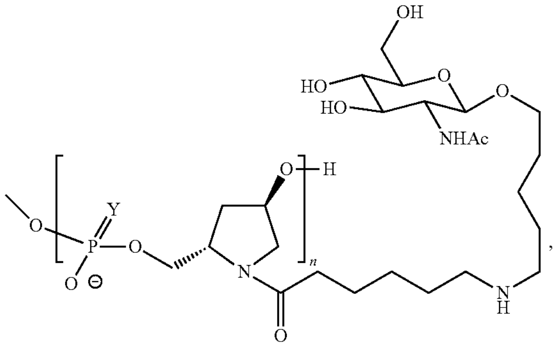
wherein Y is O or S and n is 3-6 (Formula XXIV);

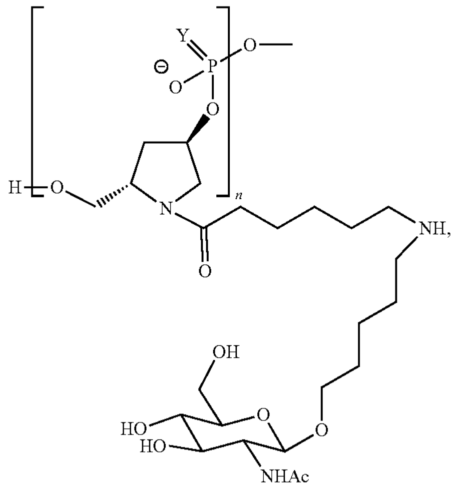
wherein Y is O or S and n is 3-6 (Formula XXV);
Formula XXVI
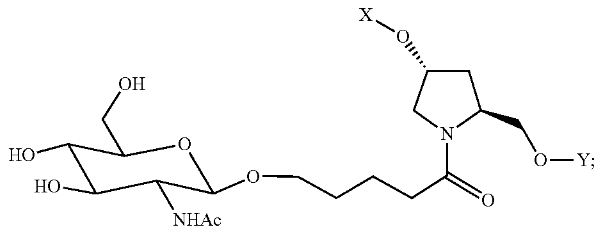
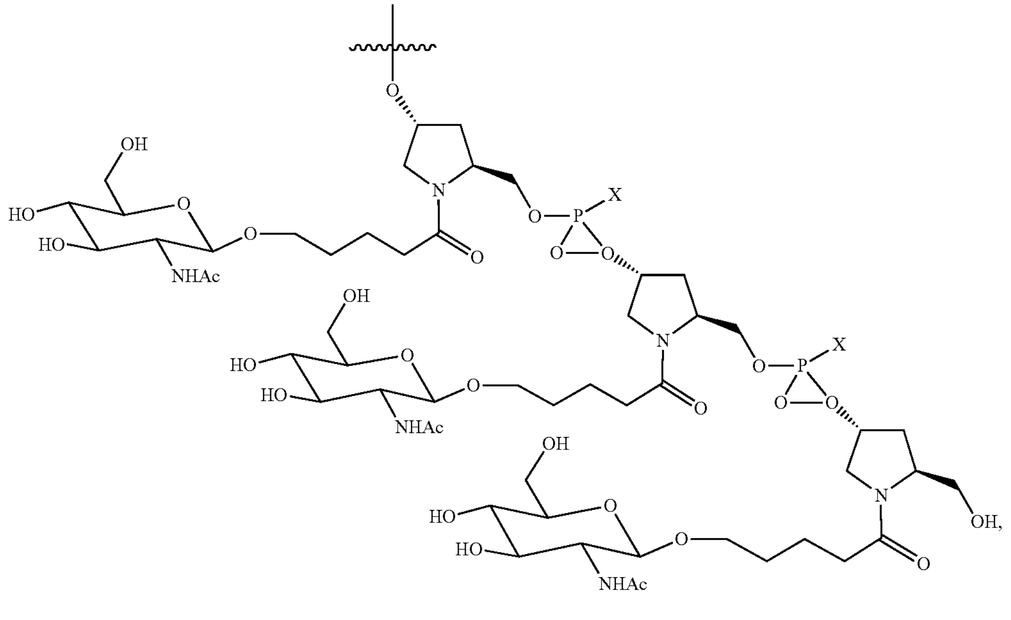
wherein X is 0 or S (Formula XXVII);

Formula XXVII
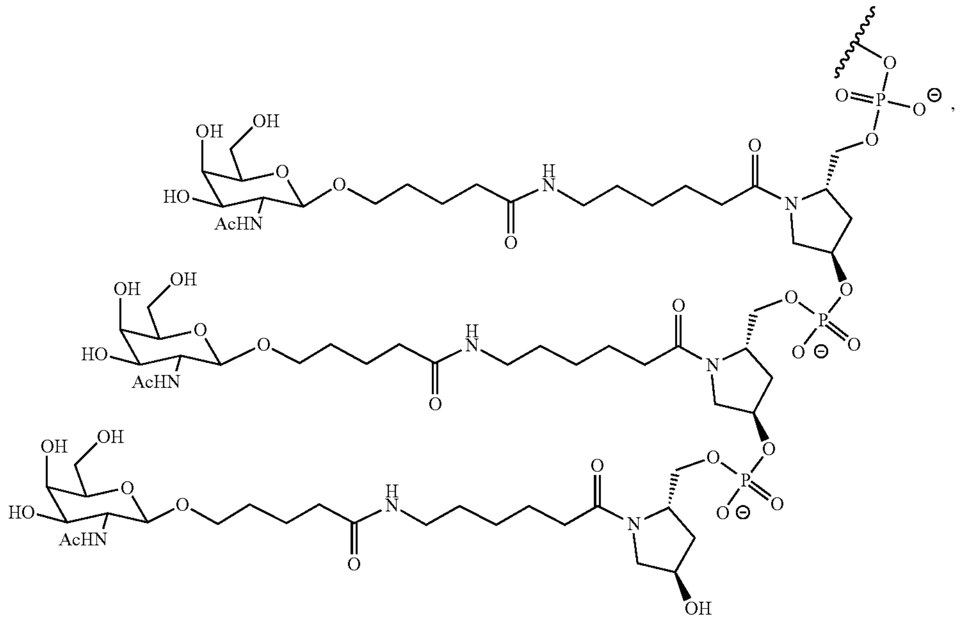
Formula XXIX
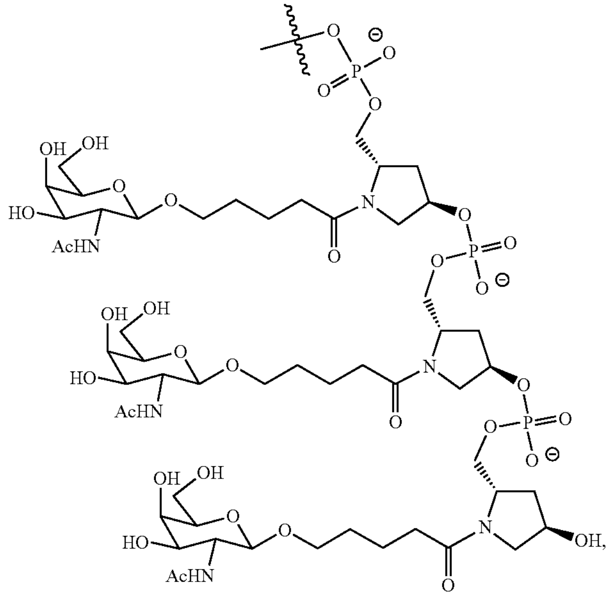

-continued
Formula XXX
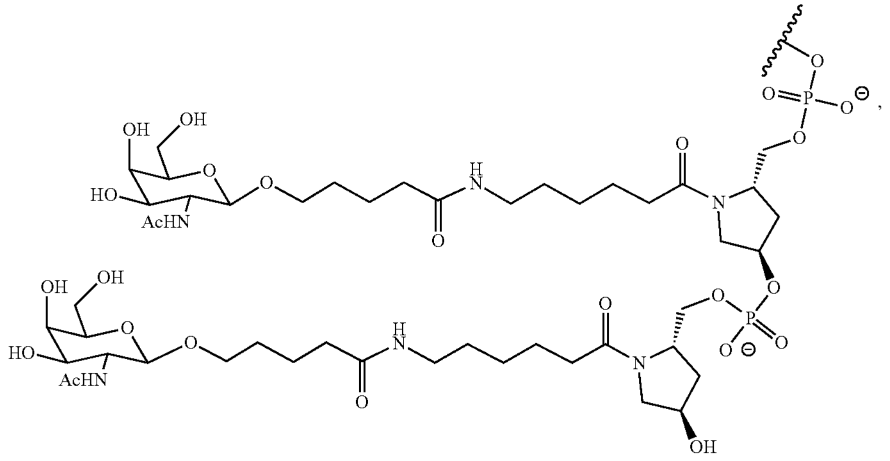
Formula XXXI
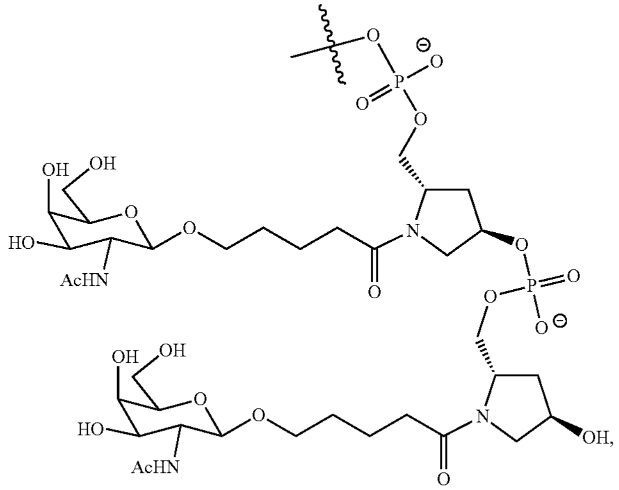
Formula XXXII
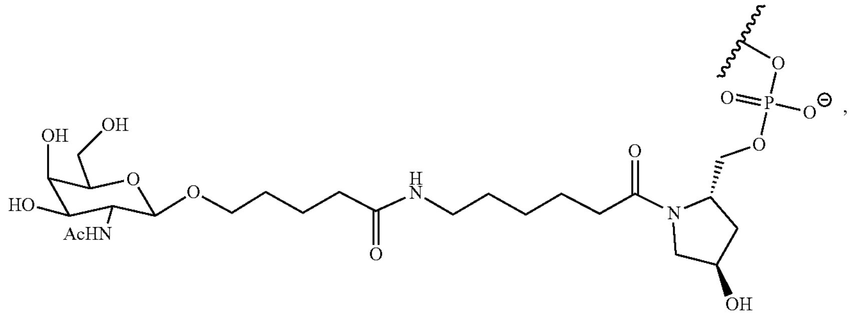
and
Formula XXXIII
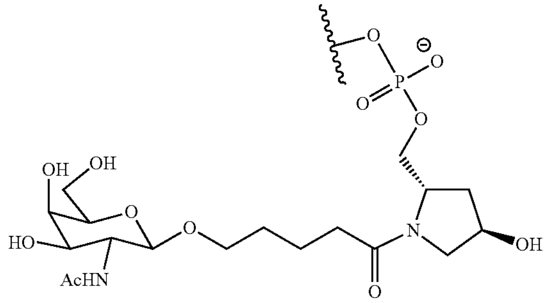

-continued

Formula XXXIV

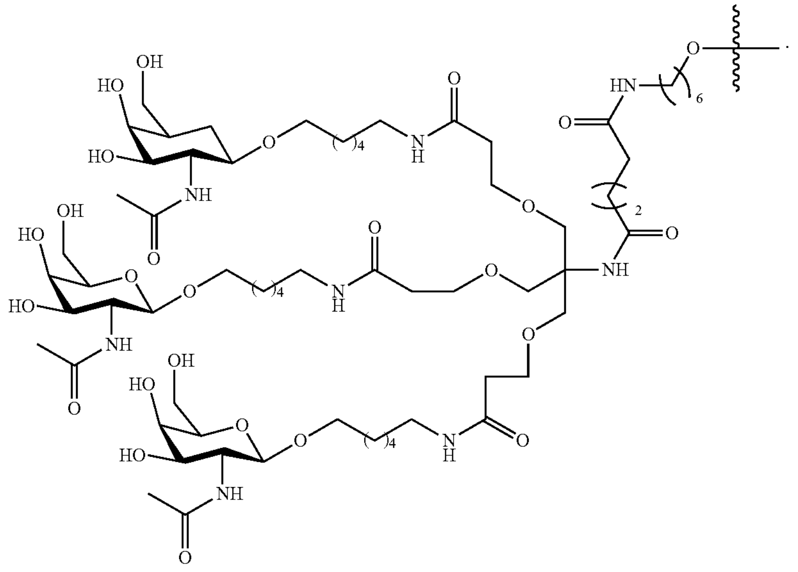

In another embodiment, a carbohydrate conjugate for use in the compositions and methods of the invention is a monosaccharide. In one embodiment, the monosaccharide is an N-acetylgalactosamine, such as Formula II

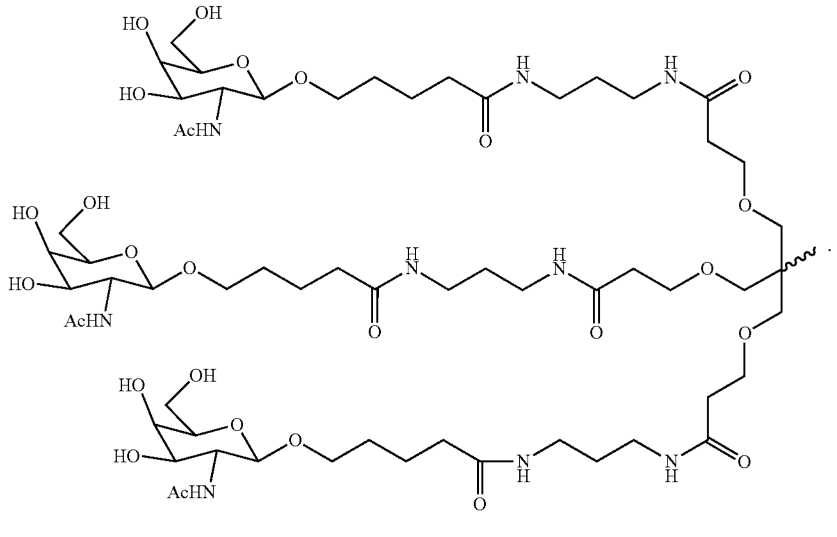

Another representative carbohydrate conjugate for use in the embodiments described herein includes, but is not limited to, (Formula XXXVI)

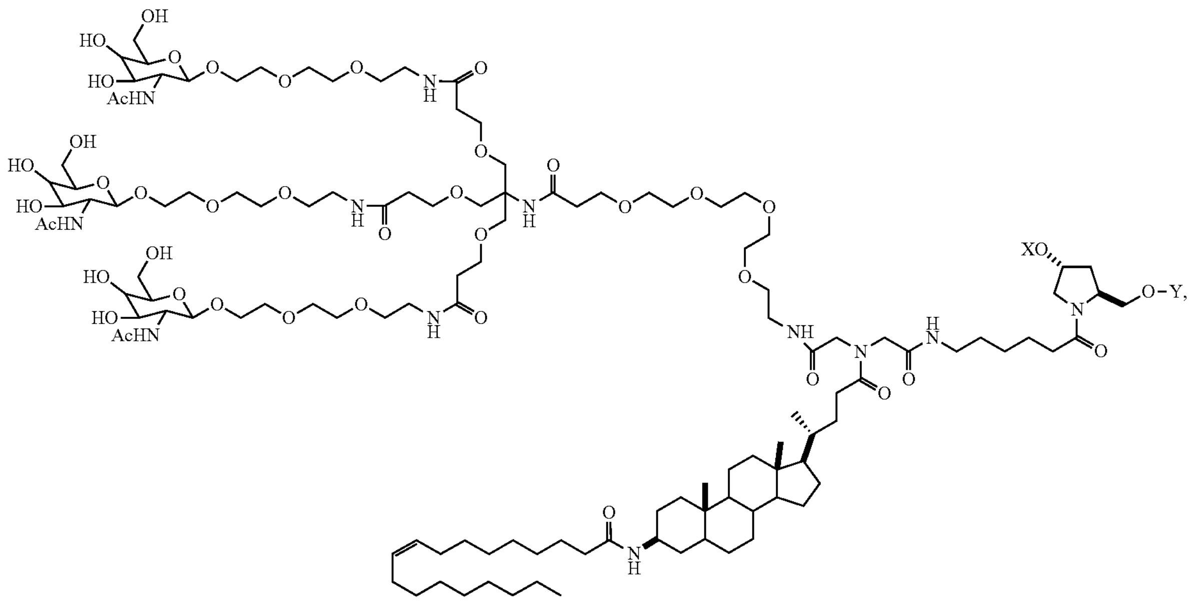

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent, e.g., the 5'end of the sense strand of a dsRNA agent, or the 5' end of one or both sense strands of a dual targeting RNAi agent as described herein. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVII)

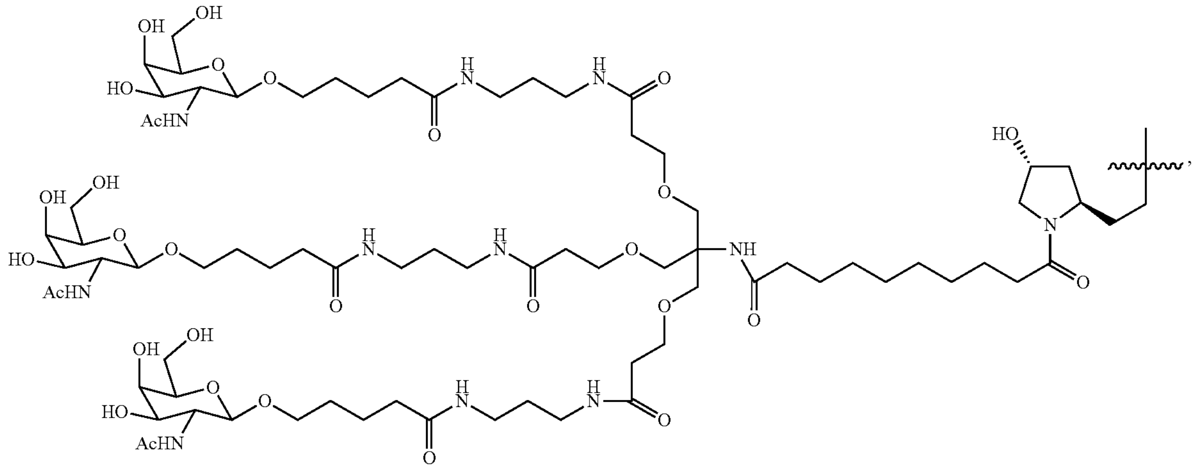

(Formula XXXVIII)

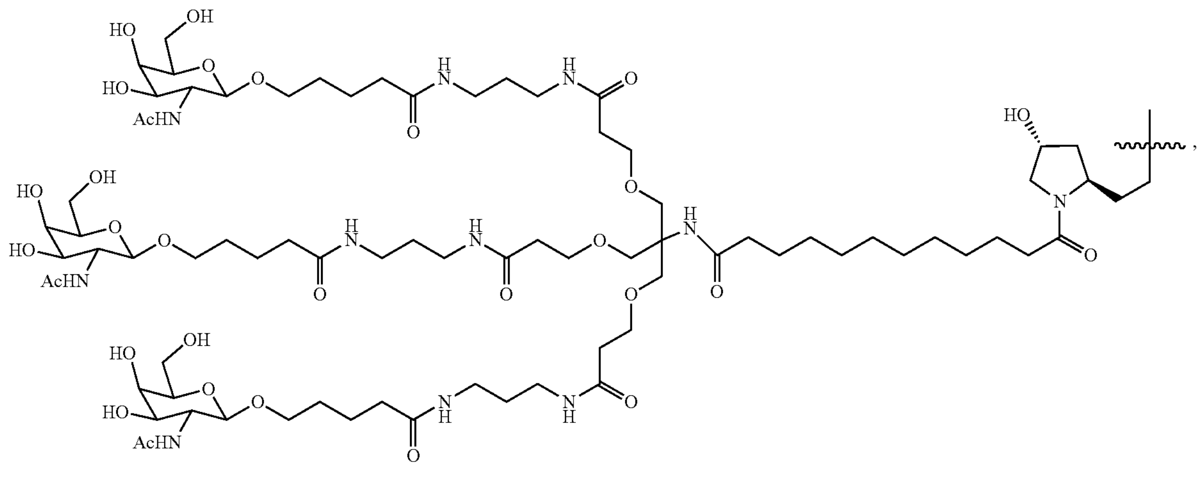

-continued
(Formula XXXIX)
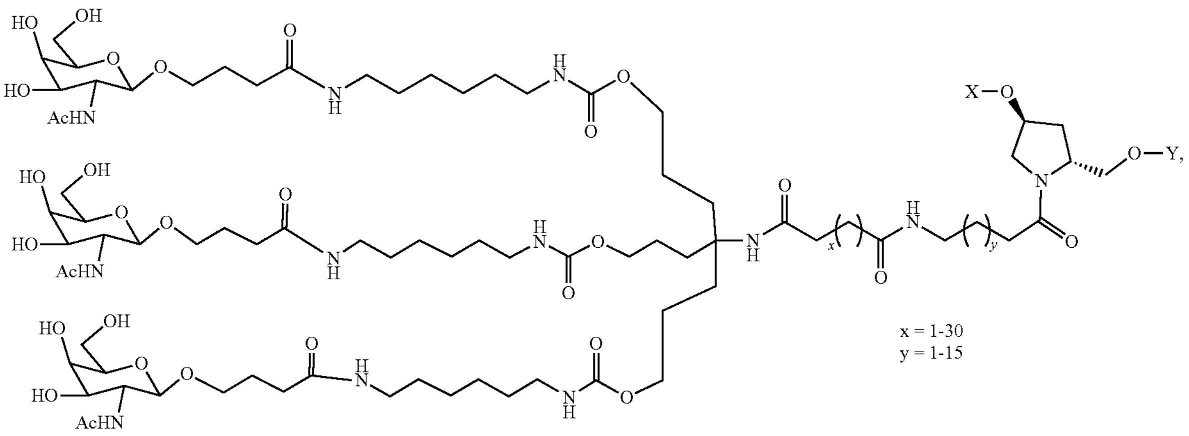
x = 1-30
y = 1-15
(Formula XL)
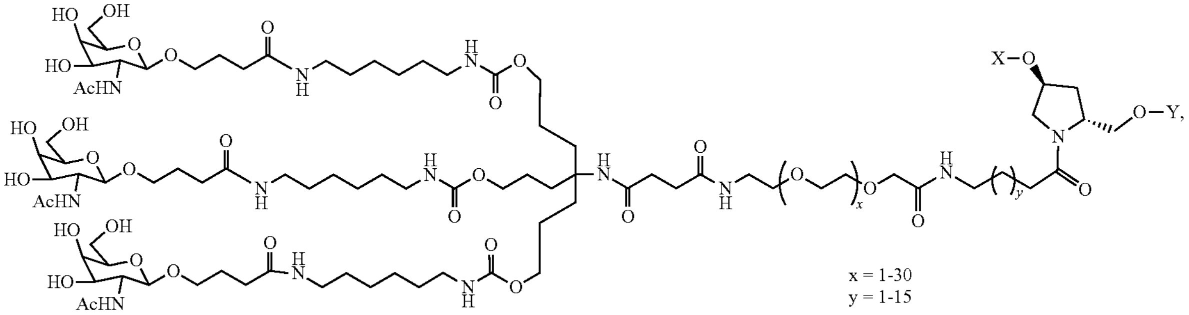
x = 1-30
y = 1-15
(Formula XLI)
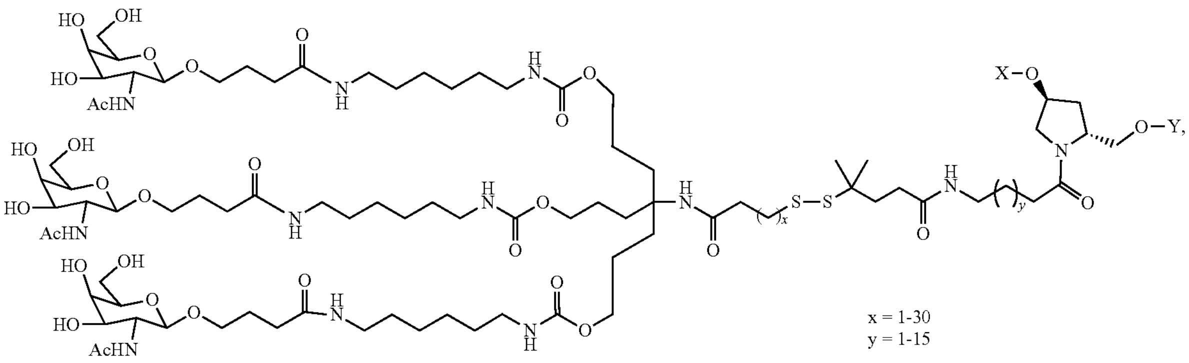
x = 1-30
y = 1-15
(Formula XLII)
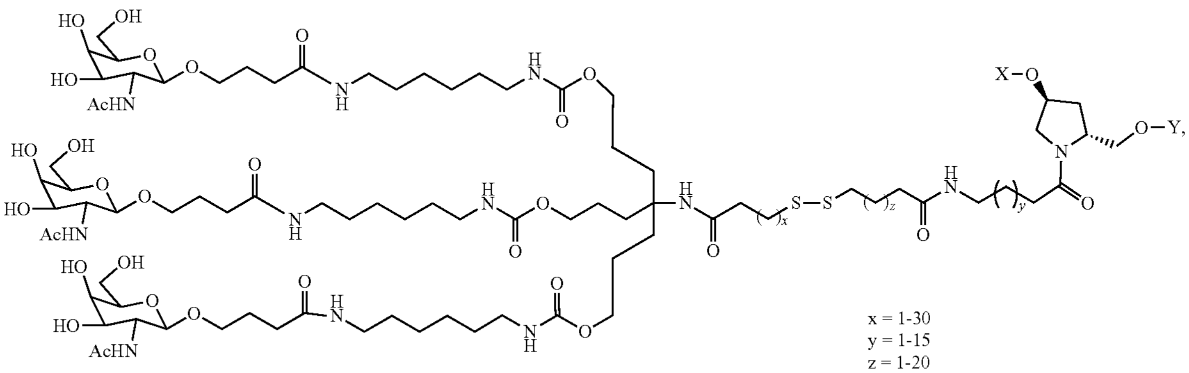
x = 1-30
y = 1-15
z = 1-20

-continued (Formula XLIII)

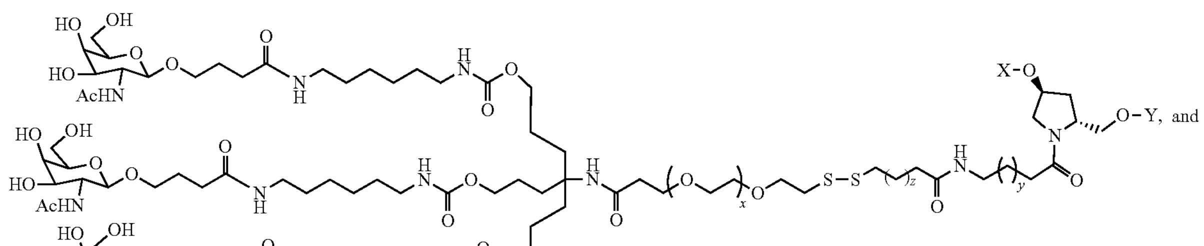

x = 1-30
y = 1-15
z = 1-20

(Formula XLIV)

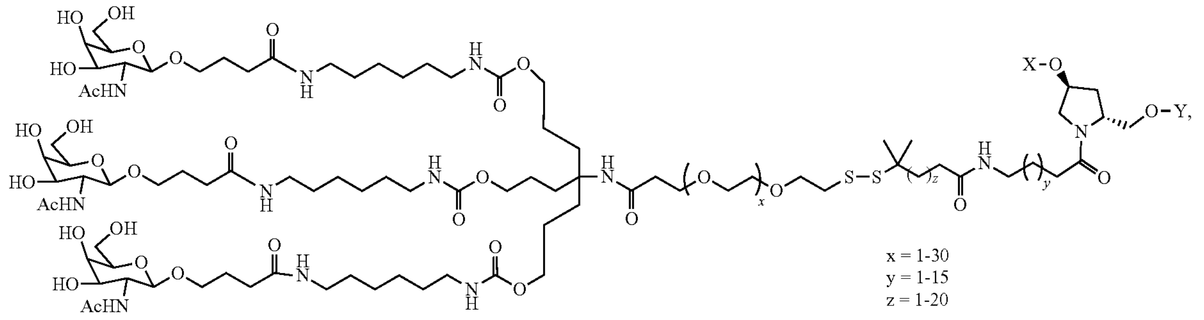

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

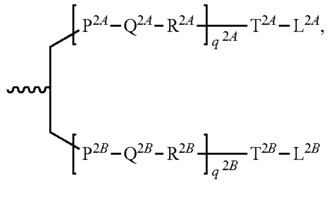

Formula XLVI

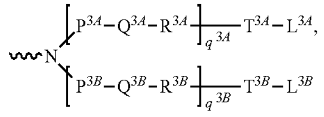

Formula XLVII

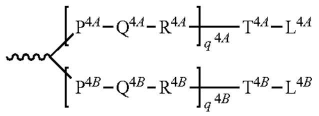

-continued

Formula XLVIII

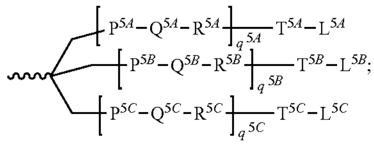

wherein:

q2A, q2B, q3A, q3B, q4A, q4B, q5A, q5B and q5C represent independently for each occurrence 0-20 and wherein the repeating unit can be the same or different;

$p^{2A}$, $p^{2B}$, $p^{3A}$, $p^{3B}$, $p^{4A}$, $p^{4B}$, $p^{5A}$, $p^{5B}$, $p^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC (O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, N(RN), C(R')=C(R"), C≡C or C (O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O) O, C(O)NH, NHCH($R^a$)C (O), —C(O)—CH($R^a$)—NH—, CO, CH=N—O,

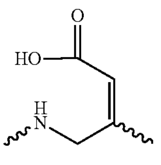
,
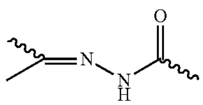
,

-continued

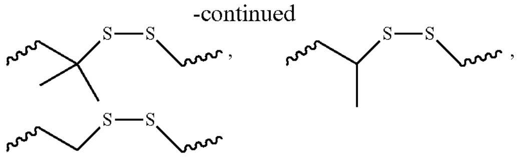

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

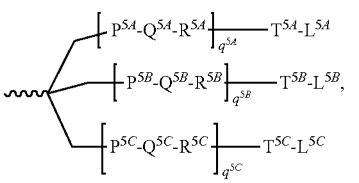

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. Patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Nat. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject susceptible to or diagnosed with a CPB2 associated disorder, e.g., a disorder associated with thrombosis, such as plasminogen deficiency) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya,Y., et al (2005) *J. Neurophysiol.* 93:594-602). Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178).

In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol* 327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), “solid nucleic acid lipid particles” (Zimmermann, T S, et al (2006) *Nature* 441:111-114), cardiolipin (Chien, P Y, et al (2005) Cancer *Gene Ther.* 12:321-328; Pal, A, et al (2005) *Int J. Oncol.* 26:1087-1091), polyethyleneimine (Bonnet M E, et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the CPB2 gene can be expressed from transcription units inserted into DNA or RNA vectors (see, e.g., Couture, A, et al., TIG. (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for preventing or treating a CPB2 associated disorder, e.g., a disorder associated with thrombosis. Non-limiting examples of CPB2-associated diseases or disorders include, plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

The pharmaceutical compositions are formulated based on the mode of delivery. One example is compositions that are formulated for systemic administration via parenteral delivery, e.g., by subcutaneous (SC), intramuscular (IM), or intravenous (IV) delivery. The pharmaceutical compositions of the invention may be administered in dosages sufficient to inhibit expression of a CPB2 gene.

The pharmaceutical compositions of the invention may be administered in dosages sufficient to inhibit expression of a CPB2 gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every month, once every 3-6 months, or once a year. In certain embodiments, the iRNA is administered about once per month to about once per six months.

After an initial treatment regimen, the treatments can be administered on a less frequent basis. Duration of treatment can be determined based on the severity of disease.

In other embodiments, a single dose of the pharmaceutical compositions can be long lasting, such that doses are administered at not more than 1, 2, 3, or 4 month intervals. In some embodiments of the invention, a single dose of the pharmaceutical compositions of the invention is administered about once per month. In other embodiments of the invention, a single dose of the pharmaceutical compositions of the invention is administered quarterly (i.e., about every three months). In other embodiments of the invention, a single dose of the pharmaceutical compositions of the invention is administered twice per year (i.e., about once every six months).

The skilled artisan will appreciate that certain factors can influence the dosage and timing required to effectively treat a subject, including but not limited to mutations present in the subject, previous treatments, the general health or age of the subject, and other diseases present. Moreover, treatment of a subject with a prophylactically or therapeutically effective amount, as appropriate, of a composition can include a single treatment or a series of treatments.

The iRNA can be delivered in a manner to target a particular tissue (e.g., hepatocytes or eyes).

Pharmaceutical compositions of the present invention include, but are not limited to, solutions, emulsions, and liposome-containing formulations. These compositions can be generated from a variety of components that include, but are not limited to, preformed liquids, self-emulsifying solids, and self-emulsifying semisolids. Formulations include those that target the liver.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers.

A. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution either in the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic, and amphoteric (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, NY, volume 1, p. 285).

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives, and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

The application of emulsion formulations via dermatological, oral, and parenteral routes, and methods for their manufacture have been reviewed in the literature (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

ii. Microemulsions

In one embodiment of the present invention, the compositions of iRNAs and nucleic acids are formulated as microemulsions. A microemulsion can be defined as a system of water, oil, and amphiphile which is a single optically isotropic and thermodynamically stable liquid solution (see e.g., Ansel's Pharmaceutical Dosage Forms and Drug Delivery Systems, Allen, LV., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215).

iii. Microparticles

An iRNA of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers and their use in manufacture of pharmaceutical compositions and delivery of pharmaceutical agents are well known in the art.

v. Excipients

In contrast to a carrier compound, a "pharmaceutical carrier" or "excipient" is a pharmaceutically acceptable solvent, suspending agent, or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Such agent are well known in the art.

vi. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings, or aromatic substances, and the like which do not deleteriously interact with the nucleic acid(s) of the formulation.

Aqueous suspensions can contain substances which increase the viscosity of the suspension including, for example, sodium carboxymethylcellulose, sorbitol, or dextran. The suspension can also contain stabilizers.

In some embodiments, pharmaceutical compositions featured in the invention include (a) one or more iRNA and (b) one or more agents which function by a non-iRNA mechanism and which are useful in treating a CPB2 associated disorder, e.g., a disorder associated with thrombosis, such as plasminogen deficiency.

Toxicity and prophylactic efficacy of such compounds can be determined by standard pharmaceutical procedures in cell cultures or experimental animals, e.g., for determining the LD50 (the dose lethal to 50% of the population) and the ED50 (the dose prophylactically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50, preferably an ED80 or ED90, with little or no toxicity. The dosage can vary within this range depending upon the dosage form employed and the route of administration utilized. For any compound used in the methods featured in the invention, the prophylactically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) or higher levels of inhibition as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents used for the prevention or treatment of a CPB2 associated disorder, e.g., a disorder associated with thrombosis, such as plasminogen deficiency. In any event, the administering physician can adjust the amount and timing of iRNA administration on the basis of results observed using standard measures of efficacy known in the art or described herein.

VI. Methods for Inhibiting CPB2 Expression

The present invention also provides methods of inhibiting expression of a CPB2 gene in a cell. The methods include contacting a cell with an RNAi agent, e.g., double stranded RNA agent, in an amount effective to inhibit expression of CPB2 in the cell, thereby inhibiting expression of CPB2 in the cell.

Contacting of a cell with an iRNA, e.g., a double stranded RNA agent, may be done in vitro or in vivo. Contacting a cell in vivo with the iRNA includes contacting a cell or group of cells within a subject, e.g., a human subject, with the iRNA. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest.

The term "inhibiting," as used herein, is used interchangeably with "reducing," "silencing," "downregulating", "suppressing", and other similar terms, and includes any level of inhibition.

The phrase "inhibiting expression of a CPB2" is intended to refer to inhibition of expression of any CPB2 gene (such as, e.g., a mouse CPB2 gene, a rat CPB2 gene, a monkey CPB2 gene, or a human CPB2 gene) as well as variants or mutants of a CPB2 gene. Thus, the CPB2 gene may be a wild-type CPB2 gene, a mutant CPB2 gene, or a transgenic CPB2 gene in the context of a genetically manipulated cell, group of cells, or organism.

"Inhibiting expression of a CPB2 gene" includes any level of inhibition of a CPB2 gene, e.g., at least partial suppression of the expression of a CPB2 gene. The expression of the CPB2 gene may be assessed based on the level, or the change in the level, of any variable associated with CPB2 gene expression, e.g., CPB2 mRNA level or CPB2 protein level. This level may be assessed in an individual cell or in a group of cells, including, for example, a sample derived from a subject. It is understood that CPB2 is expressed predominantly in the liver, but also in the brain, gall bladder, heart, and kidney, and is present in circulation.

Inhibition may be assessed by a decrease in an absolute or relative level of one or more variables that are associated with CPB2 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a CPB2 gene is inhibited by at least 50%, 55%, 60%, 65%, 70%, 75%, 80%, 85%, 90%, or 95%, or to below the level of detection of the assay. In preferred embodiments, expression of a CPB2 gene is inhibited by at least 70%. It is further understood that inhibition of CPB2 expression in certain tissues, e.g., in liver, without a significant inhibition of expression in other tissues, e.g., brain, may be desirable. In preferred embodiments, expression level is determined using the assay method provided in Example 2 with a 10 nM siRNA concentration in the appropriate species matched cell line.

In certain embodiments, inhibition of expression in vivo is determined by knockdown of the human gene in a rodent expressing the human gene, e.g., an AAV-infected mouse expressing the human target gene (i.e., CPB2), e.g., when administered a single dose at 3 mg/kg at the nadir of RNA expression. Knockdown of expression of an endogenous gene in a model animal system can also be determined, e.g., after administration of a single dose at 3 mg/kg at the nadir of RNA expression. Such systems are useful when the nucleic acid sequence of the human gene and the model animal gene are sufficiently close such that the human iRNA provides effective knockdown of the model animal gene. RNA expression in liver is determined using the PCR methods provided in Example 2.

Inhibition of the expression of a CPB2 gene may be manifested by a reduction of the amount of mRNA expressed by a first cell or group of cells (such cells may be present, for example, in a sample derived from a subject) in which a CPB2 gene is transcribed and which has or have been treated (e.g., by contacting the cell or cells with an iRNA of the invention, or by administering an iRNA of the invention to a subject in which the cells are or were present) such that the expression of a CPB2 gene is inhibited, as compared to a second cell or group of cells substantially identical to the first cell or group of cells but which has not or have not been so treated (control cell(s) not treated with an iRNA or not treated with an iRNA targeted to the gene of interest). In preferred embodiments, the inhibition is assessed by the method provided in Example 2 using a 10 nM siRNA concentration in the species matched cell line and expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

In other embodiments, inhibition of the expression of a CPB2 gene may be assessed in terms of a reduction of a parameter that is functionally linked to CPB2 gene expression, e.g., CPB2 protein level in blood or serum from a subject. CPB2 gene silencing may be determined in any cell expressing CPB2, either endogenous or heterologous from an expression construct, and by any assay known in the art.

Inhibition of the expression of a CPB2 protein may be manifested by a reduction in the level of the CPB2 protein that is expressed by a cell or group of cells or in a subject sample (e.g., the level of protein in a blood sample derived from a subject). As explained above, for the assessment of mRNA suppression, the inhibition of protein expression levels in a treated cell or group of cells may similarly be expressed as a percentage of the level of protein in a control cell or group of cells, or the change in the level of protein in a subject sample, e.g., blood or serum derived therefrom.

A control cell, a group of cells, or subject sample that may be used to assess the inhibition of the expression of a CPB2 gene includes a cell, group of cells, or subject sample that has not yet been contacted with an RNAi agent of the invention. For example, the control cell, group of cells, or subject sample may be derived from an individual subject (e.g., a human or animal subject) prior to treatment of the subject with an RNAi agent or an appropriately matched population control.

The level of CPB2 mRNA that is expressed by a cell or group of cells may be determined using any method known in the art for assessing mRNA expression. In one embodiment, the level of expression of CPB2 in a sample is determined by detecting a transcribed polynucleotide, or portion thereof, e.g., mRNA of the CPB2 gene. RNA may be extracted from cells using RNA extraction techniques including, for example, using acid phenol/guanidine isothiocyanate extraction (RNAzol B; Biogenesis), RNeasy® RNA preparation kits (Qiagen®) or PAXgene™ (PreAnalytix™, Switzerland). Typical assay formats utilizing ribonucleic acid hybridization include nuclear run-on assays, RT-PCR, RNase protection assays, northern blotting, in situ hybridization, and microarray analysis.

In some embodiments, the level of expression of CPB2 is determined using a nucleic acid probe. The term "probe", as used herein, refers to any molecule that is capable of selectively binding to a specific CPB2. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to CPB2 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of CPB2 mRNA.

An alternative method for determining the level of expression of CPB2 in a sample involves the process of nucleic acid amplification or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Nat. Acad. Sci. USA* 88:189-193), self sustained sequence replication (Guatelli et al. (1990) *Proc. Nat. Acad. Sci. USA* 87:1874-1878), transcriptional amplification system (Kwoh et al. (1989) *Proc. Nat. Acad. Sci. USA* 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of CPB2 is determined by quantitative fluorogenic RT-PCR (i.e., the TaqMan™ System). In preferred embodiments, expression level is determined by the method provided in Example 2 using a 10 nM siRNA concentration in the species matched cell line.

The expression levels of CPB2 mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of CPB2 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein. In preferred embodiments, expression level is determined by the method provided in Example 2 using a 10 nM siRNA concentration in the species matched cell line.

The level of CPB2 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention are assessed by a decrease in CPB2 mRNA or protein level (e.g., in a liver biopsy).

In some embodiments of the methods of the invention, the iRNA is administered to a subject such that the iRNA is delivered to a specific site within the subject. The inhibition of expression of CPB2 may be assessed using measurements of the level or change in the level of CPB2 mRNA or CPB2 protein in a sample derived from fluid or tissue from the specific site within the subject (e.g., liver, eye or blood).

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

VII. Prophylactic and Treatment Methods of the Invention

The present invention also provides methods of using an iRNA of the invention or a composition containing an iRNA of the invention to inhibit expression of CPB2, thereby preventing or treating a CPB2 associated disorder, e.g., a disorder associated with thrombosis. Non-limiting examples of CPB2-associated diseases or disorders include, plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

In the methods of the invention the cell may be contacted with the siRNA in vitro or in vivo, i.e., the cell may be within a subject.

A cell suitable for treatment using the methods of the invention may be any cell that expresses a CPB2 gene, e.g., a liver cell, an eye cell, a brain cell, a gall bladder cell, a heart cell, or a kidney cell, but preferably a liver cell. A cell suitable for use in the methods of the invention may be a mammalian cell, e.g., a primate cell (such as a human cell, including human cell in a chimeric non-human animal, or a non-human primate cell, e.g., a monkey cell or a chimpanzee cell), or a non-primate cell. In certain embodiments, the cell is a human cell, e.g., a human liver cell. In the methods of the invention, CPB2 expression is inhibited in the cell by at least 50, 55, 60, 65, 70, 75, 80, 85, 90, or 95, or to a level below the level of detection of the assay.

The in vivo methods of the invention may include administering to a subject a composition containing an iRNA, where the iRNA includes a nucleotide sequence that is complementary to at least a part of an RNA transcript of the CPB2 gene of the mammal to which the RNAi agent is to be administered. The composition can be administered by any means known in the art including, but not limited to, oral, intraperitoneal, or parenteral routes, including intracranial (e.g., intraventricular, intraparenchymal, and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intramuscular injection.

In one aspect, the present invention also provides methods for inhibiting the expression of a CPB2 gene in a mammal. The methods include administering to the mammal a composition comprising a dsRNA that targets a CPB2 gene in a cell of the mammal and maintaining the mammal for a time sufficient to obtain degradation of the mRNA transcript of the CPB2 gene, thereby inhibiting expression of the CPB2 gene in the cell. Reduction in gene expression can be assessed by any methods known in the art and by methods, e.g. qRT-PCR, described herein, e.g., in Example 2. Reduction in protein production can be assessed by any methods known it the art, e.g. ELISA. In certain embodiments, a puncture liver biopsy sample serves as the tissue material for monitoring the reduction in the CPB2 gene or protein expression. In other embodiments, a blood sample serves as the subject sample for monitoring the reduction in the CPB2 protein expression.

The present invention further provides methods of treatment in a subject in need thereof, e.g., a subject diagnosed with a CPB2 associated disorder, such as a disorder associated with thrombosis, e.g., post-thrombotic syndrome or plasminogen deficiency, e.g., type I plasminogen deficiency or type II plasminogen deficiency.

The present invention further provides methods of prophylaxis in a subject in need thereof. The treatment methods of the invention include administering an iRNA of the invention to a subject, e.g., a subject that would benefit from a reduction of CPB2 expression, in a prophylactically effective amount of an iRNA targeting a CPB2 gene or a pharmaceutical composition comprising an iRNA targeting a CPB2 gene.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from an inhibition of CPB2 gene expression are subjects susceptible to or diagnosed with a CPB2 associated disorder, such as a disorder associated with thrombosis (such as, e.g., post-thrombotic syndrome or plasminogen deficiency, e.g., type I plasminogen deficiency or type II plasminogen deficiency.

In an embodiment, the method includes administering a composition featured herein such that expression of the target CPB2 gene is decreased, such as for about 1, 2, 3, 4, 5, 6, 1-6, 1-3, or 3-6 months per dose. In certain embodiments, the composition is administered once every 3-6 months.

Preferably, the iRNAs useful for the methods and compositions featured herein specifically target RNAs (primary or processed) of the target CPB2 gene. Compositions and methods for inhibiting the expression of these genes using iRNAs can be prepared and performed as described herein.

Administration of the iRNA according to the methods of the invention may result prevention or treatment of a CPB2 associated disorder, e.g., a disorder associated with thrombosis, e.g., post-thrombotic syndrome or plasminogen deficiency, e.g., type I plasminogen deficiency or type II plasminogen deficiency.

Subjects can be administered a therapeutic amount of iRNA, such as about 0.01 mg/kg to about 200 mg/kg.

The iRNA is preferably administered subcutaneously, i.e., by subcutaneous injection. One or more injections may be used to deliver the desired dose of iRNA to a subject. The injections may be repeated over a period of time.

The administration may be repeated on a regular basis. In certain embodiments, after an initial treatment regimen, the treatments can be administered on a less frequent basis. A repeat-dose regimen may include administration of a therapeutic amount of iRNA on a regular basis, such as once per month to once a year. In certain embodiments, the iRNA is administered about once per month to about once every three months, or about once every three months to about once every six months.

This invention is further illustrated by the following examples which should not be construed as limiting. The entire contents of all references, patents and published patent applications cited throughout this application, as well as the informal Sequence Listing, are hereby incorporated herein by reference.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

siRNA Design

A set of siRNAs targeting the human CPB2 gene (human: NCBI refseqID NM_001872.5; NCBI GeneID: 1361) was designed using custom R and Python scripts. The human NM_001872 REFSEQ mRNA, has a length of 1724 bases.

A detailed list of the unmodified CPB2 sense and antisense strand nucleotide sequences is shown in Table 2. A detailed list of the modified CPB2 sense and antisense strand nucleotide sequences is shown in Table 3.

siRNA Synthesis siRNAs were synthesized and annealed using routine methods known in the art.

Briefly, siRNA sequences were synthesized at 1 μmol scale on a Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, WI) and Hongene (China). 2'F 2'-O-Methyl, GNA (glycol nucleic acids), 5'phosphate and other modifications were introduced using the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, MA, USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 μL Aqueous Methylamine reagents at 60° C. for 20 minutes. For sequences containing 2' ribo residues (2'-OH) that are protected with a tert-butyl dimethyl silyl (TBDMS) group, a second step deprotection was performed using TEA.3HF (triethylamine trihydro fluoride) reagent. To the methylamine deprotection solution, 200 uL of dimethyl sulfoxide (DMSO) and 300 ul TEA.3HF reagent was added and the solution was incubated for additional 20 min at 60° C. At the end of cleavage and deprotection step, the synthesis plate was allowed to come to room temperature and was precipitated by addition of 1 mL of acetontile: ethanol mixture (9:1). The plates were cooled at −80 C for 2 hrs, superanatant decanted carefully with the aid of a multi channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples by IEX chromatography to determine purity.

Annealing of single strands was performed on a Tecan liquid handling robot. Equimolar mixture of sense and antisense single strands were combined and annealed in 96 well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 M in 1×PBS and then submitted for in vitro screening assays.

Example 2. In Vitro Screening Methods

Cell Culture and 384-Well Transfections

Hep3b cells (ATCC, Manassas, VA) were grown to near confluence at 37° C. in an atmosphere of 5% $CO_2$ in Eagle's Minimum Essential Medium (Gibco) supplemented with 10% FBS (ATCC) before being released from the plate by trypsinization. For mouse cross reactive duplexes, primary mouse hepatocytes (PMH) were freshly isolated less than 1 hour prior to transfections and grown in primary hepatocyte media. For both Hep3B and PMH, transfection was carried out by adding 14.8 μl of Opti-MEM plus 0.2 μl of Lipofectamine RNAiMax per well (Invitrogen, Carlsbad CA. cat #13778-150) to 5 μl of each siRNA duplex to an individual well in a 96-well plate. The mixture was then incubated at room temperature for 15 minutes. Eighty μl of complete growth media without antibiotic containing ~2 ×104 Hep3B cells were then added to the siRNA mixture. Cells were incubated for 24 hours prior to RNA purification. Single dose experiments were performed at 10 nM and 0.1 nM final duplex concentration and dose response experiments were done using 8×5-fold serial dilutions over the range of 10 nM to 128 pM.

Total RNA Isolation Using DYNABEADS mRNA Isolation Kit (Invitrogen™, Part #: 610-12)

Cells were lysed in 75 μl of Lysis/Binding Buffer containing 3 μL of beads per well and mixed for 10 minutes on an electrostatic shaker. The washing steps were automated on a Biotek EL406, using a magnetic plate support. Beads were washed (in 90 L) once in Buffer A, once in Buffer B, and twice in Buffer E, with aspiration steps in between. Following a final aspiration, complete 10 μL RT mixture was added to each well, as described below.

cDNA Synthesis Using ABI High Capacity cDNA Reverse Transcription Kit (Applied Biosystems, Foster City, CA, Cat #4368813)

A master mix of 1 μl 10× Buffer, 0.4 μl 25× dNTPs, 1 μl Random primers, 0.5 μl Reverse Transcriptase, 0.5 μl RNase inhibitor and 6.6 μl of $H_2O$ per reaction were added per well. Plates were sealed, agitated for 10 minutes on an electrostatic shaker, and then incubated at 37 degrees C. for 2 hours. Following this, the plates were agitated at 80 degrees C. for 8 minutes.

Real Time PCR

Two microlitre (μl) of cDNA were added to a master mix containing 0.5 μl of human GAPDH TaqMan Probe (4326317E), 0.5 pl human CPB2 (Mm00490698_m1), 2 μl nuclease-free water and 5 μl Lightcycler 480 probe master mix (Roche Cat #04887301001) per well in a 384 well plates (Roche cat #04887301001). Real time PCR was done in a LightCycler480 Real Time PCR system (Roche).

To calculate relative fold change, data were analyzed using the ΔΔCt method and normalized to assays performed with cells transfected with 10 nM AD-1955, or mock transfected cells. $IC_{50}$s were calculated using a 4 parameter fit model using XLFit and normalized to cells transfected with AD-1955 or mock-transfected. The sense and antisense sequences of AD-1955 are: sense: cuuAcGcuGAGuAcuucGAdTsdT (SEQ ID NO: 33) and antisense UCGAAGuACUcAGCGuAAGdTsdT (SEQ ID NO: 34). Results from the screening are shown in Table 4.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3`-phosphate |
| Abs | beta-L-adenosine-3`-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3`-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3`-phosphate |
| Gbs | beta-L-guanosine-3`-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5 -methyluridine-3'-phosphate |
| ts | 2'-O-methyl-5 -methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (Hyp-(GalNAc-alkyl)3) |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphonate |
| (Aam) | 2`-O-(N-methylacetamide)adenosine-3`-phosphate |
| (Aams) | 2`-O-(N-methylacetamide)adenosine-3`-phosphorothioate |
| (Gam) | 2`-O-(N-methylacetamide)guanosine-3`-phosphate |
| (Gams) | 2`-O-(N-methylacetamide)guanosine-3`-phosphorothioate |
| (Tam) | 2`-O-(N-mcthylacetamide)thymidine-3`-phosphate |
| (Tams) | 2`-O-(N-methylacetamide)thymidine-3`-phosphorothioate |
| dA | 2`-deoxyadenosine-3`-phosphate |
| dAs | 2`-deoxyadenosine-3`-phosphorothioate |
| dC | 2`-deoxycytidine-3`-phosphate |
| dCs | 2`-deoxycytidine-3`-phosphorothioate |
| dG | 2`-deoxyguanosine-3`-phosphate |
| dGs | 2`-deoxyguanosine-3`-phosphorothioate |
| dT | 2`-deoxythymidine-3`-phosphate |
| dTs | 2`-deoxythymidine-3`-phosphorothioate |
| dU | 2`-deoxyuridine |
| dUs | 2`-deoxyuridine-3`-phosphorothioate |
| (Aeo) | 2`-O-methoxyethyladenosine-3`-phosphate |
| (Aeos) | 2`-O-methoxyethyladenosine-3`-phosphorothioate |
| (Geo) | 2`-O-methoxyethylguanosine-3`-phosphate |
| (Geos) | 2`-O-methoxyethylguanosine-3`-phosphorothioate |
| (Teo) | 2`-O-methoxyethyl-5-methyluridine-3`-phosphate |
| (Teos) | 2`-O-methoxyethyl-5-methyluridine-3`-phosphorothioate |
| (m5Ceo) | 2`-O-methoxyethyl-5-mcthylcytidinc-3`-phosphate |
| (m5Ceos) | 2`-O-methoxyethyl-5-methylcytidine-3`-phosphorothioate |
| (A3m) | 3-O-methyladenosine-2`-phosphate |

TABLE 1-continued

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| (A3mx) | 3`-O-methyl-xylofuranosyladenosine-2`-phosphate |
| (G3m) | 3`-O-methylguanosine-2`-phosphate |
| (G3mx) | 3`-O-methyl-xylofuranosylguanosine-2`-phosphate |
| (C3m) | 3`-O-methylcytidine-2`-phosphate |
| (C3mx) | 3`-O-methyl-xylofuranosylcytidine-2`-phosphate |
| (U3m) | 3`-O-methyluridine-2`-phosphate |
| U3mx) | 3`-O-methyl-xylofuranosyluridine-2`-phosphate |
| (m5Cam) | 2`-O-(N-methylacetamide)-5-methylcytidine-3`-phosphate |
| (m5Cams) | 2`-O-(N-methylacetamide)-5-methylcytidine-3`-phosphorothioate |
| (Chd) | 2'-O-hexadecyl-cytidine-3'-phosphate |
| (Chds) | 2'-O-hexadecyl-cytidine-3'-phosphorothioate |
| (Uhd) | 2'-O-hexadecyl-uridine-3'-phosphate |
| (Uhds) | 2'-O-hexadecyl-uridine-3'-phosphorothioate |
| (pshe) | Hydroxyethylphosphorothioate |
| (C2p) | cytidine-2`-phosphate |
| (G2p) | guanosine-2`-phosphate |

TABLE 2

Unmodified Sense and Antisense Strand Sequences of CPB2 dsRNA Agents

| Duplex Name | Sense Oligo Name | Sense Sequence 5' to 3' | Range | SEQ ID NO: | Antisense Oligo Name | Antisense Sequence 5' to 3' | Range | SEQ ID NO: |
|---|---|---|---|---|---|---|---|---|
| AD-206997.1 | A-409536.1 | CACGUGGAAAAGAAUCGAAU | 755-775 | 35 | A-409537.1 | AUUCGAUUCUUUUCCACGUGUA | 753-775 | 129 |
| AD-204191.2 | A-403936.1 | UUGGGCAUCAAAUAUUCGUUU | 1082-1102 | 36 | A-403937.1 | AAACGAAUAUUUGAUGCCCAAAU | 1080-1102 | 130 |
| AD-204195.1 | A-403944.1 | GCAUCAAAUAUUCGUUUACAA | 1086-1106 | 37 | A-403945.1 | UUGUAAACGAAUAUUUGAUGCCC | 1084-1106 | 131 |
| AD-204191.1 | A-403936.1 | UUGGGCAUCAAAUAUUCGUUU | 1082-1102 | 38 | A-403937.1 | AAACGAAUAUUUGAUGCCCAAAU | 1080-1102 | 132 |
| AD-204194.1 | A-403942.1 | GGCAUCAAAUAUUCGUUUACA | 1085-1105 | 39 | A-403943.1 | UGUAAACGAAUAUUUGAUGCCCA | 1083-1105 | 133 |
| AD-204193.2 | A-403940.1 | GGGCAUCAAAUAUUCGUUUAA | 1084-1104 | 40 | A-403941.1 | UUAAACGAAUAUUUGAUGCCCAA | 1082-1104 | 134 |
| AD-204193.1 | A-403940.1 | GGGCAUCAAAUAUUCGUUUAA | 1084-1104 | 41 | A-403941.1 | UUAAACGAAUAUUUGAUGCCCAA | 1082-1104 | 135 |
| AD-206996.1 | A-409534.1 | ACACGUGGAAAAAGAAUCGAA | 754-774 | 42 | A-409535.1 | UUCGAUUCUUUUCCACGUGUAG | 752-774 | 136 |
| AD-204192.1 | A-403938.1 | UGGGCAUCAAAUAUUCGUUUA | 1083-1103 | 43 | A-403939.1 | UAAACGAAUAUUUGAUGCCCAAA | 1081-1103 | 137 |
| AD-203386.1 | A-402326.1 | CUACAGAAUCUUACUACAACA | 191-211 | 44 | A-402327.1 | UGUUGUAGUAAGAUUCUGUAGAA | 189-211 | 138 |
| AD-206944.1 | A-409430.1 | AGGCACGUGGAUUUCUACAUA | 702-722 | 45 | A-409431.1 | UAUGUAGAAAUCCACGUGCCUCA | 700-722 | 139 |
| AD-207600.1 | A-410736.1 | UGAAUCAGUUUCCUUGGUUUU | 1413-1433 | 46 | A-410737.1 | AAAACCAAGGAAACUGAUUCAAC | 1411-1433 | 140 |
| AD-206998.1 | A-409538.1 | ACGUGGAAAAAGAAUCGAAUA | 756-776 | 47 | A-409539.1 | UAUUCGAUUCUUUUUCCACGUGU | 754-776 | 141 |
| AD-203564.1 | A-402682.1 | ACUAUGAACAGUAUCACUCAA | 423-443 | 48 | A-402683.1 | UUGAGUGAUACUGUUCAUAGUAC | 421-443 | 142 |
| AD-204194.2 | A-403942.1 | GGCAUCAAAUAUUCGUUUACA | 1085-1105 | 49 | A-403943.1 | UGUAAACGAAUAUUUGAUGCCCA | 1083-1105 | 143 |

TABLE 2-continued

| Unmodified Sense and Antisense Strand Sequences of CPB2 dsRNA Agents | | | | | | | | |
|---|---|---|---|---|---|---|---|---|
| Duplex Name | Sense Oligo Name | Sense Sequence 5' to 3' | Range | SEQ ID NO: | Antisense Oligo Name | Antisense Sequence 5' to 3' | Range | SEQ ID NO: |
| AD-204190.1 | A-403934.1 | UUUGGGCAUCAAAUAUUCGUU | 1081-1101 | 50 | A-403935.1 | AACGAAUAUUUGAUGCCCAAAUC | 1079-1101 | 144 |
| AD-204014.1 | A-403582.1 | AGCAUGCAUUCAUACUCCCAA | 878-898 | 51 | A-403583.1 | UUGGGAGUAUGAAUGCAUGCUGA | 876-898 | 145 |
| AD-206596.1 | A-408736.1 | AGCAGAAUUCCAUUUAACGUU | 324-344 | 52 | A-408737.1 | AACGUUAAAUGGAAUUCUGCUCA | 322-344 | 146 |
| AD-207367.1 | A-410272.1 | CAGAAAGUUUAUAUCUAGCUA | 1141-1161 | 53 | A-410273.1 | UAGCUAGAUAUAAACUUUCUGAG | 1139-1161 | 147 |
| AD-207362.1 | A-410262.1 | UGGCUCAGAAAGUUUAUAUCU | 1136-1156 | 54 | A-410263.1 | AGAUAUAAACUUUCUGAGCCACU | 1134-1156 | 148 |
| AD-206384.1 | A-408312.1 | UGGUAGCCAUCAUCCUCUAUA | 94-114 | 55 | A-408313.1 | UAUAGAGGAUGAUGGCUACCAGG | 92-114 | 149 |
| AD-207212.1 | A-409962.1 | AGCUUACAUCAGUAUGCACUA | 977-997 | 56 | A-409963.1 | UAGUGCAUACUGAUGUAAGCUUU | 975-997 | 150 |
| AD-203314.1 | A-402182.1 | CAGCAUGUCUUCGCGUUUCAA | 119-139 | 57 | A-402183.1 | UUGAAACGCGAAGACAUGCUGCU | 117-139 | 151 |
| AD-207630.1 | A-410796.1 | AAAGCACACUACUUUGAGCUU | 1446-1466 | 58 | A-410797.1 | AAGCUCAAAGUAGUGUGCUUUUU | 1444-1466 | 152 |
| AD-204103.1 | A-403760.1 | CAGUGAAGCAGUUCGUGCUAU | 967-987 | 59 | A-403761.1 | AUAGCACGAACUGCUUCACUGGC | 965-987 | 153 |
| AD-207219.1 | A-409976.1 | AUCAGUAUGCACUCAUACUCA | 984-1004 | 60 | A-409977.1 | UGAGUAUGAGUGCAUACUGAUGU | 982-1004 | 154 |
| AD-207627.1 | A-410790.1 | UAAAAAGCACACUACUUUGAA | 1443-1463 | 61 | A-410791.1 | UUCAAAGUAGUGUGCUUUUUAUU | 1441-1463 | 155 |
| AD-203796.1 | A-403146.1 | AUCGAAUGUGGAGAAAGAACA | 660-680 | 62 | A-403147.1 | UGUUCUUUCUCCACAUUCGAUUA | 658-680 | 156 |
| AD-203312.1 | A-402178.1 | AGCAGCAUGUCUUCGCGUUUA | 117-137 | 63 | A-402179.1 | UAAACGCGAAGACAUGCUGCUCA | 115-137 | 157 |
| AD-207207.1 | A-409952.1 | AUUAAAGCUUACAUCAGUAUA | 972-992 | 64 | A-409953.1 | UAUACUGAUGUAAGCUUUAAUGU | 970-992 | 158 |
| AD-203800.1 | A-403154.1 | AAUGUGGAGAAAGAACCGUUA | 664-684 | 65 | A-403155.1 | UAACGGUUCUUUCUCCACAUUCG | 662-684 | 159 |
| AD-207373.1 | A-410282.1 | AAGUUUAUAUCUAGCUCCUGA | 1145-1165 | 66 | A-410283.1 | UCAGGAGCUAGAUAUAAACUUUC | 1143-1165 | 160 |
| AD-207556.1 | A-410648.1 | UUAUUGAUUUCAGCAACACUU | 1369-1389 | 67 | A-410649.1 | AAGUGUUGCUGAAAUCAAUAAAA | 1367-1389 | 161 |
| AD-204302.1 | A-404158.1 | CUAAAAUAGCUUGGCAUGUCA | 1194-1214 | 68 | A-404159.1 | UGACAUGCCAAGCUAUUUUAGAG | 1192-1214 | 162 |
| AD-203921.1 | A-403396.1 | ACCUACUGUGGACUUUAUCCU | 785-805 | 69 | A-403397.1 | AGGAUAAAGUCCACAGUAGGUUU | 783-805 | 163 |
| AD-203316.1 | A-402186.1 | GCAUGUCUUCGCGUUUCAGAA | 121-141 | 70 | A-402187.1 | UUCUGAAACGCGAAGACAUGCUG | 119-141 | 164 |
| AD-207217.1 | A-409972.1 | ACAUCAGUAUGCACUCAUACU | 982-1002 | 71 | A-409973.1 | AGUAUGAGUGCAUACUGAUGUAA | 980-1002 | 165 |
| AD-204104.1 | A-403762.1 | AGUGAAGCAGUUCGUGCUAUU | 968-988 | 72 | A-403763.1 | AAUAGCACGAACUGCUUCACUGG | 966-988 | 166 |
| AD-203475.1 | A-402504.1 | CCAUUUAAAUGUGAGCGGAAU | 313-333 | 73 | A-402505.1 | AUUCCGCUCACAUUUAAAUGGGC | 311-333 | 167 |

TABLE 2-continued

Unmodified Sense and Antisense Strand Sequences of CPB2 dsRNA Agents

| Duplex Name | Sense Oligo Name | Sense Sequence 5' to 3' | Range | SEQ ID NO: | Antisense Oligo Name | Antisense Sequence 5' to 3' | Range | SEQ ID NO: |
|---|---|---|---|---|---|---|---|---|
| AD-207213.1 | A-409964.1 | GCUUACAUCAG UAUGCACUCA | 978-998 | 74 | A-409965.1 | UGAGUGCAUACUGAUGUAAGCUU | 976-998 | 168 |
| AD-204208.1 | A-403970.1 | UUUACAAUUGA ACUUCGAGAU | 1100-1120 | 75 | A-403971.1 | AUCUCGAAGUUCAAUUGUAAACG | 1098-1120 | 169 |
| AD-204186.1 | A-403926.1 | AUGAUUUGGGC AUCAAAUAUU | 1077-1097 | 76 | A-403927.1 | AAUAUUUGAUGCCCAAAUCAUAG | 1075-1097 | 170 |
| AD-203577.1 | A-402708.1 | UCACUCACUAA AUGAAAUCUA | 436-456 | 77 | A-402709.1 | UAGAUUUCAUUUAGUGAGUGAUA | 434-456 | 171 |
| AD-204093.1 | A-403740.1 | CUCUAGUAGCC AGUGAAGCAA | 957-977 | 78 | A-403741.1 | UUGCUUCACUGGCUACUAGAGAC | 955-977 | 172 |
| AD-203363.1 | A-402280.1 | GAACCUCUAGG CAAGUUCAAA | 168-188 | 79 | A-402281.1 | UUUGAACUUGCCUAGAGGUUCUA | 166-188 | 173 |
| AD-204184.1 | A-403922.1 | CUAUGAUUUGG GCAUCAAAUA | 1075-1095 | 80 | A-403923.1 | UAUUUGAUGCCCAAAUCAUAGAU | 1073-1095 | 174 |
| AD-204004.1 | A-403562.1 | AGCAUACAUCA GCAUGCAUUA | 868-888 | 81 | A-403563.1 | UAAUGCAUGCUGAUGUAUGCUUU | 866-888 | 175 |
| AD-203568.1 | A-402690.1 | UGAACAGUAUC ACUCACUAAA | 427-447 | 82 | A-402691.1 | UUUAGUGAGUGAUACUGUUCAUA | 425-447 | 176 |
| AD-203552.1 | A-402658.1 | CCUCCGCAUCG UACUAUGAAA | 411-431 | 83 | A-402659.1 | UUUCAUAGUACGAUGCGGAGGCU | 409-431 | 177 |
| AD-203555.1 | A-402664.1 | CCGCAUCGUAC UAUGAACAGU | 414-434 | 84 | A-402665.1 | ACUGUUCAUAGUACGAUGCGGAG | 412-434 | 178 |
| AD-204160.1 | A-403874.1 | AGAAACCUUAU ACCUAGCUCA | 1033-1053 | 85 | A-403875.1 | UGAGCUAGGUAUAAGGUUUCUGA | 1031-1053 | 179 |
| AD-203362.1 | A-402278.1 | AGAACCUCUAG GCAAGUUCAA | 167-187 | 86 | A-402279.1 | UUGAACUUGCCUAGAGGUUCUAG | 165-187 | 180 |
| AD-204011.1 | A-403576.1 | AUCAGCAUGCA UUCAUACUCA | 875-895 | 87 | A-403577.1 | UGAGUAUGAAUGCAUGCUGAUGU | 873-895 | 181 |
| AD-203477.1 | A-402508.1 | AUUUAAAUGUG AGCGGAAUUA | 315-335 | 88 | A-402509.1 | UAAUUCCGCUCACAUUUAAAUGG | 313-335 | 182 |
| AD-203640.1 | A-402834.1 | ACAAAAAUCCA CAUUGGAUCA | 500-520 | 89 | A-402835.1 | UGAUCCAAUGUGGAUUUUUGUAA | 498-520 | 183 |
| AD-203474.1 | A-402502.1 | CCCAUUUAAAU GUGAGCGGAA | 312-332 | 90 | A-402503.1 | UUCCGCUCACAUUUAAAUGGGCU | 310-332 | 184 |
| AD-204297.1 | A-404148.1 | UGUCUCUAAAA UAGCUUGGCA | 1189-1209 | 91 | A-404149.1 | UGCCAAGCUAUUUUAGAGACAGC | 1187-1209 | 185 |
| AD-206697.1 | A-408938.1 | UGAAAUCUAUU CCUGGAUAGA | 446-466 | 92 | A-408939.1 | UCUAUCCAGGAAUAGAUUUCAUU | 444-466 | 186 |
| AD-203488.1 | A-402530.1 | AGCGGAAUUCC AUGCAGUGUA | 326-346 | 93 | A-402531.1 | UACACUGCAUGGAAUUCCGCUCA | 324-346 | 187 |
| AD-204161.1 | A-403876.1 | GAAACCUUAUA CCUAGCUCCU | 1034-1054 | 94 | A-403877.1 | AGGAGCUAGGUAUAAGGUUUCUG | 1032-1054 | 188 |
| AD-203812.1 | A-403178.1 | GAACCGUUCUU UCUAUGCGAA | 676-696 | 95 | A-403179.1 | UUCGCAUAGAAAGAACGGUUCUU | 674-696 | 189 |
| AD-203811.1 | A-403176.1 | AGAACCGUUCU UUCUAUGCGA | 675-695 | 96 | A-403177.1 | UCGCAUAGAAAGAACGGUUCUUU | 673-695 | 190 |
| AD-203311.1 | A-402176.1 | GAGCAGCAUGU CUUCGCGUUU | 116-136 | 97 | A-402177.1 | AAACGCGAAGACAUGCUGCUCAC | 114-136 | 191 |
| AD-203554.1 | A-402662.1 | UCCGCAUCGUA CUAUGAACAA | 413-433 | 98 | A-402663.1 | UUGUUCAUAGUACGAUGCGGAGG | 411-433 | 192 |

TABLE 2-continued

Unmodified Sense and Antisense Strand Sequences of CPB2 dsRNA Agents

| Duplex Name | Sense Oligo Name | Sense Sequence 5' to 3' | Range | SEQ ID NO: | Antisense Oligo Name | Antisense Sequence 5' to 3' | Range | SEQ ID NO: |
|---|---|---|---|---|---|---|---|---|
| AD-204304.1 | A-404162.1 | AAAAUAGCUUGGCAUGUCAUU | 1196-1216 | 99 | A-404163.1 | AAUGACAUGCCAAGCUAUUUUAG | 1194-1216 | 193 |
| AD-204009.1 | A-403572.1 | ACAUCAGCAUGCAUUCAUACU | 873-893 | 100 | A-403573.1 | AGUAUGAAUGCAUGCUGAUGUAU | 871-893 | 194 |
| AD-204159.1 | A-403872.1 | CAGAAACCUUAUACCUAGCUA | 1032-1052 | 101 | A-403873.1 | UAGCUAGGUAUAAGGUUUCUGAG | 1030-1052 | 195 |
| AD-203556.1 | A-402666.1 | CGCAUCGUACUAUGAACAGUA | 415-435 | 102 | A-402667.1 | UACUGUUCAUAGUACGAUGCGGA | 413-435 | 196 |
| AD-204035.1 | A-403624.1 | CAUAUAGUGUUUCCAUAUUCA | 899-919 | 103 | A-403625.1 | UGAAUAUGGAAACACUAUAUGCU | 897-919 | 197 |
| AD-204539.1 | A-404632.1 | AGCCAUCUCAAGCAAGUUUAA | 1513-1533 | 104 | A-404633.1 | UUAAACUUGCUUGAGAUGGCUAG | 1511-1533 | 198 |
| AD-204005.1 | A-403564.1 | GCAUACAUCAGCAUGCAUUCA | 869-889 | 105 | A-403565.1 | UGAAUGCAUGCUGAUGUAUGCUU | 867-889 | 199 |
| AD-204189.1 | A-403932.1 | AUUUGGGCAUCAAAUAUUCGU | 1080-1100 | 106 | A-403933.1 | ACGAAUAUUUGAUGCCCAAAUCA | 1078-1100 | 200 |
| AD-204033.1 | A-403620.1 | AGCAUAUAGUGUUUCCAUAUU | 897-917 | 107 | A-403621.1 | AAUAUGGAAACACUAUAUGCUGG | 895-917 | 201 |
| AD-204426.1 | A-404406.1 | GAACCUAAUAAGUGCUACUUU | 1364-1384 | 108 | A-404407.1 | AAAGUAGCACUUAUUAGGUUCUC | 1362-1384 | 202 |
| AD-203839.1 | A-403232.1 | UUGCAUCGGAACAGACCUGAA | 703-723 | 109 | A-403233.1 | UUCAGGUCUGUUCCGAUGCAAUG | 701-723 | 203 |
| AD-204158.1 | A-403870.1 | UCAGAAACCUUAUACCUAGCU | 1031-1051 | 110 | A-403871.1 | AGCUAGGUAUAAGGUUUCUGAGC | 1029-1051 | 204 |
| AD-204032.1 | A-403618.1 | CAGCAUAUAGUGUUUCCAUAU | 896-916 | 111 | A-403619.1 | AUAUGGAAACACUAUAUGCUGGG | 894-916 | 205 |
| AD-203837.1 | A-403228.1 | CAUUGCAUCGGAACAGACCUA | 701-721 | 112 | A-403229.1 | UAGGUCUGUUCCGAUGCAAUGAU | 699-721 | 206 |
| AD-204003.1 | A-403560.1 | AAGCAUACAUCAGCAUGCAUU | 867-887 | 113 | A-403561.1 | AAUGCAUGCUGAUGUAUGCUUUA | 865-887 | 207 |
| AD-204425.1 | A-404404.1 | AGAACCUAAUAAGUGCUACUU | 1363-1383 | 114 | A-404405.1 | AAGUAGCACUUAUUAGGUUCUCU | 1361-1383 | 208 |
| AD-203302.1 | A-402158.1 | CUCUUCUGUGAGCAGCAUGUA | 107-127 | 115 | A-402159.1 | UACAUGCUGCUCACAGAAGAGAA | 105-127 | 209 |
| AD-204538.1 | A-404630.1 | UAGCCAUCUCAAGCAAGUUUA | 1481-1501 | 116 | A-404631.1 | UAAACUUGCUUGAGAUGGCUAGU | 1479-1501 | 210 |
| AD-203813.1 | A-403180.1 | AACCGUUCUUUCUAUGCGAAA | 677-697 | 117 | A-403181.1 | UUUCGCAUAGAAAGAACGGUUCU | 675-697 | 211 |
| AD-204024.1 | A-403602.1 | CAUACUCCCAGCAUAUAGUGU | 888-908 | 118 | A-403603.1 | ACACUAUAUGCUGGGAGUAUGAA | 886-908 | 212 |
| AD-203281.1 | A-402116.1 | GCAGUCCUUGUACCCAUUGUU | 86-106 | 119 | A-402117.1 | AACAAUGGGUACAAGGACUGCAA | 84-106 | 213 |
| AD-203310.1 | A-402174.1 | UGAGCAGCAUGUCUUCGCGUU | 115-135 | 120 | A-402175.1 | AACGCGAAGACAUGCUGCUCACA | 113-135 | 214 |
| AD-204540.1 | A-404634.1 | GCCAUCUCAAGCAAGUUUAAU | 1514-1534 | 121 | A-404635.1 | AUUAAACUUGCUUGAGAUGGCUA | 1512-1534 | 215 |
| AD-203401.1 | A-402356.1 | ACAACAUAUGAGAUUGUUCUA | 206-226 | 122 | A-402357.1 | UAGAACAAUCUCAUAUGUUGUAG | 204-226 | 216 |

TABLE 2-continued

Unmodified Sense and Antisense Strand Sequences of CPB2 dsRNA Agents

| Duplex Name | Sense Oligo Name | Sense Sequence 5' to 3' | Range | SEQ ID NO: | Antisense Oligo Name | Antisense Sequence 5' to 3' | Range | SEQ ID NO: |
|---|---|---|---|---|---|---|---|---|
| AD-204319.1 | A-404192.1 | GUCAUUAGGAA UGUUUAAUGA | 1211-1231 | 123 | A-404193.1 | UCAUUAAACAUUCCUAAUGACAU | 1209-1231 | 217 |
| AD-203359.1 | A-402272.1 | CCUAGAACCUC UAGGCAAGUU | 164-184 | 124 | A-402273.1 | AACUUGCCUAGAGGUUCUAGGAA | 162-184 | 218 |
| AD-203345.1 | A-402244.1 | UUCUAGCUGCU CUUCCUAGAA | 150-170 | 125 | A-402245.1 | UUCUAGGAAGAGCAGCUAGAACU | 148-170 | 219 |
| AD-204212.1 | A-403978.1 | CAAUUGAACUU CGAGAUACGA | 1104-1124 | 126 | A-403979.1 | UCGUAUCUCGAAGUUCAAUUGUA | 1102-1124 | 220 |
| AD-204013.1 | A-403580.1 | CAGCAUGCAUU CAUACUCCCA | 877-897 | 127 | A-403581.1 | UGGGAGUAUGAAUGCAUGCUGAU | 875-897 | 221 |
| AD-203818.1 | A-403190.1 | UUCUUUCUAUG CGAACAAUCA | 682-702 | 128 | A-403191.1 | UGAUUGUUCGCAUAGAAAGAACG | 680-702 | 222 |

TABLE 3

Modified Sense and Antisense Strand Sequences of CPB2 dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-206997.1 | csascgugGfaAfAf AfagaaucgaauL96 | 223 | asUfsucgAfuUfCfuuuuUfcCfacgugsusa | 317 | UACACGUGGAAAAAGAAUCGAAU | 411 |
| AD-204191.2 | ususgggcAfuCfAf AfauauucguuuL96 | 224 | asAfsacgAfaUfAfuuugAfuGfcccaasasu | 318 | AUUUGGGCAUCAAAUAUUCGUUU | 412 |
| AD-204195.1 | gscsaucaAfaUfAf UfucguuuacaaL96 | 225 | usUfsguaAfaCfGfaauaUfuUfgaugcscsc | 319 | GGGCAUCAAAUAUUCGUUUACAA | 413 |
| AD-204191.1 | ususgggcAfuCfAf AfauauucguuuL96 | 226 | asAfsacgAfaUfAfuuugAfuGfcccaasasu | 320 | AUUUGGGCAUCAAAUAUUCGUUU | 414 |
| AD-204194.1 | gsgscaucAfaAfUf AfuucguuuacaL96 | 227 | usGfsuaaAfcGfAfauauUfuGfaugccscsa | 321 | UGGGCAUCAAAUAUUCGUUUACA | 415 |
| AD-204193.2 | gsgsgcauCfaAfAf UfauucguuuaaL96 | 228 | usUfsaaaCfgAfAfuauuUfgAfugcccsasa | 322 | UUGGGCAUCAAAUAUUCGUUUAC | 416 |
| AD-204193.1 | gsgsgcauCfaAfAf UfauucguuuaaL96 | 229 | usUfsaaaCfgAfAfuauuUfgAfugcccsasa | 323 | UUGGGCAUCAAAUAUUCGUUUAC | 417 |
| AD-206996.1 | ascsacguGfgAfAf AfaagaaucgaaL96 | 230 | usUfscgaUfuCfUfuuuuCfcAfcgugusasg | 324 | CUACACGUGGAAAAAGAAUCGAA | 418 |
| AD-204192.1 | usgsggcaUfcAfAf AfuauucguuuaL96 | 231 | usAfsaacGfaAfUfauuuGfaUfgcccasasa | 325 | UUUGGGCAUCAAAUAUUCGUUUA | 419 |
| AD-203386.1 | csusacagAfaUfCf UfuacuacaacaL96 | 232 | usGfsuugUfaGfUfaagaUfuCfuguagsasa | 326 | UUCUACAGAAUCUUACUACAACA | 420 |
| AD-206944.1 | asgsgcacGfuGfGf AfuuucuacauaL96 | 233 | usAfsuguAfgAfAfauccAfcGfugccuscsa | 327 | UGAGGCACGUGGAUUUCUACAUC | 421 |
| AD-207600.1 | usgsaaucAfgUfUf UfccuugguuuuL96 | 234 | asAfsaacCfaAfGfgaaaCfuGfauucasasc | 328 | GUUGAAUCAGUUUCCUUGGUUUU | 422 |
| AD-206998.1 | ascsguggAfaAfAf AfgaaucgaauaL96 | 235 | usAfsuucGfaUfUfcuuuUfuCfcacgusgsu | 329 | ACACGUGGAAAAAGAAUCGAAUG | 423 |
| AD-203564.1 | ascsuaugAfaCfAf GfuaucacucaaL96 | 236 | usUfsgagUfgAfUfacugUfuCfauagusasc | 330 | GUACUAUGAACAGUAUCACUCAC | 424 |
| AD-204194.2 | gsgscaucAfaAfUf AfuucguuuacaL96 | 237 | usGfsuaaAfcGfAfauauUfuGfaugccscsa | 331 | UGGGCAUCAAAUAUUCGUUUACA | 425 |

TABLE 3-continued

Modified Sense and Antisense Strand Sequences of CPB2 dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-204190.1 | ususugggCfaUfCfAfaauauucguuL96 | 238 | asAfscgaAfuAfUfuugaUfgCfccaaasusc | 332 | GAUUUGGGCAUCAAAUAUUCGUU | 426 |
| AD-204014.1 | asgscaugCfaUfUfCfauacucccaaL96 | 239 | usUfsgggAfgUfAfugaaUfgCfaugcusgsa | 333 | UCAGCAUGCAUUCAUACUCCCAG | 427 |
| AD-206596.1 | asgscagaAfuUfCfCfauuuaacguuL96 | 240 | asAfscguUfaAfAfuggaAfuUfcugcuscsa | 334 | UGAGCAGAAUUCCAUUUAACGUU | 428 |
| AD-207367.1 | csasgaaaGfuUfUfAfuaucuagcuaL96 | 241 | usAfsgcuAfgAfUfauaaAfcUfuucugsasg | 335 | CUCAGAAAGUUUAUAUCUAGCUC | 429 |
| AD-207362.1 | usgsgcucAfgAfAfAfguuuauaucuL96 | 242 | asGfsauaUfaAfAfcuuuCfuGfagccascsu | 336 | AGUGGCUCAGAAAGUUUAUAUCU | 430 |
| AD-206384.1 | usgsguagCfcAfUfCfauccucuauaL96 | 243 | usAfsuagAfgGfAfugauGfgCfuaccasgsg | 337 | CCUGGUAGCCAUCAUCCUCUAUG | 431 |
| AD-207212.1 | asgscuuaCfaUfCfAfguaugcacuaL96 | 244 | usAfsgugCfaUfAfcugaUfgUfaagcususu | 338 | AAAGCUUACAUCAGUAUGCACUC | 432 |
| AD-203314.1 | csasgcauGfuCfUfUfcgcguuucaaL96 | 245 | usUfsgaaAfcGfCfgaagAfcAfugcugscsu | 339 | AGCAGCAUGUCUUCGCGUUUCAG | 433 |
| AD-207630.1 | asasagcaCfaCfUfAfcuuugagcuuL96 | 246 | asAfsgcuCfaAfAfguagUfgUfgcuuususu | 340 | AAAAAGCACACUACUUUGAGCUU | 434 |
| AD-204103.1 | csasgugaAfgCfAfGfuucgugcuauL96 | 247 | asUfsagcAfcGfAfacugCfuUfcacugsgsc | 341 | GCCAGUGAAGCAGUUCGUGCUAU | 435 |
| AD-207219.1 | asuscaguAfuGfCfAfcucauacucaL96 | 248 | usGfsaguAfuGfAfgugcAfuAfcugausgsu | 342 | ACAUCAGUAUGCACUCAUACUCC | 436 |
| AD-207627.1 | usasaaaaGfcAfCfAfcuacuuugaaL96 | 249 | usUfscaaAfgUfAfguguGfcUfuuuuasusu | 343 | AAUAAAAAGCACACUACUUUGAG | 437 |
| AD-203796.1 | asuscgaaUfgUfGfGfagaaagaacaL96 | 250 | usGfsuucUfuUfCfuccaCfaUfucgaususa | 344 | UAAUCGAAUGUGGAGAAAGAACC | 438 |
| AD-203312.1 | asgscagcAfuGfUfCfuucgcguuuaL96 | 251 | usAfsaacGfcGfAfagacAfuGfcugcuscsa | 345 | UGAGCAGCAUGUCUUCGCGUUUC | 439 |
| AD-207207.1 | asusuaaaGfcUfUfAfcaucaguauaL96 | 252 | usAfsuacUfgAfUfguaaGfcUfuuaausgsu | 346 | ACAUUAAAGCUUACAUCAGUAUG | 440 |
| AD-203800.1 | asasugugGfaGfAfAfagaaccguuaL96 | 253 | usAfsacgGfuUfCfuuucUfcCfacauuscsg | 347 | CGAAUGUGGAGAAAGAACCGUUC | 441 |
| AD-207373.1 | asasguuuAfuAfUfCfuagcuccugaL96 | 254 | usCfsaggAfgCfUfagauAfuAfaacuususc | 348 | GAAAGUUUAUAUCUAGCUCCUGG | 442 |
| AD-207556.1 | ususauugAfuUfUfCfagcaacacuuL96 | 255 | asAfsgugUfuGfCfugaaAfuCfaauaasasa | 349 | UUUUAUUGAUUUCAGCAACACUU | 443 |
| AD-204302.1 | csusaaaaUfaGfCfUfuggcaugucaL96 | 256 | usGfsacaUfgCfCfaagcUfaUfuuuagsasg | 350 | CUCUAAAAUAGCUUGGCAUGUCA | 444 |
| AD-203921.1 | ascscuacUfgUfGfGfacuuuauccuL96 | 257 | asGfsgauAfaAfGfuccaCfaGfuaggususu | 351 | AAACCUACUGUGGACUUUAUCCU | 445 |
| AD-203316.1 | gscsauguCfuUfCfGfcguuucagaaL96 | 258 | usUfscugAfaAfCfgcgaAfgAfcaugcsusg | 352 | CAGCAUGUCUUCGCGUUUCAGAG | 446 |
| AD-207217.1 | ascsaucaGfuAfUfGfcacucauacuL96 | 259 | asGfsuauGfaGfUfgcauAfcUfgaugusasa | 353 | UUACAUCAGUAUGCACUCAUACU | 447 |
| AD-204104.1 | asgsugaaGfcAfGfUfucgugcuauuL96 | 260 | asAfsuagCfaCfGfaacuGfcUfucacusgsg | 354 | CCAGUGAAGCAGUUCGUGCUAUU | 448 |
| AD-203475.1 | cscsauuuAfaAfUfGfugagcggaauL96 | 261 | asUfsuccGfcUfCfacauUfuAfaauggsgsc | 355 | GCCCAUUUAAAUGUGAGCGGAAU | 449 |
| AD-207213.1 | gscsuuacAfuCfAfGfuaugcacucaL96 | 262 | usGfsaguGfcAfUfacugAfuGfuaagcsusu | 356 | AAGCUUACAUCAGUAUGCACUCA | 450 |

TABLE 3-continued

Modified Sense and Antisense Strand Sequences of CPB2 dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-204208.1 | ususuacaAfuUfGfAfacuucgagauL96 | 263 | asUfscucGfaAfGfuucaAfuUfguaaascsg | 357 | CGUUUACAAUUGAACUUCGAGAU | 451 |
| AD-204186.1 | asusgauuUfgGfGfCfaucaaauauuL96 | 264 | asAfsuauUfuGfAfugccCfaAfaucausasg | 358 | CUAUGAUUUGGGCAUCAAAUAUU | 452 |
| AD-203577.1 | uscsacucAfcUfAfAfaugaaaucuaL96 | 265 | usAfsgauUfuCfAfuuuaGfuGfagugasusa | 359 | UAUCACUCACUAAAUGAAAUCUA | 453 |
| AD-204093.1 | csuscuagUfaGfCfCfagugaagcaaL96 | 266 | usUfsgcuUfcAfCfuggcUfaCfuagagsasc | 360 | GUCUCUAGUAGCCAGUGAAGCAG | 454 |
| AD-203363.1 | gsasaccuCfuAfGfGfcaaguucaaaL96 | 267 | usUfsugaAfcUfUfgccuAfgAfgguucsusa | 361 | UAGAACCUCUAGGCAAGUUCAAG | 455 |
| AD-204184.1 | csusaugaUfuUfGfGfgcaucaaauaL96 | 268 | usAfsuuuGfaUfGfcccaAfaUfcauagsasu | 362 | AUCUAUGAUUUGGGCAUCAAAUA | 456 |
| AD-204004.1 | asgscauaCfaUfCfAfgcaugcauuaL96 | 269 | usAfsaugCfaUfGfcugaUfgUfaugcususu | 363 | AAAGCAUACAUCAGCAUGCAUUC | 457 |
| AD-203568.1 | usgsaacaGfuAfUfCfacucacuaaaL96 | 270 | usUfsuagUfgAfGfugauAfcUfguucasusa | 364 | UAUGAACAGUAUCACUCACUAAA | 458 |
| AD-203552.1 | cscsuccgCfaUfCfGfuacuaugaaaL96 | 271 | usUfsucaUfaGfUfacgaUfgCfggaggscsu | 365 | AGCCUCCGCAUCGUACUAUGAAC | 459 |
| AD-203555.1 | cscsgcauCfgUfAfCfuaugaacaguL96 | 272 | asCfsuguUfcAfUfaguaCfgAfugcggsasg | 366 | CUCCGCAUCGUACUAUGAACAGU | 460 |
| AD-204160.1 | asgsaaacCfuUfAfUfaccuagcucaL96 | 273 | usGfsagcUfaGfGfuauaAfgGfuuucusgsa | 367 | UCAGAAACCUUAUACCUAGCUCC | 461 |
| AD-203362.1 | asgsaaccUfcUfAfGfgcaaguucaaL96 | 274 | usUfsgaaCfuUfGfccuaGfaGfguucusasg | 368 | CUAGAACCUCUAGGCAAGUUCAA | 462 |
| AD-204011.1 | asuscagcAfuGfCfAfuucauacucaL96 | 275 | usGfsaguAfuGfAfaugcAfuGfcugausgsu | 369 | ACAUCAGCAUGCAUUCAUACUCC | 463 |
| AD-203477.1 | asusuuaaAfuGfUfGfagcggaauuaL96 | 276 | usAfsauuCfcGfCfucacAfuUfuaaausgsg | 370 | CCAUUUAAAUGUGAGCGGAAUUC | 464 |
| AD-203640.1 | ascsaaaaAfuCfCfAfcauuggaucaL96 | 277 | usGfsaucCfaAfUfguggAfuUfuuugusasa | 371 | UUACAAAAAUCCACAUUGGAUCC | 465 |
| AD-203474.1 | cscscauuUfaAfAfUfgugagcggaaL96 | 278 | usUfsccgCfuCfAfcauuUfaAfaugggscsu | 372 | AGCCCAUUUAAAUGUGAGCGGAA | 466 |
| AD-204297.1 | usgsucucUfaAfAfAfuagcuuggcaL96 | 279 | usGfsccaAfgCfUfauuuUfaGfagacasgsc | 373 | GCUGUCUCUAAAAUAGCUUGGCA | 467 |
| AD-206697.1 | usgsaaauCfuAfUfUfccuggauagaL96 | 280 | usCfsuauCfcAfGfgaauAfgAfuuucasusu | 374 | AAUGAAAUCUAUUCCUGGAUAGA | 468 |
| AD-203488.1 | asgscggaAfuUfCfCfaugcaguguaL96 | 281 | usAfscacUfgCfAfuggaAfuUfccgcuscsa | 375 | UGAGCGGAAUUCCAUGCAGUGUC | 469 |
| AD-204161.1 | gsasaaccUfuAfUfAfccuagcuccuL96 | 282 | asGfsgagCfuAfGfguauAfaGfguuucsusg | 376 | CAGAAACCUUAUACCUAGCUCCU | 470 |
| AD-203812.1 | gsasaccgUfuCfUfUfucuaugcgaaL96 | 283 | usUfscgcAfuAfGfaaagAfaCfgguucsusu | 377 | AAGAACCGUUCUUUCUAUGCGAA | 471 |
| AD-203811.1 | asgsaaccGfuUfCfUfuucuaugcgaL96 | 284 | usCfsgcaUfaGfAfaagaAfcGfguucususu | 378 | AAAGAACCGUUCUUUCUAUGCGA | 472 |
| AD-203311.1 | gsasgcagCfaUfGfUfcuucgcguuuL96 | 285 | asAfsacgCfgAfAfgacaUfgCfugcucsasc | 379 | GUGAGCAGCAUGUCUUCGCGUUU | 473 |
| AD-203554.1 | uscscgcaUfcGfUfAfcuaugaacaaL96 | 286 | usUfsguuCfaUfAfguacGfaUfgcggasgsg | 380 | CCUCCGCAUCGUACUAUGAACAG | 474 |

TABLE 3-continued

Modified Sense and Antisense Strand Sequences of CPB2 dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-204304.1 | asasaauaGfcUfUfGfgcaugucauuL96 | 287 | asAfsugaCfaUfGfccaaGfcUfauuuusasg | 381 | CUAAAAUAGCUUGGCAUGUCAUU | 475 |
| AD-204009.1 | ascsaucaGfcAfUfGfcauucauacuL96 | 288 | asGfsuauGfaAfUfgcauGfcUfgaugusasu | 382 | AUACAUCAGCAUGCAUUCAUACU | 476 |
| AD-204159.1 | csasgaaaCfcUfUfAfuaccuagcuaL96 | 289 | usAfsgcuAfgGfUfauaaGfgUfuucugsasg | 383 | CUCAGAAACCUUAUACCUAGCUC | 477 |
| AD-203556.1 | csgscaucGfuAfCfUfaugaacaguaL96 | 290 | usAfscugUfuCfAfuaguAfcGfaugcgsgsa | 384 | UCCGCAUCGUACUAUGAACAGUA | 478 |
| AD-204035.1 | csasuauaGfuGfUfUfuccauauucaL96 | 291 | usGfsaauAfuGfGfaaacAfcUfauaugscsu | 385 | AGCAUAUAGUGUUUCCAUAUUCC | 479 |
| AD-204539.1 | asgsccauCfuCfAfAfgcaaguuuaaL96 | 292 | usUfsaaaCfuUfGfcuugAfgAfuggcusasg | 386 | CUAGCCAUCUCAAGCAAGUUUAA | 480 |
| AD-204005.1 | gcsauacAfuCfAfGfcaugcauucaL96 | 293 | usGfsaauGfcAfUfgcugAfuGfuaugcsusu | 387 | AAGCAUACAUCAGCAUGCAUUCA | 481 |
| AD-204189.1 | asusuuggGfcAfUfCfaaauauucguL96 | 294 | asCfsgaaUfaUfUfugauGfcCfcaaauscsa | 388 | UGAUUUGGGCAUCAAAUAUUCGU | 482 |
| AD-204033.1 | asgscauaUfaGfUfGfuuuccauauuL96 | 295 | asAfsuauGfgAfAfacacUfaUfaugcusgsg | 389 | CCAGCAUAUAGUGUUUCCAUAUU | 483 |
| AD-204426.1 | gsasaccuAfaUfAfAfgugcuacuuuL96 | 296 | asAfsaguAfgCfAfcuuaUfuAfgguucsusc | 390 | GAGAACCUAAUAAGUGCUACUUU | 484 |
| AD-203839.1 | ususgcauCfgGfAfAfcagaccugaaL96 | 297 | usUfscagGfuCfUfguucCfgAfugcaasusg | 391 | CAUUGCAUCGGAACAGACCUGAA | 485 |
| AD-204158.1 | uscsagaaAfcCfUfUfauaccuagcuL96 | 298 | asGfscuaGfgUfAfuaagGfuUfucugasgsc | 392 | GCUCAGAAACCUUAUACCUAGCU | 486 |
| AD-204032.1 | csasgcauAfuAfGfUfguuuccauauL96 | 299 | asUfsaugGfaAfAfcacuAfuAfugcugsgsg | 393 | CCCAGCAUAUAGUGUUUCCAUAU | 487 |
| AD-203837.1 | csasuugcAfuCfGfGfaacagaccuaL96 | 300 | usAfsgguCfuGfUfuccgAfuGfcaaugsasu | 394 | AUCAUUGCAUCGGAACAGACCUG | 488 |
| AD-204003.1 | asasgcauAfcAfUfCfagcaugcauuL96 | 301 | asAfsugcAfuGfCfugauGfuAfugcuususa | 395 | UAAAGCAUACAUCAGCAUGCAUU | 489 |
| AD-204425.1 | asgsaaccUfaAfUfAfagugcuacuuL96 | 302 | asAfsguaGfcAfCfuuauUfaGfguucuscsu | 396 | AGAGAACCUAAUAAGUGCUACUU | 490 |
| AD-203302.1 | csuscuucUfgUfGfAfgcagcauguaL96 | 303 | usAfscauGfcUfGfcucaCfaGfaagagsasa | 397 | UUCUCUUCUGUGAGCAGCAUGUC | 491 |
| AD-204538.1 | usasgccaUfcUfCfAfagcaaguuuaL96 | 304 | usAfsaacUfuGfCfuugaGfaUfggcuasgsu | 398 | ACUAGCCAUCUCAAGCAAGUUUC | 492 |
| AD-203813.1 | asasccguUfcUfUfUfcuaugcgaaaL96 | 305 | usUfsucgCfaUfAfgaaaGfaAfcgguuscsu | 399 | AGAACCGUUCUUUCUAUGCGAAC | 493 |
| AD-204024.1 | csasuacuCfcCfAfGfcauauaguguL96 | 306 | asCfsacuAfuAfUfgcugGfgAfguaugsasa | 400 | UUCAUACUCCCAGCAUAUAGUGU | 494 |
| AD-203281.1 | gscsagucCfuUfGfUfacccauuguuL96 | 307 | asAfscaaUfgGfGfuacaAfgGfacugcsasa | 401 | UUGCAGUCCUUGUACCCAUUGUU | 495 |
| AD-203310.1 | usgsagcaGfcAfUfGfucuucgcguuL96 | 308 | asAfscgcGfaAfGfacauGfcUfgcucascsa | 402 | UGUGAGCAGCAUGUCUUCGCGUU | 496 |
| AD-204540.1 | gscscaucUfcAfAfGfcaaguuuaauL96 | 309 | asUfsuaaAfcUfUfgcuuGfaGfauggcsusa | 403 | UAGCCAUCUCAAGCAAGUUUAAU | 497 |
| AD-203401.1 | ascsaacaUfaUfGfAfgauuguucuaL96 | 310 | usAfsgaaCfaAfUfcucaUfaUfguugusasg | 404 | CUACAACAUAUGAGAUUGUUCUC | 498 |
| AD-204319.1 | gsuscauuAfgGfAfAfuguuuaaugaL96 | 311 | usCfsauuAfaAfCfauucCfuAfaugacsasu | 405 | AUGUCAUUAGGAAUGUUUAAUGC | 499 |

TABLE 3-continued

Modified Sense and Antisense Strand Sequences of CPB2 dsRNA Agents

| Duplex Name | Modified Sense Sequence 5' to 3' | SEQ ID NO: | Modified Antisense Sequence 5' to 3' | SEQ ID NO: | mRNA target sequence 5' to 3' | SEQ ID NO: |
|---|---|---|---|---|---|---|
| AD-203359.1 | cscsuagaAfcCfUfCfuaggcaaguuL96 | 312 | asAfscuuGfcCfUfagagGfuUfcuaggsasa | 406 | UUCCUAGAACCUCUAGGCAAGUU | 500 |
| AD-203345.1 | ususcuagCfuGfCfUfcuuccuagaaL96 | 313 | usUfscuaGfgAfAfgagcAfgCfuagaascsu | 407 | AGUUCUAGCUGCUCUUCCUAGAA | 501 |
| AD-204212.1 | csasauugAfaCfUfUfcgagauacgaL96 | 314 | usCfsguaUfcUfCfgaagUfuCfaauugsusa | 408 | UACAAUUGAACUUCGAGAUACGG | 502 |
| AD-204013.1 | csasgcauGfcAfUfUfcauacucccaL96 | 315 | usGfsggaGfuAfUfgaauGfcAfugcugsasu | 409 | AUCAGCAUGCAUUCAUACUCCCA | 503 |
| AD-203818.1 | ususcuuuCfuAfUfGfcgaacaaucaL96 | 316 | usGfsauuGfuUfCfgcauAfgAfaagaascsg | 410 | CGUUCUUUCUAUGCGAACAAUCA | 504 |

TABLE 4

CPB2 Single 10 nM and 0.1 nM Dose Screen in Hep3B and PMH cells

| Duplex Name | Hep3B 10 nM | Std | Hep3B 0.1 nM | Std | PMH 10 nM | Std | PMH 0.1 nM | Std |
|---|---|---|---|---|---|---|---|---|
| AD-206997.1 | 47.83 | 15.05 | 67.03 | 4.85 | 5.14 | 0.83 | 65.22 | 2.73 |
| AD-204191.2 | 27.54 | 7.39 | 42.98 | 3.80 | 6.16 | 0.80 | 69.36 | 4.39 |
| AD-204195.1 | 28.94 | 4.85 | 57.26 | 7.19 | 6.39 | 1.76 | 77.40 | 22.22 |
| AD-204191.1 | 46.00 | 16.28 | 65.43 | 10.24 | 6.94 | 1.69 | 69.23 | 15.54 |
| AD-204194.1 | 34.92 | 6.78 | 66.02 | 17.88 | 7.15 | 1.13 | 75.51 | 2.61 |
| AD-204193.2 | 43.51 | 10.77 | 61.46 | 36.19 | 8.37 | 1.69 | 66.75 | 6.03 |
| AD-204193.1 | 32.42 | 10.01 | 85.96 | 10.02 | 8.74 | 0.58 | 69.19 | 12.56 |
| AD-206996.1 | 34.39 | 4.59 | 62.89 | 8.92 | 11.42 | 0.65 | 61.21 | 8.30 |
| AD-204192.1 | 28.32 | 4.38 | 88.91 | 25.80 | 11.61 | 3.88 | 76.92 | 12.24 |
| AD-203386.1 | 33.35 | 2.80 | 75.25 | 13.24 | 12.70 | 3.47 | 82.26 | 9.05 |
| AD-206944.1 | 133.45 | 39.63 | 108.79 | 20.53 | 13.14 | 0.86 | 77.44 | 15.45 |
| AD-207600.1 | 96.97 | 11.66 | 107.12 | 6.05 | 13.49 | 1.57 | 75.77 | 6.99 |
| AD-206998.1 | 42.37 | 8.37 | 94.65 | 12.02 | 13.58 | 0.84 | 72.87 | 5.64 |
| AD-203564.1 | 36.38 | 24.61 | 69.76 | 14.93 | 13.72 | 5.92 | 98.19 | 11.16 |
| AD-204194.2 | 45.52 | 19.80 | 69.58 | 19.39 | 14.01 | 1.84 | 79.58 | 7.82 |
| AD-204190.1 | 62.25 | 15.76 | 88.89 | 8.87 | 15.29 | 1.33 | 85.14 | 4.19 |
| AD-204014.1 | 24.42 | 16.38 | 63.98 | 9.94 | 18.14 | 3.83 | 113.75 | 8.13 |
| AD-206596.1 | 99.38 | 4.39 | 89.37 | 6.47 | 21.34 | 1.20 | 86.96 | 12.44 |
| AD-207367.1 | 102.38 | 14.82 | 100.64 | 17.20 | 21.79 | 5.42 | 92.71 | 14.87 |
| AD-207362.1 | 97.27 | 15.88 | 93.21 | 18.12 | 22.83 | 1.96 | 89.19 | 12.24 |
| AD-206384.1 | 126.37 | 17.54 | 131.25 | 26.78 | 26.25 | 3.04 | 81.11 | 9.88 |
| AD-207212.1 | 66.37 | 5.58 | 79.70 | 11.07 | 26.41 | 7.50 | 89.23 | 9.29 |
| AD-203314.1 | 37.69 | 6.19 | 117.08 | 47.57 | 28.92 | 3.39 | 69.79 | 13.33 |
| AD-207630.1 | 106.46 | 7.51 | 126.23 | 38.16 | 28.97 | 0.67 | 85.32 | 3.44 |
| AD-204103.1 | 23.83 | 1.54 | 66.33 | 15.12 | 29.42 | 6.77 | 99.19 | 6.81 |
| AD-207219.1 | 58.79 | 2.81 | 122.86 | 22.97 | 31.58 | 5.98 | 94.68 | 20.99 |
| AD-207627.1 | 112.18 | 32.21 | 129.86 | 37.60 | 32.26 | 5.82 | 91.60 | 9.27 |
| AD-203796.1 | 33.21 | 7.11 | 100.92 | 20.62 | 35.58 | 11.46 | 83.20 | 13.88 |
| AD-203312.1 | 35.65 | 9.41 | 74.46 | 8.97 | 36.02 | 6.49 | 87.61 | 16.29 |
| AD-207207.1 | 103.61 | 10.73 | 98.97 | 24.68 | 36.50 | 2.82 | 98.85 | 7.86 |
| AD-203800.1 | 18.56 | 3.22 | 83.19 | 5.16 | 36.82 | 5.66 | 102.11 | 11.84 |
| AD-207373.1 | 119.02 | 27.64 | 112.16 | 34.01 | 37.39 | 4.61 | 104.71 | 8.85 |
| AD-207556.1 | 95.48 | 9.56 | 88.35 | 10.91 | 38.07 | 6.44 | 85.35 | 9.42 |
| AD-204302.1 | 31.19 | 6.56 | 98.70 | 11.95 | 38.55 | 7.88 | 120.53 | 5.69 |
| AD-203921.1 | 43.21 | 3.25 | 153.13 | 21.69 | 39.68 | 26.18 | 71.11 | 13.52 |
| AD-203316.1 | 33.03 | 1.24 | 105.32 | 27.71 | 42.63 | 13.09 | 90.10 | 20.63 |
| AD-207217.1 | 84.06 | 7.60 | 81.69 | 10.37 | 45.49 | 7.81 | 93.46 | 9.14 |
| AD-204104.1 | 40.41 | 5.81 | 86.37 | 4.50 | 50.20 | 10.86 | 108.26 | 20.69 |
| AD-203475.1 | 40.18 | 6.23 | 90.99 | 8.11 | 51.06 | 2.49 | 100.76 | 5.81 |
| AD-207213.1 | 91.37 | 14.14 | 96.09 | 21.65 | 52.15 | 8.28 | 107.60 | 8.20 |
| AD-204208.1 | 35.03 | 6.51 | 86.43 | 10.70 | 52.78 | 13.82 | 104.85 | 23.62 |
| AD-204186.1 | 81.19 | 11.14 | 111.79 | 4.12 | 53.06 | 5.33 | 101.60 | 2.74 |
| AD-203577.1 | 41.63 | 4.31 | 89.25 | 9.55 | 54.99 | 5.46 | 96.40 | 3.17 |
| AD-204093.1 | 42.55 | 12.08 | 100.54 | 17.37 | 55.63 | 9.63 | 91.38 | 14.13 |
| AD-203363.1 | 47.18 | 19.39 | 115.27 | 44.78 | 59.38 | 15.22 | 127.44 | 16.52 |
| AD-204184.1 | 65.26 | 13.41 | 107.73 | 10.25 | 63.75 | 6.74 | 99.40 | 6.36 |
| AD-204004.1 | 41.92 | 5.26 | 89.75 | 5.26 | 63.98 | 3.53 | 93.88 | 6.24 |
| AD-203568.1 | 39.07 | 9.73 | 93.45 | 19.91 | 64.98 | 16.96 | 100.89 | 22.76 |

TABLE 4-continued

CPB2 Single 10 nM and 0.1 nM Dose Screen in Hep3B and PMH cells

| Duplex Name | Hep3B 10 nM | Std | Hep3B 0.1 nM | Std | PMH 10 nM | Std | PMH 0.1 nM | Std |
|---|---|---|---|---|---|---|---|---|
| AD-203552.1 | 36.76 | 8.78 | 83.20 | 5.67 | 66.95 | 7.51 | 95.63 | 4.88 |
| AD-203555.1 | 46.34 | 7.12 | 96.53 | 17.15 | 68.39 | 9.97 | 87.54 | 14.60 |
| AD-204160.1 | 47.93 | 16.72 | 97.26 | 22.93 | 69.98 | 23.10 | 97.95 | 14.51 |
| AD-203362.1 | 67.16 | 13.61 | 125.70 | 8.65 | 70.14 | 5.50 | 100.60 | 10.70 |
| AD-204011.1 | 41.22 | 4.52 | 79.18 | 6.46 | 72.31 | 8.61 | 103.86 | 14.72 |
| AD-203477.1 | 62.36 | 9.36 | 111.54 | 8.29 | 73.96 | 5.77 | 103.35 | 4.33 |
| AD-203640.1 | 49.53 | 17.06 | 126.25 | 24.03 | 76.17 | 16.29 | 99.07 | 27.47 |
| AD-203474.1 | 39.19 | 7.75 | 87.97 | 32.22 | 76.78 | 19.81 | 124.64 | 11.51 |
| AD-204297.1 | 46.16 | 9.70 | 106.40 | 16.25 | 76.88 | 14.43 | 94.13 | 8.79 |
| AD-206697.1 | 85.65 | 13.51 | 122.77 | 17.60 | 77.74 | 4.36 | 99.57 | 4.69 |
| AD-203488.1 | 46.50 | 15.62 | 114.92 | 8.65 | 78.49 | 21.18 | 98.23 | 12.76 |
| AD-204161.1 | 34.35 | 8.43 | 79.30 | 2.15 | 78.56 | 13.01 | 101.68 | 5.54 |
| AD-203812.1 | 48.64 | 6.77 | 99.89 | 8.20 | 79.27 | 3.04 | 87.96 | 12.74 |
| AD-203811.1 | 44.03 | 5.94 | 90.33 | 15.13 | 81.86 | 19.70 | 106.37 | 14.88 |
| AD-203311.1 | 34.58 | 6.19 | 123.26 | 30.71 | 82.66 | 22.01 | 130.20 | 9.21 |
| AD-203554.1 | 54.26 | 6.64 | 118.61 | 6.24 | 82.99 | 7.67 | 96.62 | 4.66 |
| AD-204304.1 | 62.31 | 7.31 | 107.77 | 32.87 | 84.23 | 11.30 | 98.78 | 11.79 |
| AD-204009.1 | 47.45 | 17.50 | 134.56 | 56.67 | 85.29 | 17.33 | 112.81 | 36.73 |
| AD-204159.1 | 54.48 | 5.88 | 87.05 | 14.20 | 85.57 | 7.03 | 109.53 | 10.34 |
| AD-203556.1 | 44.44 | 9.10 | 119.42 | 5.96 | 85.65 | 5.72 | 96.72 | 17.83 |
| AD-204035.1 | 31.48 | 5.09 | 72.73 | 9.22 | 88.43 | 7.19 | 88.76 | 14.18 |
| AD-204539.1 | 34.72 | 3.83 | 66.78 | 7.95 | 88.74 | 4.12 | 95.11 | 13.80 |
| AD-204005.1 | 61.07 | 25.49 | 116.51 | 15.49 | 89.45 | 27.59 | 131.49 | 20.23 |
| AD-204189.1 | 142.82 | 30.17 | 93.60 | 12.18 | 90.61 | 12.80 | 89.98 | 9.70 |
| AD-204033.1 | 71.58 | 17.68 | 113.09 | 17.43 | 90.97 | 16.75 | 93.47 | 13.18 |
| AD-204426.1 | 52.95 | 18.33 | 59.96 | 7.23 | 92.65 | 17.76 | 133.67 | 20.58 |
| AD-203839.1 | 37.65 | 6.47 | 125.05 | 10.69 | 93.03 | 16.04 | 105.77 | 13.01 |
| AD-204158.1 | 61.91 | 13.44 | 113.58 | 12.37 | 93.25 | 5.15 | 100.83 | 9.09 |
| AD-204032.1 | 57.42 | 5.60 | 96.88 | 13.94 | 94.62 | 23.09 | 106.26 | 13.26 |
| AD-203837.1 | 31.83 | 9.41 | 82.64 | 11.73 | 96.43 | 8.70 | 96.36 | 16.07 |
| AD-204003.1 | 49.15 | 9.06 | 94.53 | 5.21 | 96.46 | 4.83 | 96.21 | 6.96 |
| AD-204425.1 | 35.30 | 9.89 | 70.10 | 15.57 | 96.47 | 25.50 | 111.89 | 25.39 |
| AD-203302.1 | 87.48 | 3.31 | 146.21 | 33.75 | 100.73 | 12.00 | 122.62 | 10.15 |
| AD-204538.1 | 36.75 | 10.09 | 71.22 | 12.39 | 102.48 | 16.14 | 94.29 | 19.98 |
| AD-203813.1 | 52.90 | 8.96 | 111.67 | 17.39 | 102.85 | 5.38 | 96.23 | 16.45 |
| AD-204024.1 | 53.69 | 15.88 | 74.54 | 8.34 | 104.92 | 23.82 | 106.22 | 15.21 |
| AD-203281.1 | 76.18 | 15.94 | 99.04 | 6.70 | 107.17 | 11.78 | 101.84 | 7.87 |
| AD-203310.1 | 62.83 | 6.54 | 87.80 | 3.81 | 108.01 | 17.04 | 104.42 | 11.90 |
| AD-204540.1 | 61.84 | 3.69 | 99.93 | 5.79 | 108.16 | 12.32 | 105.21 | 19.39 |
| AD-203401.1 | 35.30 | 3.60 | 87.88 | 7.45 | 109.70 | 9.96 | 96.94 | 19.57 |
| AD-204319.1 | 43.06 | 8.83 | 124.90 | 5.09 | 113.65 | 35.56 | 121.97 | 9.14 |
| AD-203359.1 | 75.65 | 15.57 | 101.42 | 5.41 | 118.13 | 11.27 | 136.09 | 11.76 |
| AD-203345.1 | 107.60 | 24.04 | 211.69 | 37.81 | 125.92 | 14.03 | 141.04 | 17.53 |
| AD-204212.1 | 49.51 | 18.98 | 110.91 | 15.92 | 126.66 | 17.82 | 107.47 | 29.04 |
| AD-204013.1 | 68.48 | 4.52 | 134.05 | 27.24 | 126.94 | 56.74 | 131.50 | 7.80 |
| AD-203818.1 | 25.28 | 6.48 | 95.04 | 24.03 | 138.14 | 33.49 | 108.16 | 14.59 |

Example 3. In Vivo Screening of dsRNA Duplexes in Mice

Duplexes of interest, identified from the above in vitro studies, were evaluated in mice. Female wild-type (C57BL/6) mice (n=3 per group) were subcutaneously administered a single 2 mg/kg dose of the GalNAc conjugated siRNAs shown in FIG. 1, on day 0. Ten days post dosing, animal liver samples were collected and snap-frozen in liquid nitrogen. Tissue mRNA was extracted and analyzed by the RT-QPCR method.

Figure 2:
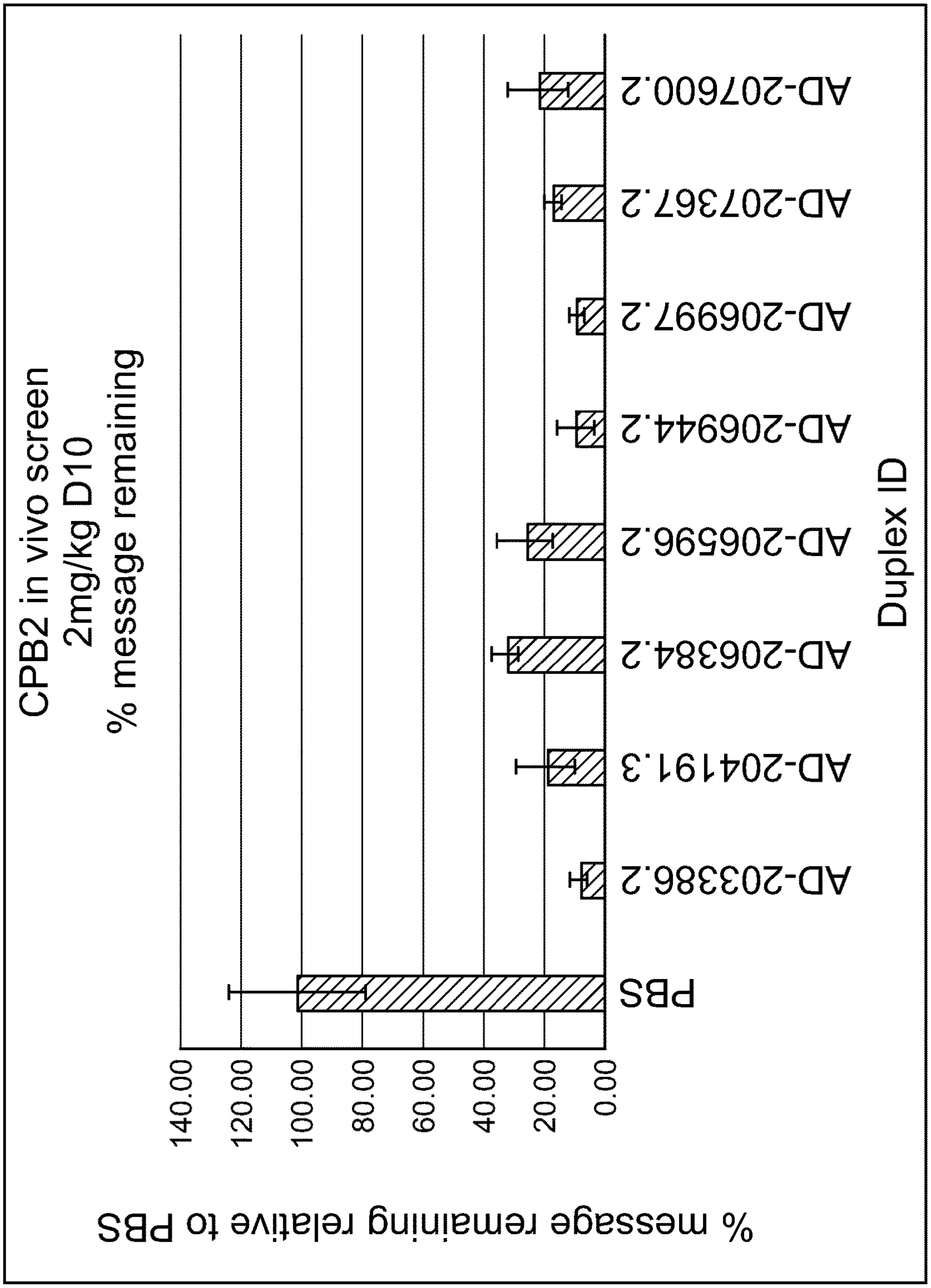
FIG. 2 is a graph showing CPB2 mRNA levels in mice (n=3 per group) subcutaneously administered a single 2 mg/kg dose of the indicated dsRNA duplexes, on day 10 post-dose. CPB2 levels are shown relative to control levels detected with PBS treatment.

CPB2 mRNA levels were compared to housekeeping gene GAPDH. The values were then normalized to the average of PBS vehicle control group. The data were expressed as percent of baseline value, and presented as mean plus standard deviation. The results, listed in Table 5 and shown in FIG. 2, demonstrate that the exemplary duplex agents tested effectively reduce the level of the CPB2 messenger RNA in vivo.

TABLE 5

CPB2 Single 2 mg/kg Dose Screen in C57BL/6 Mice
CPB2 in vivo screen 2 mg/kg D 10

| Duplex ID | % of message remaining relative to PBS | STDEV |
|---|---|---|
| PBS | 101.61 | 22.76 |
| AD-203386.2 | 8.61 | 2.81 |
| AD-204191.3 | 19.66 | 9.57 |
| AD-206384.2 | 32.82 | 4.44 |
| AD-206596.2 | 26.59 | 9.24 |
| AD-206944.2 | 9.78 | 6.20 |
| AD-206997.2 | 10.16 | 1.66 |
| AD-207367.2 | 17.19 | 2.95 |
| AD-207600.2 | 22.19 | 9.98 |

Figure 3:
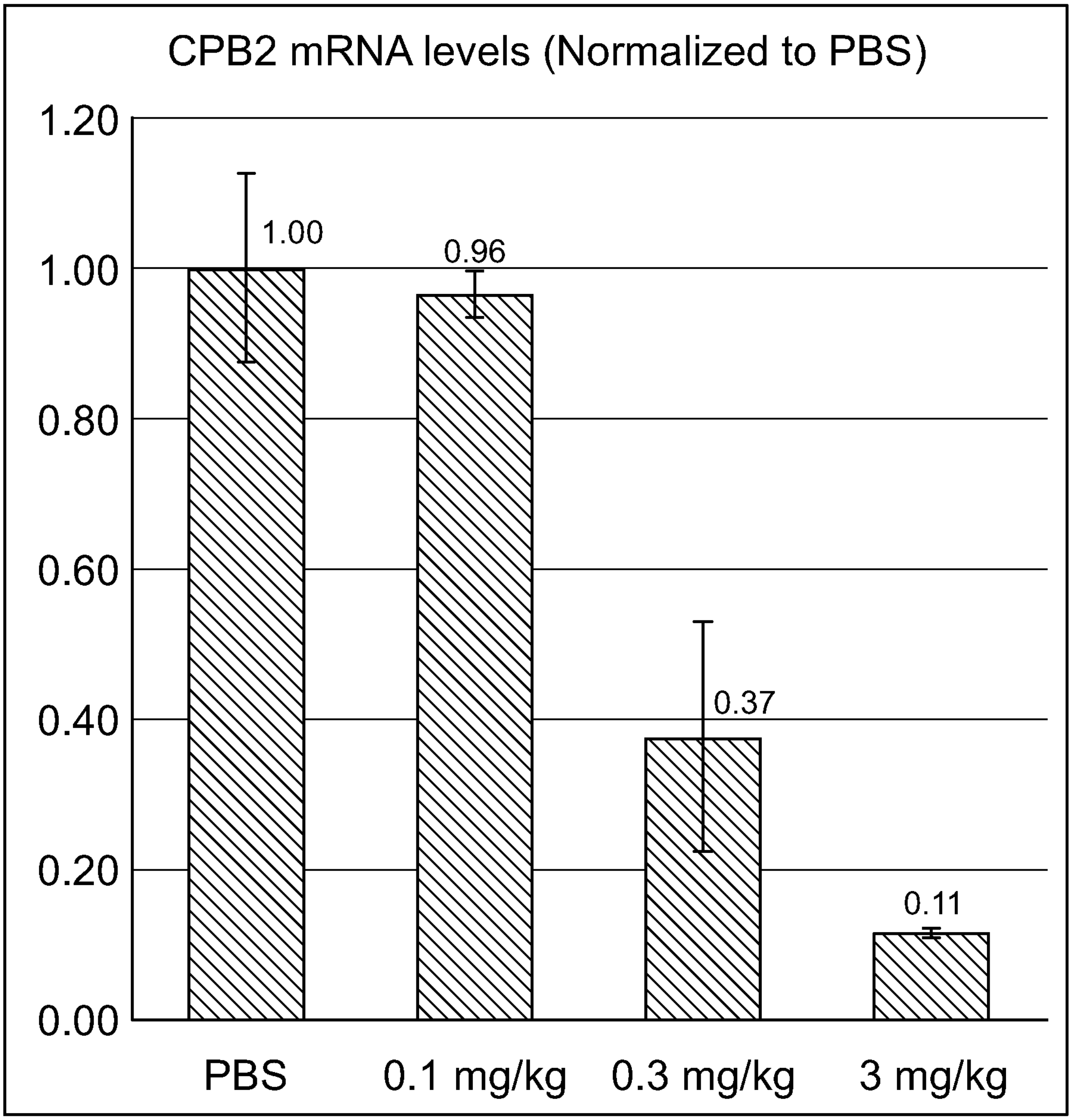
FIG. 3 is a graph showing CPB2 mRNA levels in mice (n=3 per group) subcutaneously administered a single 0.1 mg/kg, 0.3 mg/kg, or 3 mg/kg dose of AD-329750 dsRNA on day 10 post-dose. CPB2 levels are shown relative to control levels detected with PBS treatment.

The dsRNA duplex AD-329750, listed in Table 6, was selected for further in vivo analysis. Briefly, female wild-type (C57BL/6) mice (n=3 per group) were subcutaneoulsy administered a single 0.1 mg/kg, 0.3 mg/kg or 3 mg/kg dose of AD-329750 on day 0. Ten days post dosing, animal liver samples were collected and analyzed for CPB2 mRNA levels as described above. The results are shown in FIG. 3.

TABLE 6

| CPB2 Single 0.1 mg/kg, 0.3 mg/kg, and 3 mg/kg Dose Screen in C57BL/6 Mice | | | | | | |
|---|---|---|---|---|---|---|
| Duplex ID | Oligo Name | Strand | Modified Oligo Sequence 5' to 3' | SEQ ID | Unmodified sequence 5' to 3' | SEQ ID |
| AD-329750 | A-402326 | sense | csusacagAfaUfCfuFuacuacaacaL96 | 505 | CUACAGAAUCUUACUACAACA | 507 |
| | A620654 | antis | VPusGfsuugUfaGfUfaagaUfuCfuguagsasa | 506 | UGUUGUAGUAAGAUUCUGUAGAA | 508 |

Example 4. Knocking Down Hepatic TAFI or A2AP by GalNAc-siRNA Strategy Expedited Thrombolysis in a Rodent Large-Vein Electrolytic Injury Model Post-Thrombotic Syndrome (PTS) is a chronic complication of deep venous thrombosis (DVT) and has been estimated to affect 40% of DVT patients within two years. Thrombolytic therapy may reduce the burden of PTS. Thrombin activatable fibrinolysis inhibitor (TAFI) inhibits fibrinolysis by removing the fibrin c-terminal residues that are important for the binding and activation of plasminogen. In this study, a mouse large-vein electrolytic injury model was exploited to evaluate the effect of TAFI suppression on dynamic thrombosis and thrombolysis.

The aim of this study was to investigate the effect of knocking down liver-expressed TAFI on thrombolysis in a mouse large-vein electrolytic injury model. In this study, TAFI was knocked down by siRNA. Thrombus formation was induced through electrolytic injury. Platelet and fibrin deposition real-time (60 min) were monitored. The thrombus resolution (fibrinolysis) 24 hours post injury was observed by histology analysis.

More specifically, C57Bl/6 mice (3-4 months old) were subcutaneously administered a 10 mg/kg dose of AD-203386 on a weekly basis to ensure sustained TAFI mRNA reduction. On day 0, animals were subcutaneously administered a 10 mg/kg dose of AD-203386. On day 10, thrombosis formation was induced through large vein electrolytic injury (3V, 90s). Five minutes prior to this thrombus induction, rhodamine 6G (0.5 mg/kg) and anti-fibrin antibody (monoclonal 59D8) labeled with Alexa-Fluor-647 (Invitrogen) were injected into the external jugular vein. The femoral vein thrombus site was subsequently imaged with intra-vital microscopy using time-lapse capture over 60 min to record fibrin deposition. (Cooley et al., Murine model of large-vein electrolytic injury induction of thrombosis with slow resolution, Trombosis Research (2015)).

Subsequently, wounds were closed and animals recovered from anesthesia. Animals were sacrificed on day 11 (24 hrs post injury). Liver tissues were collected (liquid nitrogen). Liquid nitrogen collected liver samples (in grinding jars) can be stored at −80 C before further analysis. Electrolytic injured veins were also collected. Each harvested vein with thrombus was fixed in 4% buffered formaldehyde, processed with paraffin embedding, and sectioned longitudinally in its entirety for Haemotoxylin and Eosin staining and histomorphometric volume reconstruction of the residual thrombus and remodeling vein wall.

Figure 4A:
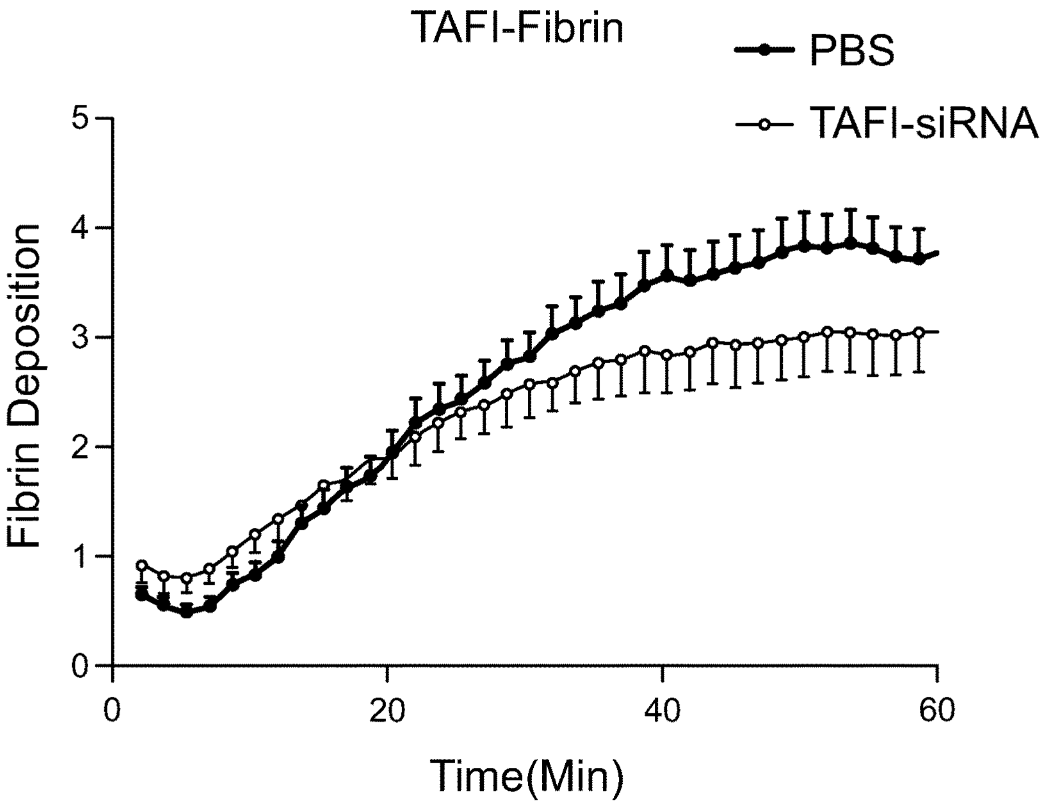
FIG. 4A is a graph showing that subcutaneous administration of AD-203386 (TAFI-siRNA) descreased fibrin deposition in a rodent large-vein electrolytic injury model.
Figure 4B:
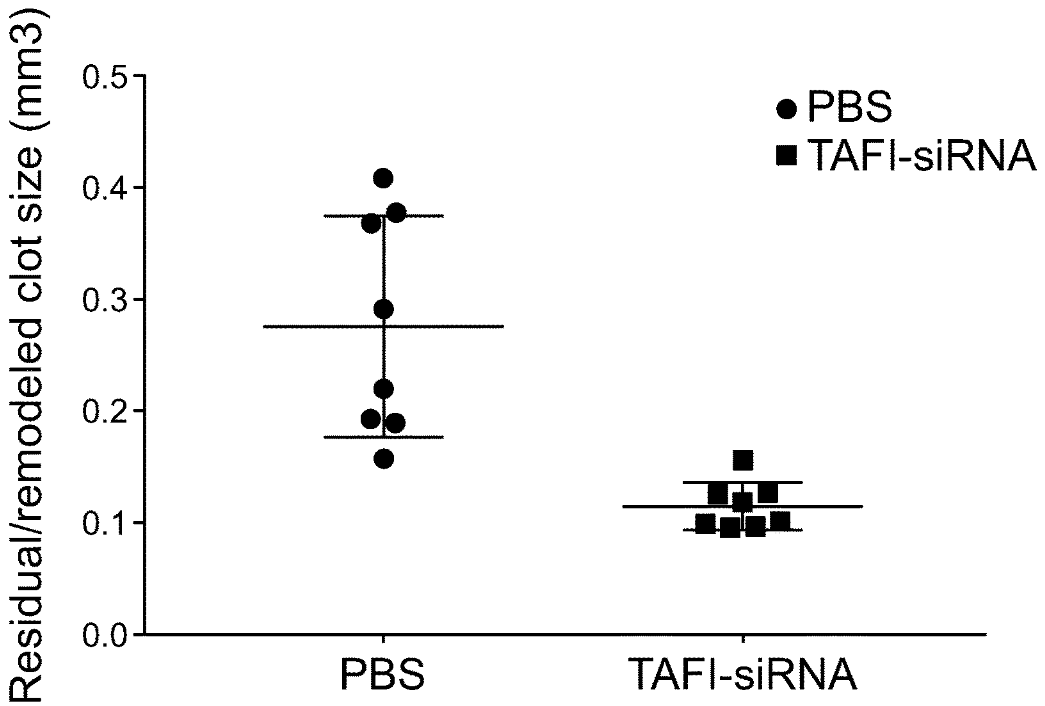
FIG. 4B is a graph showing that subcutaneous administration of AD-203386 (TAFI-siRNA) reduced the thrombus size in a rodent large-vein electrolytic injury model.

As shown in FIGS. 4A and 4B and Table 7, weekly administration of AD-203386 led to more than ninety percent (>90%) mRNA suppression. Knocking down of TAFI led to slight, yet significant, decreased fibrin deposition during the 60 minutes observation window. Twenty four (24) hours post injury, animals with TAFI knockdown displayed significant decrease in thrombus size (Table 7). Accordingly, knocking down hepatic TAFI accelerated thrombolysis in mouse electrolytic injury model and, thus, demonstrates that targeting TAFI with a dsRNA is a useful therapeutic for post thrombotic syndrome.

TABLE 7

| Thrombus Size in Large Vein Electrolytic Injuried Mice | |
|---|---|
| PBS | TAFI-siRNA |
| 0.193655 | 0.095447 |
| 0.369339 | 0.098789 |
| 0.220671 | 0.128078 |
| 0.15794 | 0.096168 |
| 0.292683 | 0.126617 |
| 0.409563 | 0.118769 |
| 0.189599 | 0.156675 |
| 0.377682 | 0.101097 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A double stranded ribonucleic acid (dsRNA) agent for inhibiting expression of carboxypeptidase B2 (CPB2) in a cell, or a salt thereof, wherein the dsRNA agent, or a salt thereof, comprises a sense strand and an antisense strand forming a double stranded region, wherein each strand is independently 19-25 nucleotides in length, wherein the antisense strand comprises at least 19 contiguous nucleotides from any one of the antisense strand nucleotide sequences selected from the group consisting of 5'-UGUUGUAGUAAGAUUCUGUAGAA-3' of SEQ ID NO: 138;

5'-UAACGGUUCUUUCUCCACAUUCG-3' of SEQ ID NO: 159;

5'-UUGAGUGAUACUGUUCAUAGUAC-3' of SEQ ID NO: 142;

5'-UUGGGAGUAUGAAUGCAUGCUGA-3' of SEQ ID NO: 145;

5'-AUAGCACGAACUGCUUCACUGGC-3' of SEQ ID NO: 153;

5'-AAACGAAUAUUUGAUGCCCAAAU-3' of SEQ ID NO: 130;

5'-UAUAGAGGAUGAUGGCUACCAGG-3' of SEQ ID NO: 149;

5'-AACGUUAAAUGGAAUUCUGCUCA-3' of SEQ ID NO: 146;

5'-UAUGUAGAAAUCCACGUGCCUCA-3' of SEQ ID NO: 139;

5'-AUUCGAUUCUUUUUCCACGUGUA-3' of SEQ ID NO: 129;

5'-UAGCUAGAUAUAAACUUUCUGAG-3' of SEQ ID NO: 147;

5'-AAAACCAAGGAAACUGAUUCAAC-3' of SEQ ID NO: 140; and

5'-UGUUGUAGUAAGAUUCUGUAGAA-3' of SEQ ID NO: 508, wherein all the nucleotides of the sense strand and all of the nucleotides of the antisense strand comprise a nucleotide modification, and wherein at least one strand is conjugated to a ligand.

2. The dsRNA agent, or a salt thereof, of claim 1, wherein at least one of the nucleotide modifications is selected from the group consisting of a deoxy-nucleotide modification, a 3'-terminal deoxy-thymine (dT) nucleotide modification, a 2'-O-methyl modification, a 2'-fluoro nucleotide modification, a 2'-deoxy-nucleotide modification, a locked nucleotide modification, an unlocked nucleotide modification, a conformationally restricted nucleotide modification, a constrained ethyl nucleotide modification, an abasic nucleotide modification, a 2'-amino-nucleotide modification, a 2'-O-allyl-nucleotide modification, 2'-C-alkyl-nucleotide modification, 2'-hydroxly-nucleotide modification, a 2'-methoxyethyl nucleotide modification, a 2'-O-alkyl-nucleotide modification, a morpholino nucleotide modification, a phosphoramidate, a non-natural base comprising nucleotide modification, a tetrahydropyran nucleotide modification, a 1,5-anhydrohexitol nucleotide modification, a cyclohexenyl nucleotide modification, a nucleotide comprising a 5'-phosphate modification, a nucleotide comprising a 5'-phosphate mimic modification, a thermally destabilizing nucleotide modification, a glycol nucleotide (GNA) modification, and a 2-O—(N-methylacetamide) modified nucleotide modification; and combinations thereof.

3. The dsRNA agent, or a salt thereof, of claim 1, wherein each strand is independently 19-23 nucleotides in length.

4. The dsRNA agent, or a salt thereof, of claim 1, wherein the ligand is conjugated to the 3' end of the sense strand of the dsRNA agent, or a salt thereof.

5. The dsRNA agent, or a salt thereof, of claim 1, wherein the ligand is an N-acetylgalactosamine (GalNAc) derivative.

6. The dsRNA agent, or a salt thereof, of claim 5, wherein the ligand is one or more GalNAc derivatives attached through a monovalent, bivalent, or trivalent branched linker.

7. The dsRNA agent, or a salt thereof, of claim 5, wherein the ligand is

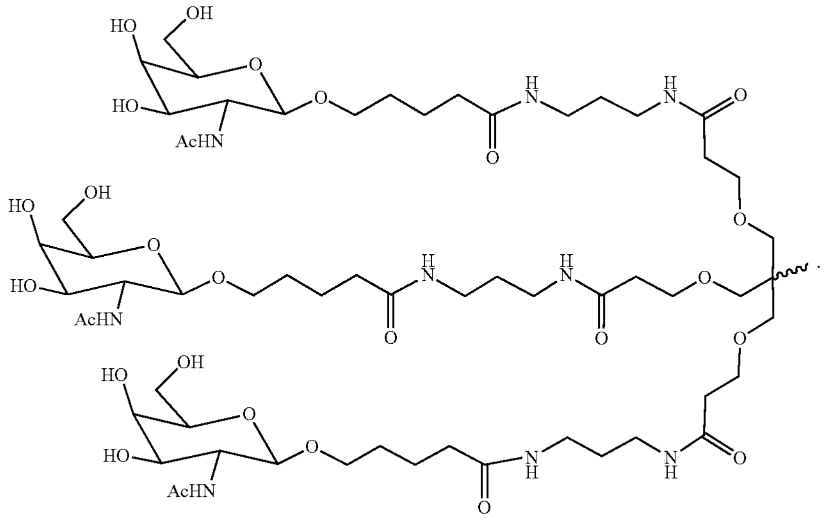 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

8. The dsRNA agent, or a salt thereof, of claim 7, wherein the dsRNA agent, or a salt thereof, is conjugated to the ligand as shown in the following schematic

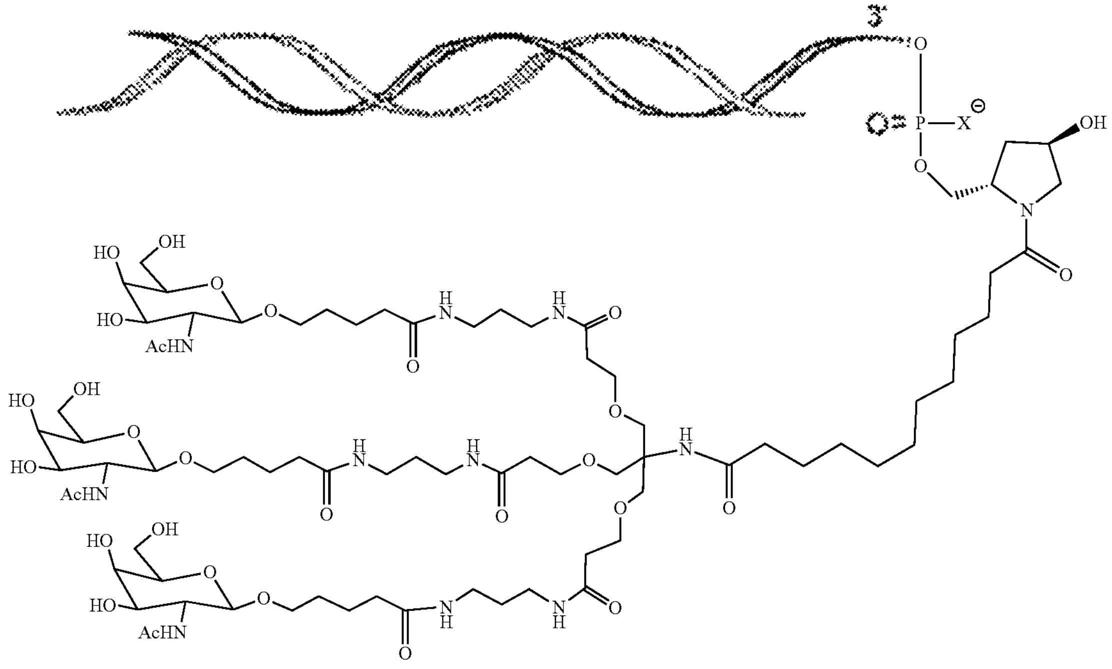

wherein X is O or S.

9. The dsRNA agent, or a salt thereof, of claim 8, wherein X is O.

10. The dsRNA agent, or a salt thereof, of claim 1, wherein the dsRNA agent, or a salt thereof, further comprises at least one phosphorothioate or methylphosphonate internucleotide linkage.

11. An isolated cell containing the dsRNA agent, or a salt thereof, of claim 1.

12. A pharmaceutical composition for inhibiting expression of a gene encoding CPB2 comprising the dsRNA agent, or a salt thereof, of claim 1.

13. A method of inhibiting expression of a CPB2 gene in a cell, the method comprising contacting the cell with the dsRNA agent, or a salt thereof, of claim 1, thereby inhibiting expression of the CPB2 gene in the cell.

14. A method of treating a CPB2-associated disorder in a subject, the method comprising administering to the subject the dsRNA agent, or a salt thereof, of claim 1, thereby treating the CPB2-associated disorder in the subject.

15. The method of claim 14, wherein the CPB2-associated disorder is selected from the group consisting of plasminogen deficiency, venous thrombosis, venous thromboembolism, deep vein thrombosis, pulmonary embolism, prosthetic valve thrombosis, post-thrombotic syndrome, atherothrombosis, heart attack, stroke, fibrinolytic disorders, hypofibrinolysis, disfibrinolysis, ischemic stroke, atrial fibrillation, myocardial infarction, peripheral arterial disease, dynamic thrombosis, coronary artery disease, microvascular thrombosis, ischemic brain injury, brain swelling, brain hemorrhage and death after thromboembolic stroke.

16. The method of claim 14, further comprising administering to the subject an additional therapeutic agent for treatment of thrombosis.

17. A kit comprising the dsRNA agent, or a salt thereof, of claim 1.

18. The dsRNA agent, or a salt thereof, of claim 1, wherein the antisense strand comprises any one of the antisense strand nucleotide sequence selected from the group consisting of

```
5'-UGUUGUAGUAAGAUUCUGUAGAA-3' of SEQ ID NO: 138;

5'-UAACGGUUCUUUCUCCACAUUCG-3' of SEQ ID NO: 159

5'-UUGAGUGAUACUGUUCAUAGUAC-3' of SEQ ID NO: 142;

5'-UUGGGAGUAUGAAUGCAUGCUGA-3' of SEQ ID NO: 145;

5'-AUAGCACGAACUGCUUCACUGGC-3' of SEQ ID NO: 153;

5'-AAACGAAUAUUUGAUGCCCAAAU-3' of SEQ ID NO: 130;

5'-UAUAGAGGAUGAUGGCUACCAGG-3' of SEQ ID NO: 149;

5'-AACGUUAAAUGGAAUUCUGCUCA-3' of SEQ ID NO: 146;

5'-UAUGUAGAAAUCCACGUGCCUCA-3' of SEQ ID NO: 139;

5'-AUUCGAUUCUUUUUCCACGUGUA-3' of SEQ ID NO: 129;

5'-UAGCUAGAUAUAAACUUUCUGAG-3' of SEQ ID NO: 147;

5'-AAAACCAAGGAAACUGAUUCAAC-3' of SEQ ID NO: 140;
and

5'-UGUUGUAGUAAGAUUCUGUAGAA-3' of SEQ ID NO: 508.
```

19. The dsRNA agent, or a salt thereof, of claim 1, wherein the sense strand and the antisense strand comprise any one of the sense strand and antisense strand nucleotide sequences selected from the group consisting of

```
(i)
5'-CUACAGAAUCUUACUACAACA-3' of SEQ ID NO: 44 and
5'-UGUUGUAGUAAGAUUCUGUAGAA-3' of SEQ ID NO: 138;

(ii)
5'-AAUGUGGAGAAAGAACCGUUA-3' of SEQ ID NO: 65 and
5'-UAACGGUUCUUUCUCCACAUUCG-3' of SEQ ID NO: 159

(iii)
5'-ACUAUGAACAGUAUCACUCAA-3' of SEQ ID NO: 48 and
5'-UUGAGUGAUACUGUUCAUAGUAC-3' of SEQ ID NO: 142;

(iv)
5'-AGCAUGCAUUCAUACUCCCAA-3' of SEQ ID NO: 51 and
5'-UUGGGAGUAUGAAUGCAUGCUGA-3' of SEQ ID NO: 145;

(v)
5'-CAGUGAAGCAGUUCGUGCUAU-3' of SEQ ID NO: 59 and
5'-AUAGCACGAACUGCUUCACUGGC-3' of SEQ ID NO: 153;

(vi)
5'-UUGGGCAUCAAAUAUUCGUUU-3' of SEQ ID NO: 36 and
5'-AAACGAAUAUUUGAUGCCCAAAU-3' of SEQ ID NO: 130;
```

-continued

```
(vii)
5'-UGGUAGCCAUCAUCCUCUAUA-3' of SEQ ID NO: 55 and
5'-UAUAGAGGAUGAUGGCUACCAGG-3' of SEQ ID NO: 149;

(viii)
5'-AGCAGAAUUCCAUUUAACGUU-3' of SEQ ID NO: 52 and
5'-AACGUUAAAUGGAAUUCUGCUCA-3' of SEQ ID NO: 146;

(ix)
5'-AGGCACGUGGAUUUCUACAUA-3' of SEQ ID NO: 45 and
5'-UAUGUAGAAAUCCACGUGCCUCA-3' of SEQ ID NO: 139;

(x)
5'-CACGUGGAAAAAGAAUCGAAU-3' of SEQ ID NO: 35 and
5'-AUUCGAUUCUUUUUCCACGUGUA-3' of SEQ ID NO: 129;

(xi)
5'-CAGAAAGUUUAUAUCUAGCUA-3' of SEQ ID NO: 53 and
5'-UAGCUAGAUAUAAACUUUCUGAG-3' of SEQ ID NO: 147;

(xii)
5'-UGAAUCAGUUUCCUUGGUUUU-3' of SEQ ID NO: 46 and
5'-AAAACCAAGGAAACUGAUUCAAC-3' of SEQ ID NO: 140;
and

(xiii)
5'-CUACAGAAUCUUACUACAACA-3' of SEQ ID NO: 507 and
5'-UGUUGUAGUAAGAUUCUGUAGAA-3' of SEQ ID NO: 508.
```

20. The dsRNA agent, or a salt thereof, of claim 18, wherein the sense strand and the antisense strand comprise any one of the sense strand and antisense strand nucleotide sequences selected from the group consisting of

```
(i)
5'-csusacagAfaUfCfUfuacuacaaca-3' of
SEQ ID NO: 232 and
5'-usGfsuugUfaGfUfaagaUfuCfuguagsasa-3' of
SEQ ID NO: 326;

(ii)
5' -asasugugGfaGfAfAfagaaccguua-3' of
SEQ ID NO: 253 and
5'-usAfsacgGfuUfCfuuucUfcCfacauuscsg-3' of
SEQ ID NO: 347;

(iii)
5'-ascsuaugAfaCfAfGfuaucacucaa-3' of
SEQ ID NO: 236 and
5'-usUfsgag UfgAfUfacugUfuCfauagusasc-3' of
SEQ ID NO: 330;

(iv)
5'-asgscaugCfaUfUfCfauacucccaa-3' of
SEQ ID NO: 239 and
5'-usUfsgggAfgUfAfugaaUfgCfaugcusgsa-3' of
SEQ ID NO: 333;

(v)
5'-csasgugaAfgCfAfGfuucgugcuau-3' of
SEQ ID NO: 247 and
5'-asUfsagcAfcGfAfacugCfuUfcacugsgsc-3' of
SEQ ID NO: 341;

(vi)
5'-usgsgggcAfuCfAfAfauauucguuu-3' of
SEQ ID NO: 224 and
5'-asAfsacgAfaUfAfuuugAfuGfcccaasasu-3' of
SEQ ID NO: 318;

(vii)
5'-usgsguagCfcAfUfCfauccucuaua-3' of
SEQ ID NO: 243 and
5'-usAfsuag AfgGfAfugauGfgCfuaccasgsg-3' of
SEQ ID NO: 337;
```

-continued (viii)
5'-asgscagaAfuUfCfCfauuuaacguu-3' of SEQ ID NO: 240 and
5'-asAfscguUfaAfAfuggaAfuUfcugcuscsa-3' of SEQ ID NO: 334;

(ix)
5'-asgsgcacGfuGfGfAfuuucuacaua-3' of SEQ ID NO: 233 and
5'-usAfsuguAfgAfAfauccAfcGfugccuscsa-3' of SEQ ID NO: 327;

(x)
5'-csascgugGfaAfAfAfagaaucgaau-3' of SEQ ID NO: 223 and
5'-asUfsucgAfuUfCfuuuuUfcCfacgugsusa-3' of SEQ ID NO: 317;

(xi)
5'-csasgaaaGfuUfUfAfuaucuagcua-3' of SEQ ID NO: 241 and
5'-usAfsgcuAfgAfUfauaaAfcUfuucugsasg-3' of SEQ ID NO: 335;

(xii)
5'-usgsaaucAfgUfUfUfccuugguuuu-3' of SEQ ID NO: 234 and
5'-asAfsaacCfaAfGfgaaaCfuGfauucasasc-3' of SEQ ID NO: 328; and (xiii)
5'-csusacagAfaUfCfUfuacuacaaca-3' of SEQ ID NO: 505 and
5'-VPusGfsuugUfaGfUfaagaUfuCfuguagsasa-3' of SEQ ID NO: 506.

* * * * *

SEQUENCE LISTING

<160> NUMBER OF SEQ ID NOS: 532

<210> SEQ ID NO 1
<211> LENGTH: 1724
<212> TYPE: DNA
<213> ORGANISM: Homo sapiens

<400> SEQUENCE: 1
gttgtacaga aaattgctgt tgggatgaag ctttgcagcc ttgcagtcct tgtacccatt 60

-continued

```
gttctcttct gtgagcagca tgtcttcgcg tttcagagtg gccaagttct agctgctctt    120
cctagaacct ctaggcaagt tcaagttcta cagaatctta ctacaacata tgagattgtt    180
ctctggcagc cggtaacagc tgaccttatt gtgaagaaaa aacaagtcca tttttttgta    240
aatgcatctg atgtcgacaa tgtgaaagcc catttaaatg tgagcggaat tccatgcagt    300
gtcttgctgg cagatgtgga agatcttatt caacagcaga tttccaacga cacagtcagc    360
ccccgagcct ccgcatcgta ctatgaacag tatcactcac taaatgaaat ctattcttgg    420
atagaattta taactgagag gcatcctgat atgcttacaa aaatccacat tggatcctca    480
tttgagaagt acccactcta tgttttaaag gtttctggaa aagaacaagc agccaaaaat    540
gccatatgga ttgactgtgg aatccatgcc agagaatgga tctctcctgc tttctgcttg    600
tggttcatag gccatataac tcaattctat gggataatag ggcaatatac caatctcctg    660
aggcttgtgg atttctatgt tatgccagtg gttaatgtgg atggttatga ctactcatgg    720
aaaaagaatc gaatgtggag aaagaaccgt tctttctatg cgaacaatca ttgcatcgga    780
acagacctga ataggaactt tgcttccaaa cactggtgtg aggaaggtgc atccagttcc    840
tcatgctcgg aaacctactg tggactttat cctgagtcag aaccagaagt gaaggcagtg    900
gctagtttct tgagaagaaa tatcaaccag attaaagcat acatcagcat gcattcatac    960
tcccagcata tagtgtttcc atattcctat acacgaagta aaagcaaaga ccatgaggaa   1020
ctgtctctag tagccagtga agcagttcgt gctattgaga aaattagtaa aaataccagg   1080
tatacacatg gccatggctc agaaacctta tacctagctc ctggaggtgg ggacgattgg   1140
atctatgatt tgggcatcaa atattcgttt acaattgaac ttcgagatac gggcacatac   1200
ggattcttgc tgccggagcg ttacatcaaa cccacctgta gagaagcttt tgccgctgtc   1260
tctaaaatag cttggcatgt cattaggaat gtttaatgcc cctgatttta tcattctgct   1320
tccgtatttt aatttactga ttccagcaag accaaatcat tgtatcaaat tatttttaag   1380
ttttatccgt agttttgata aaagattttc ctattccttg gttctgtcag agaacctaat   1440
aagtgctact ttgccattaa ggcagactag ggttcatgtc tttttaccct ttaaaaaaaa   1500
ttgtaaaagt ctagttacct actttttctt tgattttcga cgtttgacta gccatctcaa   1560
gcaagtttcg acgtttgact agccatctca agcaagttta atcaatgatc atctcacgct   1620
gatcattgga tcctactcaa caaaaggaag ggtggtcaga agtacattaa agatttctgc   1680
tccaaatttt caataaattt ctgcttgtgc ctttagaaat acaa                    1724
```

<210> SEQ ID NO 2
<211> LENGTH: 1724
<212> TYPE: DNA
<213> ORGANISM: Homo sapiens

<400> SEQUENCE: 2

```
ttgtatttct aaaggcacaa gcagaaattt attgaaaatt tggagcagaa atctttaatg     60
tacttctgac cacccttcct tttgttgagt aggatccaat gatcagcgtg agatgatcat    120
tgattaaact tgcttgagat ggctagtcaa acgtcgaaac ttgcttgaga tggctagtca    180
aacgtcgaaa atcaaagaaa aagtaggtaa ctagactttt acaatttttt ttaaagggta    240
aaaagacatg aaccctagtc tgccttaatg gcaaagtagc acttattagg ttctctgaca    300
gaaccaagga ataggaaaat cttttatcaa aactacggat aaaacttaaa aataatttga    360
tacaatgatt tggtcttgct ggaatcagta aattaaaata cggaagcaga atgataaaat    420
caggggcatt aaacattcct aatgacatgc caagctattt tagagacagc ggcaaaagct    480
```

tctctacagg tgggtttgat gtaacgctcc ggcagcaaga atccgtatgt gcccgtatct 540
cgaagttcaa ttgtaaacga atatttgatg cccaaatcat agatccaatc gtccccacct 600
ccaggagcta ggtataaggt ttctgagcca tggccatgtg tatacctggt atttttacta 660
attttctcaa tagcacgaac tgcttcactg gctactagag acagttcctc atggtctttg 720
cttttacttc gtgtatagga atatggaaac actatatgct gggagtatga atgcatgctg 780
atgtatgctt taatctggtt gatatttctt ctcaagaaac tagccactgc cttcacttct 840
ggttctgact caggataaag tccacagtag gtttccgagc atgaggaact ggatgcacct 900
tcctcacacc agtgtttgga agcaaagttc ctattcaggt ctgttccgat gcaatgattg 960
ttcgcataga aagaacggtt ctttctccac attcgattct ttttccatga gtagtcataa 1020
ccatccacat taaccactgg cataacatag aaatccacaa gcctcaggag attggtatat 1080
tgccctatta tcccatagaa ttgagttata tggcctatga accacaagca gaaagcagga 1140
gagatccatt ctctggcatg gattccacag tcaatccata tggcattttt ggctgcttgt 1200
tcttttccag aaacctttaa aacatagagt gggtacttct caaatgagga tccaatgtgg 1260
atttttgtaa gcatatcagg atgcctctca gttataaatt ctatccaaga atagatttca 1320
tttagtgagt gatactgttc atagtacgat gcggaggctc gggggctgac tgtgtcgttg 1380
gaaatctgct gttgaataag atcttccaca tctgccagca agacactgca tggaattccg 1440
ctcacattta aatgggcttt cacattgtcg acatcagatg catttacaaa aaaatggact 1500
tgtttttct tcacaataag gtcagctgtt accggctgcc agagaacaat ctcatatgtt 1560
gtagtaagat tctgtagaac ttgaacttgc ctagaggttc taggaagagc agctagaact 1620
tggccactct gaaacgcgaa gacatgctgc tcacagaaga gaacaatggg tacaaggact 1680
gcaaggctgc aaagcttcat cccaacagca atttctgta caac 1724

<210> SEQ ID NO 3
<211> LENGTH: 1729
<212> TYPE: DNA
<213> ORGANISM: Macaca fascicularis

<400> SEQUENCE: 3
gcaatcaatg atctgggtct ttctcttcag agaaatttgt tgtacagaaa attgctgttg 60
ggatgaagct ttgcagtctt gcagtccttg tacccattgt tctcttctgt gagcagcatg 120
tcttcgcgtt tcagagtggc caggttctag ctgctcttcc tagaacctct aggcaagttc 180
aagtgctaca gaatcttact acaacatatg agattgttct ctggcagccg gtaacatctg 240
accttattgc gaagaaaaaa caagtccatt tttttgtaaa ttcatctgat gtcgacattg 300
tgaaagccca tttaaatgtg agcggaattc catgcagtgt cctgctggca gatgtggaag 360
atcttattca acagcagatt tccaatgaca cagtcagccc ccgagcctcc gcatcgtact 420
atgaacagta tcactcacta aatgaaatct attcttggat agaacttata actgagaagt 480
atcctgatat gcttacaaaa atccacattg gatcctccta tgagaagcac ccactttatg 540
ttttaaaggt ttctggaaaa gaacaaacag ccaaaaatgc catgtggatt gactgtggaa 600
tccatgccag agaatggatc tcccctgctt tctgcttgtg gttcataggc catataactg 660
aacactatgg gataataggg gaatatacca atcttctgag gcatgtggat ttctatgtta 720
tgccagtggt taatgtggat ggttatgact actcatggaa aaagaatcga atgtggagaa 780
agaaccgttc tttctatgcg aacaatcgtt gcatcggaac agacctgaac aggaactttg 840

-continued

```
cgtccaaaca ctggtgtgag gaaggtgcat ccagtttctc atgctcggaa acctactgtg    900

gactttatcc tgagtcagaa ccagaagcga aggcggtggc taatttcttg agaagaaata    960

tcaaccacat taaagcatac atcagcatgc attcatactc ccagcatata gtgtttccat   1020

attcctatac tcgaagcaaa agcaaagacc acgaggaatt gtctctagta gccagtgaag   1080

cagttcgtgc tattcagaaa accagtaaaa atatcaggta tacacatggc cgtggctcag   1140

aaaccttata cctagctcct ggaggtgcgg acgattggat ctatgatttg ggcatcaaat   1200

attcgtttac aattgaactt cgagatacgg gcaaatacgg attcttgctg ccagagcgtt   1260

acatcaaacc cacttgtaaa gacgcttttg ccgctgtctc taaaatagct tggcatgtca   1320

ttaggaatgt ttaatgccct cgattttatc attctgcttt cgtattttaa tttactgatt   1380

ccagcaagac taaatcattg tatcagatta tttttaagtt ttatccgtag tttcgataaa   1440

agattttccc ataccttggt tttgtcagag aacctaataa gtgctacttt gacattaagg   1500

cagacaaggg ttcatgtctt tttacctttc aaaaaaaaat tgtaaaagtc tagctaccta   1560

ctttttcttt gatttccgac gtctgattag ccatctcaag caagtttaat aacaagtttc   1620

atgctgatcg ttggatccta ctcaataaaa ggaagggtgg tcagaagtac attaaagatt   1680

tctgctccaa attttcaata aatttctgct tgtgccttca gaaatacaa               1729
```

```
<210> SEQ ID NO 4
<211> LENGTH: 1729
<212> TYPE: DNA
<213> ORGANISM: Macaca fascicularis

<400> SEQUENCE: 4

ttgtatttct gaaggcacaa gcagaaattt attgaaaatt tggagcagaa atctttaatg     60

tacttctgac cacccttcct tttattgagt aggatccaac gatcagcatg aaacttgtta    120

ttaaacttgc ttgagatggc taatcagacg tcggaaatca aagaaaaagt aggtagctag    180

acttttacaa tttttttttg aaaggtaaaa agacatgaac ccttgtctgc cttaatgtca    240

aagtagcact tattaggttc tctgacaaaa ccaaggtatg ggaaaatctt ttatcgaaac    300

tacggataaa acttaaaaat aatctgatac aatgatttag tcttgctgga atcagtaaat    360

taaaatacga aagcagaatg ataaaatcga gggcattaaa cattcctaat gacatgccaa    420

gctattttag agacagcggc aaaagcgtct ttacaagtgg gtttgatgta acgctctggc    480

agcaagaatc cgtatttgcc cgtatctcga agttcaattg taaacgaata tttgatgccc    540

aaatcataga tccaatcgtc cgcacctcca ggagctaggt ataaggtttc tgagccacgg    600

ccatgtgtat acctgatatt tttactggtt ttctgaatag cacgaactgc ttcactggct    660

actagagaca attcctcgtg gtctttgctt ttgcttcgag tataggaata tggaaacact    720

atatgctggg agtatgaatg catgctgatg tatgctttaa tgtggttgat atttcttctc    780

aagaaattag ccaccgcctt cgcttctggt tctgactcag gataaagtcc acagtaggtt    840

tccgagcatg agaaactgga tgcaccttcc tcacaccagt gtttggacgc aaagttcctg    900

ttcaggtctg ttccgatgca acgattgttc gcatagaaag aacggttctt tctccacatt    960

cgattctttt tccatgagta gtcataacca tccacattaa ccactggcat aacatagaaa   1020

tccacatgcc tcagaagatt ggtatattcc cctattatcc catagtgttc agttatatgg   1080

cctatgaacc acaagcagaa agcaggggag atccattctc tggcatggat tccacagtca   1140

atccacatgg catttttggc tgtttgttct tttccagaaa cctttaaaac ataaagtggg   1200

tgcttctcat aggaggatcc aatgtggatt tttgtaagca tatcaggata cttctcagtt   1260
```

```
ataagttcta tccaagaata gatttcattt agtgagtgat actgttcata gtacgatgcg   1320

gaggctcggg ggctgactgt gtcattggaa atctgctgtt gaataagatc ttccacatct   1380

gccagcagga cactgcatgg aattccgctc acatttaaat gggctttcac aatgtcgaca   1440

tcagatgaat ttacaaaaaa atggacttgt tttttcttcg caataaggtc agatgttacc   1500

ggctgccaga gaacaatctc atatgttgta gtaagattct gtagcacttg aacttgccta   1560

gaggttctag gaagagcagc tagaacctgg ccactctgaa acgcgaagac atgctgctca   1620

cagaagagaa caatgggtac aaggactgca agactgcaaa gcttcatccc aacagcaatt   1680

ttctgtacaa caaatttctc tgaagagaaa gacccagatc attgattgc              1729
```

```
<210> SEQ ID NO 5
<211> LENGTH: 1503
<212> TYPE: DNA
<213> ORGANISM: Mus musculus

<400> SEQUENCE: 5

gaaggctctt aggcaattag ttacctggga ctttctcccc aagggcttgc tcacaagtca     60

ctgttgggat gaagcttcat ggccttggaa tcctggtagc catcatcctc tatgagcagc    120

atggcttcgc ctttcagagt ggccaggttt tatctgctct tccaagaacc tccaggcaag    180

ttcaactact tcagaatctt actacaacgt atgaggtcgt tctctggcag ccagtgacag    240

ctgaattcat cgagaagaaa aaggaagtcc actttttttgt gaatgcgtct gatgtcgaca   300

gtgtcaaagc gcatttaaat gtgagcagaa ttccatttaa cgttctgatg aacaacgtgg    360

aggacctaat tgaacagcag actttcaatg acacggtcag cccccgcgcc tccgcttcat    420

actatgagca gtatcactcg ctaaatgaaa tctattcctg gatagaagtc ataactgaac    480

agcatcctga catgctccag aaaatctaca tcggatcatc attcgagaag tacccacttt    540

atgttttaaa ggtctcagga aaggaacaaa gaatcaaaaa tgccatctgg atcgactgtg    600

gaatccatgc cagagaatgg atttcacctg ctttctgttt gtggttcata ggctacgtga    660

cacaattcca tgggaaagaa aatctgtata ccagacttct gaggcacgtg gatttctaca    720

tcatgcccgt gatgaacgtg gatggctatg actacacgtg gaaaaagaat cgaatgtgga    780

ggaagaaccg ctctgctcac aagaacaacc gctgcgtggg cacagacctg aacaggaact    840

tcgcttccaa acactggtgt gagaaaggtg cgtcaagttc ctcctgctct gaaacctact    900

gtggacttta tcctgagtct gagccagagg tgaaggcagt ggctgacttc ttgagaagaa    960

atatcgacca cattaaagct tacatcagta tgcactcata ctcccaacaa atactgtttc   1020

cctattccta taacagaagc aaaagcaagg accacgaaga actgtctcta gtggccagcg   1080

aagcagttcg tgcaattgaa agtattaata aaaacaccag gtacacacac ggcagtggct   1140

cagaaagttt atatctagct cctggaggtt ctgacgattg gatctatgat ttgggcatca   1200

aatattcgtt tacaattgag ctccgagata caggcagata cggattcttg ctgcctgaga   1260

gatacatcaa acccacttgt gcagaagctt tggccgccat ctctaaaata gtttggcatg   1320

tcatcaggaa cacttaatgc cctaacctcc gctctcatta tttttatttt attgatttca   1380

gcaacactta actgttgcat tagcttctaa gttgaatcag tttccttggt tttgttgaag   1440

aataaaaagc acactacttt gagcttaaga gtgaaaaaaa aaaaaaaaaa aaaaaaaaaa   1500

aaa                                                                 1503

<210> SEQ ID NO 6
```

<211> LENGTH: 1503
<212> TYPE: DNA
<213> ORGANISM: Mus musculus

<400> SEQUENCE: 6

```
ttttttttt ttttttttt ttttttttt cactcttaag ctcaaagtag tgtgcttttt     60

attcttcaac aaaaccaagg aaactgattc aacttagaag ctaatgcaac agttaagtgt    120

tgctgaaatc aataaaataa aaataatgag agcggaggtt agggcattaa gtgttcctga    180

tgacatgcca aactatttta gagatggcgg ccaaagcttc tgcacaagtg ggtttgatgt    240

atctctcagg cagcaagaat ccgtatctgc ctgtatctcg gagctcaatt gtaaacgaat    300

atttgatgcc caaatcatag atccaatcgt cagaacctcc aggagctaga tataaacttt    360

ctgagccact gccgtgtgtg tacctggtgt ttttattaat actttcaatt gcacgaactg    420

cttcgctggc cactagagac agttcttcgt ggtccttgct tttgcttctg ttataggaat    480

agggaaacag tatttgttgg gagtatgagt gcatactgat gtaagcttta atgtggtcga    540

tatttcttct caagaagtca gccactgcct tcacctctgg ctcagactca ggataaagtc    600

cacagtaggt ttcagagcag gaggaacttg acgcaccttt ctcacaccag tgtttggaag    660

cgaagttcct gttcaggtct gtgcccacgc agcggttgtt cttgtgagca gagcggttct    720

tcctccacat tcgattcttt ttccacgtgt agtcatagcc atccacgttc atcacgggca    780

tgatgtagaa atccacgtgc ctcagaagtc tggtatacag attttctttc ccatggaatt    840

gtgtcacgta gcctatgaac cacaaacaga aagcaggtga aatccattct ctggcatgga    900

ttccacagtc gatccagatg gcatttttga ttctttgttc ctttcctgag acctttaaaa    960

cataaagtgg gtacttctcg aatgatgatc cgatgtagat tttctggagc atgtcaggat   1020

gctgttcagt tatgacttct atccaggaat agatttcatt tagcgagtga tactgctcat   1080

agtatgaagc ggaggcgcgg gggctgaccg tgtcattgaa agtctgctgt tcaattaggt   1140

cctccacgtt gttcatcaga acgttaaatg gaattctgct cacatttaaa tgcgctttga   1200

cactgtcgac atcagacgca ttcacaaaaa agtggacttc ctttttcttc tcgatgaatt   1260

cagctgtcac tggctgccag agaacgacct catacgttgt agtaagattc tgaagtagtt   1320

gaacttgcct ggaggttctt ggaagagcag ataaaacctg gccactctga aaggcgaagc   1380

catgctgctc atagaggatg atggctacca ggattccaag gccatgaagc ttcatcccaa   1440

cagtgacttg tgagcaagcc cttggggaga aagtcccagg taactaattg cctaagagcc   1500

ttc                                                                 1503
```

<210> SEQ ID NO 7
<211> LENGTH: 1460
<212> TYPE: DNA
<213> ORGANISM: Rattus norvegicus

<400> SEQUENCE: 7

```
cgaggaactt ggctgctcaa caagtcactg ttgggatgaa gctttatggc cttggagtcc     60

tggtagccat catcctctat gagaagcatg gccttgcctt tcagagtggc catgttctat    120

ctgctctccc tcgaacctcc aggcaagttc aacttcttca gaatctcact acaacttacg    180

aggttgttct ctggcagcca gtgacagctg aattcattga gaagaaaaag gaagtccact    240

tctttgtgaa tgcgtctgat gtcaacagtg tcaaagccta tttaaatgcg agcagaattc    300

catttaacgt cctgatgaac aacgtggagg atctaattca acagcagacg tccaatgaca    360

ctgttagccc ccgagcctcc tcctcatact atgaacagta tcactcgtta aatgaaatct    420
```

```
attcctggat agaagttata actgaacagc accctgacat gctccagaaa atctacattg    480

gatcctcata tgaaaagtac ccactttatg tgttaaaggt ctcaggaaag gaacacagag    540

tcaaaaatgc catatggatc gactgtggaa tccatgccag agagtggatt tcaccagctt    600

tctgcttgtg gttcataggc tatgtaacgc aattccatgg gaaagaaaat acatacacca    660

gacttctgag gcacgtggat ttctacatta tgccagtgat gaatgtggac ggctacgact    720

acacgtggaa aaagaatcga atgtggagaa agaaccgctc tgtccacatg aacaaccgct    780

gcgtgggcac agacctgaac aggaacttcg cttccaaaca ctggtgtgag aaaggcgcat    840

caagtttctc ctgctctgag acctactgtg gactttaccc tgagtctgag ccagaggtga    900

aggcagtggc tgacttcctg aggagaaata tcaaccacat taaagcttac atcagtatgc    960

actcatactc ccagcaaata ctgtttccct attcctacaa cagaagcaaa agcaaggacc   1020

acgaggaact gtctctagtg gccagcgaag cagttcgtgc cattgaaagt attaataaaa   1080

acaccaggta cacacatggc agtggctcag aaagtttata tctagctcct ggaggttctg   1140

atgattggat ctatgatttg ggcatcaaat attcgtttac gattgaactt cgggatacag   1200

gcagatacgg gttcttgctg cctgagagat tcatcaaacc cacttgcgca gaagctttgg   1260

ccgcagtctc taaaatagct tggcatgtca tcaggaacag ttaacaccct ttcctctgct   1320

ctcattactt ttattttatt gatttcagca acactaaatt gttgcactag cttctaagtt   1380

taatcagttt ccttggtttt gttgaagaat aaaaagcaca ctactttgag cttaaaaaaa   1440

aaaaaaaaaa aaaaaaaaaa                                               1460
```

<210> SEQ ID NO 8
<211> LENGTH: 1460
<212> TYPE: DNA
<213> ORGANISM: Rattus norvegicus

<400> SEQUENCE: 8

```
tttttttttt tttttttttt ttttttaag ctcaaagtag tgtgcttttt attcttcaac      60

aaaaccaagg aaactgatta aacttagaag ctagtgcaac aatttagtgt tgctgaaatc    120

aataaaataa aagtaatgag agcagaggaa agggtgttaa ctgttcctga tgacatgcca    180

agctatttta gagactgcgg ccaaagcttc tgcgcaagtg ggtttgatga atctctcagg    240

cagcaagaac ccgtatctgc ctgtatcccg aagttcaatc gtaaacgaat atttgatgcc    300

caaatcatag atccaatcat cagaacctcc aggagctaga tataaacttt ctgagccact    360

gccatgtgtg tacctggtgt ttttattaat actttcaatg gcacgaactg cttcgctggc    420

cactagagac agttcctcgt ggtccttgct tttgcttctg ttgtaggaat agggaaacag    480

tatttgctgg gagtatgagt gcatactgat gtaagcttta atgtggttga tatttctcct    540

caggaagtca gccactgcct tcacctctgg ctcagactca gggtaaagtc cacagtaggt    600

ctcagagcag gagaaacttg atgcgccttt ctcacaccag tgtttggaag cgaagttcct    660

gttcaggtct gtgcccacgc agcggttgtt catgtggaca gagcggttct ttctccacat    720

tcgattcttt ttccacgtgt agtcgtagcc gtccacattc atcactggca taatgtagaa    780

atccacgtgc ctcagaagtc tggtgtatgt attttctttc ccatggaatt gcgttacata    840

gcctatgaac cacaagcaga aagctggtga aatccactct ctggcatgga ttccacagtc    900

gatccatatg gcatttttga ctctgtgttc ctttcctgag acctttaaca cataaagtgg    960

gtacttttca tatgaggatc caatgtagat tttctggagc atgtcagggt gctgttcagt   1020
```

-continued

```
tataacttct atccaggaat agatttcatt taacgagtga tactgttcat agtatgagga   1080

ggaggctcgg gggctaacag tgtcattgga cgtctgctgt tgaattagat cctccacgtt   1140

gttcatcagg acgttaaatg gaattctgct cgcatttaaa taggctttga cactgttgac   1200

atcagacgca ttcacaaaga agtggacttc ctttttcttc tcaatgaatt cagctgtcac   1260

tggctgccag agaacaacct cgtaagttgt agtgagattc tgaagaagtt gaacttgcct   1320

ggaggttcga gggagagcag atagaacatg gccactctga aaggcaaggc catgcttctc   1380

atagaggatg atggctacca ggactccaag gccataaagc ttcatcccaa cagtgacttg   1440

ttgagcagcc aagttcctcg                                               1460


<210> SEQ ID NO 9
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9

cuacagaauc uuacuacaac a                                               21


<210> SEQ ID NO 10
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10

uguuguagua agauucugua gaa                                             23


<210> SEQ ID NO 11
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

cuacagaauc uuacuacaac a                                               21


<210> SEQ ID NO 12
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

uguuguagua agauucugua gaa                                             23


<210> SEQ ID NO 13
<211> LENGTH: 21
<212> TYPE: RNA
<213> ORGANISM: Artificial Sequence
<220> FEATURE:
<221> NAME/KEY: source
```

<223> OTHER INFORMATION: /note="Description of Artificial Sequence:
Synthetic oligonucleotide"

<400> SEQUENCE: 13
cuacagaauc uuacuacaac a 21

<210> SEQ ID NO 14
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 14
uguuguagua agauucugua gaa 23

<210> SEQ ID NO 15
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 15
cuacagaauc uuacuacaac a 21

<210> SEQ ID NO 16
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 16
uguuguagua agauucugua gaa 23

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 17
cuacagaauc uuacuacaac a 21

<210> SEQ ID NO 18
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 18
uguuguagua agauucugua gaa 23

<210> SEQ ID NO 19

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
cuacagaauc uuacuacaac a 21

<210> SEQ ID NO 20
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
uguuguagua agauucugua gaa 23

<210> SEQ ID NO 21
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
cuacagaauc uuacuacaac a 21

<210> SEQ ID NO 22
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
uguuguagua agauucugua gaa 23

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
cuacagaauc uuacuacaac a 21

<210> SEQ ID NO 24
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
uguuguagua agauucugua gaa 23

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25
cuacagaauc uuacuacaac a 21

<210> SEQ ID NO 26
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 26
uguuguagua agauucugua gaa 23

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 27
cuacagaauc uuacuacaac a 21

<210> SEQ ID NO 28
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 28
uguuguagua agauucugua gaa 23

<210> SEQ ID NO 29
<211> LENGTH: 16
<212> TYPE: PRT
<213> ORGANISM: Unknown
<220> FEATURE:
<221> NAME/KEY: source
<223> OTHER INFORMATION: /note="Description of Unknown: RFGF sequence"

<400> SEQUENCE: 29

Ala Ala Val Ala Leu Leu Pro Ala Val Leu Leu Ala Leu Leu Ala Pro
1               5                   10                  15

<210> SEQ ID NO 30
<211> LENGTH: 11
<212> TYPE: PRT
<213> ORGANISM: Unknown

<220> FEATURE:
<221> NAME/KEY: source
<223> OTHER INFORMATION: /note="Description of Unknown:
RFGF analogue sequence"

<400> SEQUENCE: 30

Ala Ala Leu Leu Pro Val Leu Leu Ala Ala Pro
1 5 10

<210> SEQ ID NO 31
<211> LENGTH: 13
<212> TYPE: PRT
<213> ORGANISM: Human immunodeficiency virus

<400> SEQUENCE: 31

Gly Arg Lys Lys Arg Arg Gln Arg Arg Arg Pro Pro Gln
1 5 10

<210> SEQ ID NO 32
<211> LENGTH: 16
<212> TYPE: PRT
<213> ORGANISM: Drosophila sp.

<400> SEQUENCE: 32

Arg Gln Ile Lys Ile Trp Phe Gln Asn Arg Arg Met Lys Trp Lys Lys
1 5 10 15

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 33
cuuacgcuga guacuucgat t 21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 34
ucgaaguacu cagcguaagt t 21

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 35
cacguggaaa aagaaucgaa u 21

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 36
uugggcauca aauauucguu u 21

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 37
gcaucaaaua uucguuuaca a 21

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 38
uugggcauca aauauucguu u 21

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 39
ggcaucaaau auucguuuac a 21

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 40
gggcaucaaa uauucguuua a 21

<210> SEQ ID NO 41
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 41
gggcaucaaa uauucguuua a 21

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
acacguggaa aaagaaucga a 21

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43
ugggcaucaa auauucguuu a 21

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 44
cuacagaauc uuacuacaac a 21

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 45
aggcacgugg auuucuacau a 21

<210> SEQ ID NO 46
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 46
ugaaucaguu uccuugguuu u 21

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
acguggaaaa agaaucgaau a 21

<210> SEQ ID NO 48
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
acuaugaaca guaucacuca a 21

<210> SEQ ID NO 49
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 49
ggcaucaaau auucguuuac a 21

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
uuugggcauc aaauauucgu u 21

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51
agcaugcauu cauacuccca a 21

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
agcagaauuc cauuuaacgu u 21

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
cagaaaguuu auaucuagcu a 21

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
uggcucagaa aguuuauauc u 21

<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
ugguagccau cauccucuau a 21

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
agcuuacauc aguaugcacu a 21

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 57
cagcaugucu ucgcguuuca a 21

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 58
aaagcacacu acuuugagcu u 21

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 59
cagugaagca guucgugcua u 21

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 60
aucaguaugc acucauacuc a 21

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
uaaaaagcac acuacuuuga a 21

<210> SEQ ID NO 62
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 62
aucgaaugug gagaaagaac a 21

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 63
agcagcaugu cuucgcguuu a 21

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
auuaaagcuu acaucaguau a 21

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
aauguggaga aagaaccguu a 21

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
aaguuuauau cuagcuccug a 21

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
uuauugauuu cagcaacacu u 21

<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
cuaaaauagc uuggcauguc a 21

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 69
accuacugug gacuuuaucc u 21

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 70
gcaugucuuc gcguuucaga a 21

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 71
acaucaguau gcacucauac u 21

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 72
agugaagcag uucgugcuau u 21

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 73
ccauuuaaau gugagcggaa u 21

<210> SEQ ID NO 74
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
gcuuacauca guaugcacuc a 21

<210> SEQ ID NO 75
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 75
uuuacaauug aacuucgaga u 21

<210> SEQ ID NO 76
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
augauuuggg caucaaauau u 21

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 77
ucacucacua aaugaaaucu a 21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 78
cucuaguagc cagugaagca a 21

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 79
gaaccucuag gcaaguucaa a 21

<210> SEQ ID NO 80
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 80
cuaugauuug ggcaucaaau a 21

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 81
agcauacauc agcaugcauu a 21

<210> SEQ ID NO 82
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 82
ugaacaguau cacucacuaa a 21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
ccuccgcauc guacuaugaa a 21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 84
ccgcaucgua cuaugaacag u 21

<210> SEQ ID NO 85
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 85
agaaaccuua uaccuagcuc a 21

<210> SEQ ID NO 86
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 86
agaaccucua ggcaaguuca a 21

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 87
aucagcaugc auucauacuc a 21

<210> SEQ ID NO 88
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88
auuuaaaugu gagcggaauu a 21

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 89
acaaaaaucc acauuggauc a 21

<210> SEQ ID NO 90
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
cccauuuaaa ugugagcgga a 21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91
ugucucuaaa auagcuuggc a 21

<210> SEQ ID NO 92
<211> LENGTH: 21

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 92
ugaaaucuau uccuggauag a 21

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 93
agcggaauuc caugcagugu a 21

<210> SEQ ID NO 94
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 94
gaaaccuuau accuagcucc u 21

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
gaaccguucu uucuaugcga a 21

<210> SEQ ID NO 96
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 96
agaaccguuc uuucuaugcg a 21

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 97
gagcagcaug ucuucgcguu u 21

<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 98
uccgcaucgu acuaugaaca a 21

<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 99
aaaauagcuu ggcaugucau u 21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
acaucagcau gcauucauac u 21

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101
cagaaaccuu auaccuagcu a 21

<210> SEQ ID NO 102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
cgcaucguac uaugaacagu a 21

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
cauauagugu uuccauauuc a                                              21

<210> SEQ ID NO 104
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
agccaucuca agcaaguuua a                                              21

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
gcauacauca gcaugcauuc a                                              21

<210> SEQ ID NO 106
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
auuugggcau caaauauucg u                                              21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
agcauauagu guuuccauau u                                              21

<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
gaaccuaaua agugcuacuu u                                              21

<210> SEQ ID NO 109

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 109
uugcaucgga acagaccuga a 21

<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 110
ucagaaaccu uauaccuagc u 21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 111
cagcauauag uguuuccaua u 21

<210> SEQ ID NO 112
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 112
cauugcaucg gaacagaccu a 21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 113
aagcauacau cagcaugcau u 21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 114
agaaccuaau aagugcuacu u 21

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
cucuucugug agcagcaugu a 21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 116
uagccaucuc aagcaaguuu a 21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 117
aaccguucuu ucuaugcgaa a 21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 118
cauacuccca gcauauagug u 21

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 119
gcaguccuug uacccauugu u 21

<210> SEQ ID NO 120
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 120
ugagcagcau gucuucgcgu u 21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
gccaucucaa gcaaguuuaa u 21

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
acaacauaug agauuguucu a 21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
gucauuagga auguuuaaug a 21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124
ccuagaaccu cuaggcaagu u 21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125
uucuagcugc ucuuccuaga a 21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 126
caauugaacu ucgagauacg a 21

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 127
cagcaugcau ucauacuccc a 21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 128
uucuuucuau gcgaacaauc a 21

<210> SEQ ID NO 129
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 129
auucgauucu uuuuccacgu gua 23

<210> SEQ ID NO 130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 130
aaacgaauau uugaugccca aau 23

<210> SEQ ID NO 131
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 131
uuguaaacga auauuugaug ccc 23

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 132
aaacgaauau uugaugccca aau 23

<210> SEQ ID NO 133
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 133
uguaaacgaa uauuugaugc cca 23

<210> SEQ ID NO 134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 134
uuaaacgaau auuugaugcc caa 23

<210> SEQ ID NO 135
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
uuaaacgaau auuugaugcc caa 23

<210> SEQ ID NO 136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
uucgauucuu uuuccacgug uag 23

<210> SEQ ID NO 137
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 137
uaaacgaaua uuugaugccc aaa 23

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138
uguuguagua agauucugua gaa 23

<210> SEQ ID NO 139
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 139
uauguagaaa uccacgugcc uca 23

<210> SEQ ID NO 140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
aaaaccaagg aaacugauuc aac 23

<210> SEQ ID NO 141
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 141
uauucgauuc uuuuuccacg ugu 23

<210> SEQ ID NO 142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
uugagugaua cuguucauag uac 23

<210> SEQ ID NO 143
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
uguaaacgaa uauuugaugc cca 23

<210> SEQ ID NO 144
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 144
aacgaauauu ugaugcccaa auc 23

<210> SEQ ID NO 145
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
uugggaguau gaaugcaugc uga 23

<210> SEQ ID NO 146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
aacguuaaau ggaauucugc uca 23

<210> SEQ ID NO 147
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
uagcuagaua uaaacuuucu gag 23

<210> SEQ ID NO 148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
agauauaaac uuucugagcc acu 23

<210> SEQ ID NO 149
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
uauagaggau gauggcuacc agg 23

<210> SEQ ID NO 150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 150
uagugcauac ugauguaagc uuu 23

<210> SEQ ID NO 151
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
uugaaacgcg aagacaugcu gcu 23

<210> SEQ ID NO 152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
aagcucaaag uagugugcuu uuu 23

<210> SEQ ID NO 153
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
auagcacgaa cugcuucacu ggc 23

<210> SEQ ID NO 154
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
ugaguaugag ugcauacuga ugu 23

<210> SEQ ID NO 155
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
uucaaaguag ugugcuuuuu auu 23

<210> SEQ ID NO 156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
uguucuuucu ccacauucga uua 23

<210> SEQ ID NO 157
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
uaaacgcgaa gacaugcugc uca 23

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
uauacugaug uaagcuuuaa ugu 23

<210> SEQ ID NO 159
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 159
uaacgguucu uucuccacau ucg 23

<210> SEQ ID NO 160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
ucaggagcua gauauaaacu uuc 23

<210> SEQ ID NO 161
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
aaguguugcu gaaaucaaua aaa 23

<210> SEQ ID NO 162
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
ugacaugcca agcuauuuua gag 23

<210> SEQ ID NO 163
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
aggauaaagu ccacaguagg uuu 23

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
uucugaaacg cgaagacaug cug 23

<210> SEQ ID NO 165
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 165
aguaugagug cauacugaug uaa 23

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 166
aauagcacga acugcuucac ugg 23

<210> SEQ ID NO 167
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 167
auuccgcuca cauuuaaaug ggc 23

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 168
ugagugcaua cugauguaag cuu 23

<210> SEQ ID NO 169
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 169
aucucgaagu ucaauuguaa acg 23

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 170
aauauuugau gcccaaauca uag 23

<210> SEQ ID NO 171
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 171
uagauuucau uuagugagug aua 23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
uugcuucacu ggcuacuaga gac 23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
uuugaacuug ccuagagguu cua 23

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 174
uauuugaugc ccaaaucaua gau 23

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
uaaugcaugc ugauguaugc uuu 23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
uuuagugagu gauacuguuc aua 23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
uuucauagua cgaugcggag gcu 23

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
acuguucaua guacgaugcg gag 23

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
ugagcuaggu auaagguuuc uga 23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
uugaacuugc cuagagguuc uag 23

<210> SEQ ID NO 181
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
ugaguaugaa ugcaugcuga ugu 23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
uaauuccgcu cacauuuaaa ugg 23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ugauccaaug uggauuuuug uaa 23

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
uuccgcucac auuuaaaugg gcu 23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
ugccaagcua uuuuagagac agc 23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
ucuauccagg aauagauuuc auu 23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
uacacugcau ggaauuccgc uca 23

<210> SEQ ID NO 188

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 188
aggagcuagg uauaagguuu cug 23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 189
uucgcauaga aagaacgguu cuu 23

<210> SEQ ID NO 190
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 190
ucgcauagaa agaacgguuc uuu 23

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 191
aaacgcgaag acaugcugcu cac 23

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 192
uuguucauag uacgaugcgg agg 23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 193

```
aaugacaugc caagcuauuu uag                                          23


<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194

aguaugaaug caugcugaug uau                                          23


<210> SEQ ID NO 195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195

uagcuaggua uaagguuucu gag                                          23


<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196

uacuguucau aguacgaugc gga                                          23


<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197

ugaauaugga aacacuauau gcu                                          23


<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198

uuaaacuugc uugagauggc uag                                          23


<210> SEQ ID NO 199
<211> LENGTH: 23
<212> TYPE: RNA
<213> ORGANISM: Artificial Sequence
<220> FEATURE:
```

<221> NAME/KEY: source
<223> OTHER INFORMATION: /note="Description of Artificial Sequence: Synthetic oligonucleotide"

<400> SEQUENCE: 199
ugaaugcaug cugauguaug cuu 23

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 200
acgaauauuu gaugcccaaa uca 23

<210> SEQ ID NO 201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 201
aauauggaaa cacuauaugc ugg 23

<210> SEQ ID NO 202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 202
aaaguagcac uuauuagguu cuc 23

<210> SEQ ID NO 203
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 203
uucaggucug uuccgaugca aug 23

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 204
agcuagguau aagguuucug agc 23

<210> SEQ ID NO 205
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 205
auauggaaac acuauaugcu ggg 23

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
uaggucuguu ccgaugcaau gau 23

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 207
aaugcaugcu gauguaugcu uua 23

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 208
aaguagcacu uauuagguuc ucu 23

<210> SEQ ID NO 209
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 209
uacaugcugc ucacagaaga gaa 23

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 210
uaaacuugcu ugagauggcu agu 23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 211
uuucgcauag aaagaacggu ucu 23

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 212
acacuauaug cugggaguau gaa 23

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 213
aacaaugggu acaaggacug caa 23

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 214
aacgcgaaga caugcugcuc aca 23

<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 215
auuaaacuug cuugagaugg cua 23

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 216
uagaacaauc ucauauguug uag 23

<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 217
ucauuaaaca uuccuaauga cau 23

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 218
aacuugccua gagguucuag gaa 23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 219
uucuaggaag agcagcuaga acu 23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 220
ucguaucucg aaguucaauu gua 23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 221
ugggaguaug aaugcaugcu gau 23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 222
ugauuguucg cauagaaaga acg 23

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 223
cacguggaaa aagaaucgaa u 21

<210> SEQ ID NO 224
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 224
uugggcauca aauauucguu u 21

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 225
gcaucaaaua uucguuuaca a 21

<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 226
uugggcauca aauauucguu u 21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 227
ggcaucaaau auucguuuac a 21

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 228
gggcaucaaa uauucguuua a 21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 229
gggcaucaaa uauucguuua a 21

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 230
acacguggaa aaagaaucga a 21

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 231
ugggcaucaa auauucguuu a 21

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 232
cuacagaauc uuacuacaac a 21

<210> SEQ ID NO 233
<211> LENGTH: 21
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 233
aggcacgugg auuucuacau a 21

<210> SEQ ID NO 234
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 234
ugaaucaguu uccuugguuu u 21

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 235
acguggaaaa agaaucgaau a 21

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 236
acuaugaaca guaucacuca a 21

<210> SEQ ID NO 237
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 237
ggcaucaaau auucguuuac a 21

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 238
uuugggcauc aaauauucgu u 21

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
agcaugcauu cauacuccca a 21

<210> SEQ ID NO 240
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
agcagaauuc cauuuaacgu u 21

<210> SEQ ID NO 241
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 241
cagaaaguuu auaucuagcu a 21

<210> SEQ ID NO 242
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 242
uggcucagaa aguuuauauc u 21

<210> SEQ ID NO 243
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 243
ugguagccau cauccucuau a 21

<210> SEQ ID NO 244
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 244
agcuuacauc aguaugcacu a 21

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 245
cagcaugucu ucgcguuuca a 21

<210> SEQ ID NO 246
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 246
aaagcacacu acuuugagcu u 21

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 247
cagugaagca guucgugcua u 21

<210> SEQ ID NO 248
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 248
aucaguaugc acucauacuc a 21

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 249
uaaaaagcac acuacuuuga a 21

<210> SEQ ID NO 250
<211> LENGTH: 21

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 250
aucgaaugug gagaaagaac a 21

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 251
agcagcaugu cuucgcguuu a 21

<210> SEQ ID NO 252
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 252
auuaaagcuu acaucaguau a 21

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 253
aauguggaga aagaaccguu a 21

<210> SEQ ID NO 254
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 254
aaguuuauau cuagcuccug a 21

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 255
uuauugauuu cagcaacacu u 21

<210> SEQ ID NO 256
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 256
cuaaaauagc uuggcauguc a 21

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 257
accuacugug gacuuuaucc u 21

<210> SEQ ID NO 258
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 258
gcaugucuuc gcguuucaga a 21

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
acaucaguau gcacucauac u 21

<210> SEQ ID NO 260
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
agugaagcag uucgugcuau u 21

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
ccauuuaaau gugagcggaa u 21

<210> SEQ ID NO 262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
gcuuacauca guaugcacuc a 21

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
uuuacaauug aacuucgaga u 21

<210> SEQ ID NO 264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 264
augauuuggg caucaaauau u 21

<210> SEQ ID NO 265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 265
ucacucacua aaugaaaucu a 21

<210> SEQ ID NO 266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
cucuaguagc cagugaagca a 21

<210> SEQ ID NO 267

<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
gaaccucuag gcaaguucaa a 21

<210> SEQ ID NO 268
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
cuaugauuug ggcaucaaau a 21

<210> SEQ ID NO 269
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
agcauacauc agcaugcauu a 21

<210> SEQ ID NO 270
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 270
ugaacaguau cacucacuaa a 21

<210> SEQ ID NO 271
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 271
ccuccgcauc guacuaugaa a 21

<210> SEQ ID NO 272
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 272
ccgcaucgua cuaugaacag u 21

<210> SEQ ID NO 273
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 273
agaaaccuua uaccuagcuc a 21

<210> SEQ ID NO 274
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 274
agaaccucua ggcaaguuca a 21

<210> SEQ ID NO 275
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 275
aucagcaugc auucauacuc a 21

<210> SEQ ID NO 276
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 276
auuuaaaugu gagcggaauu a 21

<210> SEQ ID NO 277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
acaaaaaucc acauuggauc a 21

<210> SEQ ID NO 278
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 278
cccauuuaaa ugugagcgga a 21

<210> SEQ ID NO 279
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
ugucucuaaa auagcuuggc a 21

<210> SEQ ID NO 280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
ugaaaucuau uccuggauag a 21

<210> SEQ ID NO 281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
agcggaauuc caugcagugu a 21

<210> SEQ ID NO 282
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 282
gaaaccuuau accuagcucc u 21

<210> SEQ ID NO 283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 283
gaaccguucu uucuaugcga a 21

<210> SEQ ID NO 284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 284
agaaccguuc uuucuaugcg a 21

<210> SEQ ID NO 285
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 285
gagcagcaug ucuucgcguu u 21

<210> SEQ ID NO 286
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 286
uccgcaucgu acuaugaaca a 21

<210> SEQ ID NO 287
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
aaaauagcuu ggcaugucau u 21

<210> SEQ ID NO 288
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
acaucagcau gcauucauac u 21

<210> SEQ ID NO 289
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
cagaaaccuu auaccuagcu a 21

<210> SEQ ID NO 290
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
cgcaucguac uaugaacagu a 21

<210> SEQ ID NO 291
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
cauauagugu uuccauauuc a 21

<210> SEQ ID NO 292
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 292
agccaucuca agcaaguuua a 21

<210> SEQ ID NO 293
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 293
gcauacauca gcaugcauuc a 21

<210> SEQ ID NO 294
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 294
auuugggcau caaauauucg u 21

<210> SEQ ID NO 295
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 295
agcauauagu guuuccauau u 21

<210> SEQ ID NO 296
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 296
gaaccuaaua agugcuacuu u 21

<210> SEQ ID NO 297
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 297
uugcaucgga acagaccuga a 21

<210> SEQ ID NO 298
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
ucagaaaccu uauaccuagc u 21

<210> SEQ ID NO 299
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 299
cagcauauag uguuuccaua u 21

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 300
cauugcaucg gaacagaccu a 21

<210> SEQ ID NO 301
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 301
aagcauacau cagcaugcau u 21

<210> SEQ ID NO 302
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 302
agaaccuaau aagugcuacu u 21

<210> SEQ ID NO 303
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 303
cucuucugug agcagcaugu a 21

<210> SEQ ID NO 304
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 304
uagccaucuc aagcaaguuu a 21

<210> SEQ ID NO 305
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 305
aaccguucuu ucuaugcgaa a 21

<210> SEQ ID NO 306
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 306
cauacuccca gcauauagug u 21

<210> SEQ ID NO 307
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 307
gcaguccuug uacccauugu u 21

<210> SEQ ID NO 308
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 308
ugagcagcau gucuucgcgu u 21

<210> SEQ ID NO 309
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 309
gccaucucaa gcaaguuuaa u 21

<210> SEQ ID NO 310
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 310
acaacauaug agauuguucu a 21

<210> SEQ ID NO 311
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 311
gucauuagga auguuuaaug a 21

<210> SEQ ID NO 312
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312

ccuagaaccu cuaggcaagu u                                              21


<210> SEQ ID NO 313
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313

uucuagcugc ucuuccuaga a                                              21


<210> SEQ ID NO 314
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314

caauugaacu ucgagauacg a                                              21


<210> SEQ ID NO 315
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315

cagcaugcau ucauacuccc a                                              21


<210> SEQ ID NO 316
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316

uucuuucuau gcgaacaauc a                                              21


<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317

auucgauucu uuuuccacgu gua                                            23
```

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 318
aaacgaauau uugaugccca aau 23

<210> SEQ ID NO 319
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 319
uuguaaacga auauuugaug ccc 23

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 320
aaacgaauau uugaugccca aau 23

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 321
uguaaacgaa uauuugaugc cca 23

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 322
uuaaacgaau auuugaugcc caa 23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 323
uuaaacgaau auuugaugcc caa 23

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 324
uucgauucuu uuuccacgug uag 23

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 325
uaaacgaaua uuugaugccc aaa 23

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 326
uguuguagua agauucugua gaa 23

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 327
uauguagaaa uccacgugcc uca 23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 328
aaaaccaagg aaacugauuc aac 23

<210> SEQ ID NO 329
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 329
uauucgauuc uuuuuccacg ugu 23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 330
uugagugaua cuguucauag uac 23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 331
uguaaacgaa uauuugaugc cca 23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 332
aacgaauauu ugaugcccaa auc 23

<210> SEQ ID NO 333
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 333
uugggaguau gaaugcaugc uga 23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 334
aacguuaaau ggaauucugc uca 23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 335
uagcuagaua uaaacuuucu gag 23

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 336
agauauaaac uuucugagcc acu 23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 337
uauagaggau gauggcuacc agg 23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 338
uagugcauac ugauguaagc uuu 23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 339
uugaaacgcg aagacaugcu gcu 23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 340
aagcucaaag uagugugcuu uuu 23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 341
auagcacgaa cugcuucacu ggc 23

<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 342
ugaguaugag ugcauacuga ugu 23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 343
uucaaaguag ugugcuuuuu auu 23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 344
uguucuuucu ccacauucga uua 23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 345
uaaacgcgaa gacaugcugc uca 23

<210> SEQ ID NO 346

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 346
uauacugaug uaagcuuuaa ugu 23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 347
uaacgguucu uucuccacau ucg 23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 348
ucaggagcua gauauaaacu uuc 23

<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 349
aaguguugcu gaaaucaaua aaa 23

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 350
ugacaugcca agcuauuuua gag 23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 351
aggauaaagu ccacaguagg uuu 23

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 352
uucugaaacg cgaagacaug cug 23

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 353
aguaugagug cauacugaug uaa 23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 354
aauagcacga acugcuucac ugg 23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 355
auuccgcuca cauuuaaaug ggc 23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 356
ugagugcaua cugauguaag cuu 23

<210> SEQ ID NO 357
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 357
aucucgaagu ucaauuguaa acg 23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 358
aauauuugau gcccaaauca uag 23

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 359
uagauuucau uuagugagug aua 23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 360
uugcuucacu ggcuacuaga gac 23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
uuugaacuug ccuagagguu cua 23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 362
uauuugaugc ccaaaucaua gau 23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 363
uaaugcaugc ugauguaugc uuu 23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 364
uuuagugagu gauacuguuc aua 23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 365
uuucauagua cgaugcggag gcu 23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 366
acuguucaua guacgaugcg gag 23

<210> SEQ ID NO 367
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 367
ugagcuaggu auaagguuuc uga 23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 368
uugaacuugc cuagagguuc uag 23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 369
ugaguaugaa ugcaugcuga ugu 23

<210> SEQ ID NO 370
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 370
uaauuccgcu cacauuuaaa ugg 23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 371
ugauccaaug uggauuuuug uaa 23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 372
uuccgcucac auuuaaaugg gcu 23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 373
ugccaagcua uuuuagagac agc 23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 374
ucuauccagg aauagauuuc auu 23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 375
uacacugcau ggaauuccgc uca 23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 376
aggagcuagg uauaagguuu cug 23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 377
uucgcauaga aagaacgguu cuu 23

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 378
ucgcauagaa agaacgguuc uuu 23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 379
aaacgcgaag acaugcugcu cac 23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 380
uuguucauag uacgaugcgg agg 23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 381
aaugacaugc caagcuauuu uag 23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 382
aguaugaaug caugcugaug uau 23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 383
uagcuaggua uaagguuucu gag 23

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 384
uacuguucau aguacgaugc gga 23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 385
ugaauaugga aacacuauau gcu 23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 386
uuaaacuugc uugagauggc uag 23

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 387
ugaaugcaug cugauguaug cuu 23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 388
acgaauauuu gaugcccaaa uca 23

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 389
aauauggaaa cacuauaugc ugg 23

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 390
aaaguagcac uuauuagguu cuc 23

<210> SEQ ID NO 391
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 391
uucaggucug uuccgaugca aug 23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 392
agcuagguau aagguuucug agc 23

<210> SEQ ID NO 393
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 393
auauggaaac acuauaugcu ggg 23

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 394
uaggucuguu ccgaugcaau gau 23

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 395
aaugcaugcu gauguaugcu uua 23

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 396
aaguagcacu uauuagguuc ucu 23

<210> SEQ ID NO 397
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 397
uacaugcugc ucacagaaga gaa 23

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 398
uaaacuugcu ugagauggcu agu 23

<210> SEQ ID NO 399
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 399
uuucgcauag aaagaacggu ucu 23

<210> SEQ ID NO 400
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 400
acacuauaug cugggaguau gaa 23

<210> SEQ ID NO 401
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 401
aacaaugggu acaaggacug caa 23

<210> SEQ ID NO 402
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 402
aacgcgaaga caugcugcuc aca 23

<210> SEQ ID NO 403
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 403
auuaaacuug cuugagaugg cua 23

<210> SEQ ID NO 404
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 404
uagaacaauc ucauauguug uag 23

<210> SEQ ID NO 405
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 405
ucauuaaaca uuccuaauga cau 23

<210> SEQ ID NO 406
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 406
aacuugccua gagguucuag gaa 23

<210> SEQ ID NO 407
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 407
uucuaggaag agcagcuaga acu 23

<210> SEQ ID NO 408
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 408
ucguaucucg aaguucaauu gua 23

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 409
ugggaguaug aaugcaugcu gau 23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 410
ugauuguucg cauagaaaga acg 23

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 411
uacacgugga aaaagaaucg aau 23

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 412
auuugggcau caaauauucg uuu 23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 413
gggcaucaaa uauucguuua caa 23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 414
auuugggcau caaauauucg uuu 23

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 415
ugggcaucaa auauucguuu aca 23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 416
uugggcauca aauauucguu uac 23

<210> SEQ ID NO 417
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 417
uugggcauca aauauucguu uac 23

<210> SEQ ID NO 418
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 418
cuacacgugg aaaaagaauc gaa 23

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 419
uuugggcauc aaauauucgu uua 23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 420
uucuacagaa ucuuacuaca aca 23

<210> SEQ ID NO 421
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 421
ugaggcacgu ggauuucuac auc 23

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 422
guugaaucag uuuccuuggu uuu 23

<210> SEQ ID NO 423
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 423
acacguggaa aaagaaucga aug 23

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 424
guacuaugaa caguaucacu cac 23

<210> SEQ ID NO 425

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 425
ugggcaucaa auauucguuu aca 23

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 426
gauuugggca ucaaauauuc guu 23

<210> SEQ ID NO 427
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 427
ucagcaugca uucauacucc cag 23

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 428
ugagcagaau uccauuuaac guu 23

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 429
cucagaaagu uuauaucuag cuc 23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 430
aguggcucag aaaguuuaua ucu 23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 431
ccugguagcc aucauccucu aug 23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 432
aaagcuuaca ucaguaugca cuc 23

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 433
agcagcaugu cuucgcguuu cag 23

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 434
aaaaagcaca cuacuuugag cuu 23

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 435
gccagugaag caguucgugc uau 23

<210> SEQ ID NO 436
<211> LENGTH: 23
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 436
acaucaguau gcacucauac ucc 23

<210> SEQ ID NO 437
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
aauaaaaagc acacuacuuu gag 23

<210> SEQ ID NO 438
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
uaaucgaaug uggagaaaga acc 23

<210> SEQ ID NO 439
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
ugagcagcau gucuucgcgu uuc 23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
acauuaaagc uuacaucagu aug 23

<210> SEQ ID NO 441
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 441
cgaaugugga gaaagaaccg uuc 23

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 442
gaaaguuuau aucuagcucc ugg 23

<210> SEQ ID NO 443
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 443
uuuuauugau uucagcaaca cuu 23

<210> SEQ ID NO 444
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 444
cucuaaaaua gcuuggcaug uca 23

<210> SEQ ID NO 445
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 445
aaaccuacug uggacuuuau ccu 23

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 446
cagcaugucu ucgcguuuca gag 23

<210> SEQ ID NO 447
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 447
uuacaucagu augcacucau acu 23

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 448
ccagugaagc aguucgugcu auu 23

<210> SEQ ID NO 449
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 449
gcccauuuaa augugagcgg aau 23

<210> SEQ ID NO 450
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 450
aagcuuacau caguaugcac uca 23

<210> SEQ ID NO 451
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 451
cguuuacaau ugaacuucga gau 23

<210> SEQ ID NO 452
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 452
cuaugauuug ggcaucaaau auu 23

<210> SEQ ID NO 453
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
uaucacucac uaaaugaaau cua 23

<210> SEQ ID NO 454
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
gucucuagua gccagugaag cag 23

<210> SEQ ID NO 455
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
uagaaccucu aggcaaguuc aag 23

<210> SEQ ID NO 456
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
aucuaugauu ugggcaucaa aua 23

<210> SEQ ID NO 457
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
aaagcauaca ucagcaugca uuc 23

<210> SEQ ID NO 458
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
uaugaacagu aucacucacu aaa 23

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 459
agccuccgca ucguacuaug aac 23

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 460
cuccgcaucg uacuaugaac agu 23

<210> SEQ ID NO 461
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 461
ucagaaaccu uauaccuagc ucc 23

<210> SEQ ID NO 462
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 462
cuagaaccuc uaggcaaguu caa 23

<210> SEQ ID NO 463
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 463
acaucagcau gcauucauac ucc 23

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 464
ccauuuaaau gugagcggaa uuc 23

<210> SEQ ID NO 465
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 465
uuacaaaaau ccacauugga ucc 23

<210> SEQ ID NO 466
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 466
agcccauuua aaugugagcg gaa 23

<210> SEQ ID NO 467
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 467
gcugucucua aaauagcuug gca 23

<210> SEQ ID NO 468
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 468
aaugaaaucu auuccuggau aga 23

<210> SEQ ID NO 469
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 469
ugagcggaau uccaugcagu guc 23

<210> SEQ ID NO 470
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 470
cagaaaccuu auaccuagcu ccu 23

<210> SEQ ID NO 471
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 471
aagaaccguu cuuucuaugc gaa 23

<210> SEQ ID NO 472
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
aaagaaccgu ucuuucuaug cga 23

<210> SEQ ID NO 473
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 473
gugagcagca ugucuucgcg uuu 23

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 474
ccuccgcauc guacuaugaa cag 23

<210> SEQ ID NO 475
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 475
cuaaaauagc uuggcauguc auu 23

<210> SEQ ID NO 476
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 476
auacaucagc augcauucau acu 23

<210> SEQ ID NO 477
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 477
cucagaaacc uuauaccuag cuc 23

<210> SEQ ID NO 478
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 478
uccgcaucgu acuaugaaca gua 23

<210> SEQ ID NO 479
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 479
agcauauagu guuuccauau ucc 23

<210> SEQ ID NO 480
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 480
cuagccaucu caagcaaguu uaa 23

<210> SEQ ID NO 481
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 481
aagcauacau cagcaugcau uca 23

<210> SEQ ID NO 482
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 482
ugauuugggc aucaaauauu cgu 23

<210> SEQ ID NO 483
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 483
ccagcauaua guguuuccau auu 23

<210> SEQ ID NO 484
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 484
gagaaccuaa uaagugcuac uuu 23

<210> SEQ ID NO 485
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 485
cauugcaucg gaacagaccu gaa 23

<210> SEQ ID NO 486
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 486
gcucagaaac cuuauaccua gcu 23

<210> SEQ ID NO 487
<211> LENGTH: 23

<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 487
cccagcauau aguguuucca uau 23

<210> SEQ ID NO 488
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 488
aucauugcau cggaacagac cug 23

<210> SEQ ID NO 489
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 489
uaaagcauac aucagcaugc auu 23

<210> SEQ ID NO 490
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 490
agagaaccua auaagugcua cuu 23

<210> SEQ ID NO 491
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 491
uucucuucug ugagcagcau guc 23

<210> SEQ ID NO 492
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 492
acuagccauc ucaagcaagu uuc 23

<210> SEQ ID NO 493
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 493
agaaccguuc uuucuaugcg aac 23

<210> SEQ ID NO 494
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 494
uucauacucc cagcauauag ugu 23

<210> SEQ ID NO 495
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 495
uugcaguccu uguacccauu guu 23

<210> SEQ ID NO 496
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 496
ugugagcagc augucuucgc guu 23

<210> SEQ ID NO 497
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 497
uagccaucuc aagcaaguuu aau 23

<210> SEQ ID NO 498
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 498
cuacaacaua ugagauuguu cuc 23

<210> SEQ ID NO 499
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 499
augucauuag gaauguuuaa ugc 23

<210> SEQ ID NO 500
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 500
uuccuagaac cucuaggcaa guu 23

<210> SEQ ID NO 501
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 501
aguucuagcu gcucuuccua gaa 23

<210> SEQ ID NO 502
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 502
uacaauugaa cuucgagaua cgg 23

<210> SEQ ID NO 503
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 503
aucagcaugc auucauacuc cca 23

<210> SEQ ID NO 504

<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 504
cguucuuucu augcgaacaa uca 23

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 505
cuacagaauc uuacuacaac a 21

<210> SEQ ID NO 506
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 506
uguuguagua agauucugua gaa 23

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 507
cuacagaauc uuacuacaac a 21

<210> SEQ ID NO 508
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 508
uguuguagua agauucugua gaa 23

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 509
cuacagaauc uuacuacaac a 21

<210> SEQ ID NO 510
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 510
uguuguagua agauucugua gaa 23

<210> SEQ ID NO 511
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 511
cuacagaauc uuacuacaac a 21

<210> SEQ ID NO 512
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 512
uguuguagua agauucugua gaa 23

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 513
cuacagaauc uuacuacaac a 21

<210> SEQ ID NO 514
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 514
uguuguagua agauucugua gaa 23

<210> SEQ ID NO 515
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 515
cuacagaauc uuacuacaac a 21

<210> SEQ ID NO 516
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 516
uguuguagua agauucugua gaa 23

<210> SEQ ID NO 517
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 517
cuacagaauc uuacuacaac a 21

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 518
uguuguagua agauucugua gaa 23

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 519
uugggcauca aauauucguu u 21

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 520
aaacgaauau uugaugccca aau 23

-continued

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 521
ugguagccau cauccucuau a 21

<210> SEQ ID NO 522
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 522
uauagaggau gauggcuacc agg 23

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 523
agcagaauuc cauuuaacgu u 21

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 524
aacguuaaau ggaauucugc uca 23

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 525
aggcacgugg auuucuacau a 21

<210> SEQ ID NO 526
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 526
uauguagaaa uccacgugcc uca 23

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 527
cacguggaaa aagaaucgaa u 21

<210> SEQ ID NO 528
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 528
auucgauucu uuuuccacgu gua 23

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 529
cagaaaguuu auaucuagcu a 21

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 530
uagcuagaua uaaacuuucu gag 23

<210> SEQ ID NO 531
<211> LENGTH: 21
<212> TYPE: RNA

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531

ugaaucaguu uccuugguuu u                                             21


<210> SEQ ID NO 532
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532

aaaaccaagg aaacugauuc aac                                           23
```